US006808911B2

(12) United States Patent
Webster et al.

(10) Patent No.: US 6,808,911 B2
(45) Date of Patent: Oct. 26, 2004

(54) ISOLATED HUMAN KINASE PROTEINS, NUCLEIC ACID MOLECULES ENCODING HUMAN KINASE PROTEINS, AND USES THEREOF

(75) Inventors: Marion Webster, San Francisco, CA (US); Ming-Hui Wei, Germantown, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 65 days.

(21) Appl. No.: 10/274,409

(22) Filed: Oct. 21, 2002

(65) Prior Publication Data
US 2003/0054529 A1 Mar. 20, 2003

Related U.S. Application Data

(62) Division of application No. 09/803,671, filed on Aug. 12, 2001, now Pat. No. 6,582,946.

(51) Int. Cl.[7] .......................... C12N 9/12; C12N 15/00; C07H 21/04; C07K 1/00

(52) U.S. Cl. ...................... 435/194; 435/440; 530/350; 536/23.2

(58) Field of Search ................................. 435/194, 440; 530/350; 536/23.2

(56) References Cited

FOREIGN PATENT DOCUMENTS

WO    WO 0118014    3/2001

OTHER PUBLICATIONS

Results of BLAST search of SEQ ID No.: 2 against Derwent (FastAlert and GeneSeqP) and NCBI (pataa) protein patent databases on Jul. 22, 2003.
International Search Report dated Jan. 3, 2003.

Primary Examiner—P. Achutamurthy
Assistant Examiner—Yong Pak
(74) Attorney, Agent, or Firm—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

16 Claims, 32 Drawing Sheets

```
   1 TTTCCTTGGA TTTCCAGTTT TCCACCCAGC TCTGAAGACA CTGTTGGTAC
  51 TTAAAAATAT TTAACTAAGA CTGTGTCATT TTGCAGGTTG TTGGATTTCT
 101 TCTGGAAAAG TGAGTAGATA TCACCCTTTG CAATTACAGC AATCGAACCG
 151 CAATTCATGT AGCTAATTGC AATATCCAAA GACAACTCTT GGCAGTCAAT
 201 AGAATCCAGG CTCCCCAAAT GCAACTTCTA CAAAGTTCAT GGCAAGGTGA
 251 TCTTGAGCAA GTTCAACATT TACTGAGATC CTAAACTTTG TGATTTTAGT
 301 GGAAAATCAG CAATACATTA TGTGTCACAA ATAGAGAGTT CAAAGAAACA
 351 GCAGCTTTTG GACATTTTAA TGAGTTCTAT GCCAAAACCA GAAAGACATG
 401 CTGAGTCATT GCTTGACATT TGTCATGATA CAAACTCTTC TCCAACTGAT
 451 TTGATGACAG TTACCAAAAA TCAAACATC ATCTTGCAAA GCATCAGCAG
 501 AAGTGAGGAG TTCGACCAAG ATGGTGACTG CAGTCATTCC ACACTGGTTA
 551 ATGAAGAAGA AGATCCCAGT GGTGGTAGAC AGGACTGGCA ACCCAGGACA
 601 GAAGGTGTTG AGATCACTGT AACTTTTCCA AGAGATGTCA GTCCTCCCCA
 651 AGAAATGAGC CAAGAAGACT TAAAAGAAAA GAATCTGATA AACTCATCGC
 701 TTCAAGAATG GGCAAGCA CATGCAGTTT CTCATCCAAA TGAAATAGAA
 751 ACGGTGGAGC TCAGGAAAAA GAAGCTGACC ATGCGGCCCT TAGTTTTGCA
 801 AAAAGAGGAA AGTTCCAGGG AGCTCTGCAA TGTGAACTTG GCTTTTTGC
 851 TACCAAGATC TTGTTTAGAA CTGAACATTT CCAAGTCTGT AACCAGAGAA
 901 GATGCTCCTC ATTTTCTGAA GGAGCAGCAA AGAAAATCTG AAGAGTTTTC
 951 GACCTCTCAT ATGAAGTACA GTGGCCGAAG CATCAAGTTC CTTCTGCCAC
1001 CACTGTCACT CTTGCCCACG CGATCTGGTG TCCTTACTAT CCCCCAAAAT
1051 CACAAGTTTC CAAAAGAAAA AGAAAGAAAC ATTCCAAGTC TCACATCTTT
1101 TGTGCCTAAG CTCTCAGTGT CTGTTCGTCA ATCTGATGAG CTCACGCCAT
1151 CAAACGAGCC TCCGGGAGCC CTAGTTAAGT CGTTGATGGA TCCGACTCTC
1201 AGGTCTTCTG ATGGCTTCAT TTGGTCAAGA AACATGTGCT CTTTTCCTAA
1251 GACTAACCAT CACAGGCAAT GCCTGGAGAA GGAGGAAAAC TGGAAATCCA
1301 AGGAAATAGA AGAATGTAAC AAAATTGAAA TCACTCACTT TGAAAAAGGG
1351 CAGTCTTTGG TGTCTTTTGA GAATTTGAAG GAAGGCAATA TTCCTGCAGT
1401 TAGGGAAGAG GATATTGACT GCCATGGTAG TAAAACGCGA AAACCTGAAG
1451 AAGAGAACTC TCAATATCTT TCATCAAGAA AGAATGAGAG TTCAGTAGCC
1501 AAAAACTATG AACAAGATCC AGAAATAGTA TGTACCATTC CAAGCAAGTT
1551 CCAAGAAACC CAGCATTCAG AAATAACTCC AAGCCAGGAT GAAGAGATGA
1601 GAAATAATAA AGCTGCTTCA AAAAGAGTTT CATTACATAA AAATGAAGCA
1651 ATGGAACCAA ACAATATTTT AGAAGAGTGT ACTGTACTTA AAAGCTTATC
1701 CAGTGTAGTC TTTGATGACC CCATTGATAA ACTCCCAGAA GGTTGAGCA
1751 GCATGGAGAC AAACATAAAA ATATCAATAG CAGAAAGAGC CAAACCAGAA
1801 ATGAGTAGGA TGGTGCCTCT TATCCACATC ACCTTCCCTG TGGATGGAAG
1851 CCCCAAGGAA CCAGTGATAG CCAAACCAAG CCTCCAAACA AGAAAGGGAA
1901 CCATTCATAA CAACCATAGT GTCAACATAC CTGTACACCA AGAAAATGAC
1951 AAGCATAAGA TGAATTCCCA TAGGAGCAGA CGTATCACCA ATAAATGTCG
2001 ATCTTCACAC AGTGAGAGGA AGAGCAATAT CAGAACAAGA CTTTCTCAGA
2051 AAAAAACACA TATGAAATGC CCAAAGACTT CATTTGGCAT TAAACAAGAG
2101 CACAAAGTCT TAATTTCTAA AGAAAAGAGT TCCAAGGCTG TACATAGCAA
2151 CCTACATGAC ATTGAAAATG GTGATTATCC TTCAAAGATGA AATTCATCCC
2201 TAAAGTCTTC AGGAAATGAG TTTCTATCTT CCAAAGATGA AATTCATCCC
2251 ATGAACTTGG CTCAGACACC TGAGCAGTCC ATGAAACAGA ATGAATTCCC
2301 TCCTGTCTCA GATTTATCCA TTGTTGAAGA AGTTTCTATG GAAGAGTCTA
2351 CTGGTGATAG AGACATTTCT AACAATCAAA TACTCACCAC AAGCCTCAGA
2401 GATCTGCAAG AACTTGAAGA GCTACATCAC CAGATCCCAT TTATCCCTTC
2451 AGAAGACAGC TGGGCAGTGC CCAGTGAGAA GAATTCTAAC AAGTATGTAC
2501 AGCAAGAAAA GCAGAATACA GCATCTCTTA GTAAAGTAAA TGCCAGCCGA
2551 ATTTTAACTA ATGATCTAGA GTTTGATAGT GTTTCAGATC ACTCTAAAAC
2601 ACTTACAAAT TTCTCTTTCC AAGCAAAACA AGAAAGTGCA TCTTCCCAGA
2651 CATATCAATA TTGGGTACAT TATTTGGATC ATGATAGTTT AGCAAATAAG
2701 TCAATCACAT ATCAAATGTT TGGAAAAACC TTAAGTGGCA CAAATTCAAT
2751 TTCCCAAGAA ATTATGGACT CTGTAAATAA TGAAGAATTG ACAGATGAAC
2801 TATTAGGTTG TCTAGCTGCA GAATTATTAG CTCTTGATGA GAAAGATAAC
2851 AACTCTTGCC AAAAAATGGC AAATGAAACA GATCCTGAAA ACCTAAATCT
2901 TGTCCTCAGA TGGAGAGGAA GTACCCCAAA AGAAATGGGC AGAGAGACAA
2951 CAAAAGTCAA AATACAGAGG CATAGTAGTG GGCTCAGGAT ATATGACAGG
3001 GAGGAGAAAT TTCTCATCTC AAATGAAAAG AAGATATTTT CTGAAAATAG
3051 TTTAAAGTCT GAAGAACCTA TCCTATGGAC CAAGGGTGAG ATTCTTGGAA
3101 AGGGAGCCTA CGGCACAGTA TACTGTGGTC TCACTAGTCA AGGACAGCTA
3151 ATAGCTGTAA AACAGGTGGC TTTGGATACC TCTAATAAAT TAGCTGCTGA
3201 AAAGGAATAC CGGAAACTAC AGGAAGAAGT AGATTTGCTC AAAGCACTGA
3251 AACATGTCAA CATTGTGGCC TATTTGGGGA CATGCTTGCA AGAGAACACT
3301 GTGAGCATTT TCATGGAGTT TGTTCCTGGT GGCTCAATCT CTAGTATTAT
3351 AAACCGTTTT GGGCCATTGC CTGAGATGGT GTTCTGTAAA TATACGAAAC
3401 AAATACTTCA AGGTGTTGCT TATCTCCATG AGAACTGTGT GGTACATCGC
3451 GATATCAAAG GAAATAATGT TATGCTCATG CCAACTGGAA TAATAAAGCT
3501 GATTGACTTT GGCTGTGCCA GGCGTTTGGC CTGGGCAGGT TTAAATGGCA
3551 CCCACAGTGA CATGCTTAAG TCCATGCATG GGACTCCATA TTGGATGGCC
3601 CCAGAAGTCA TCAATGAGTC TGGCTATGGA CGGAAATCAG ATATCTGGAG
3651 CATTGGTTGT ACTGTGTTTG AGATGGCTAC AGGGAAGCCT CCACTGGCTT
3701 CCATGGACAG GATGGCCGCC ATGTTTTACA TCGGAGCACA CCGAGGGCTG
3751 ATGCCTCCTT TACCAGACCA CTTCTCAGAA AATGCAGCAG ACTTTGTGCG
3801 CATGTGCCTG ACCAGGGACC AGCATGAGCG ACCTTCTGCT CTCCAGCTCC
```

FIGURE 1A

```
3851 TGAAGCACTC CTTCTTGGAG AGAAGTCACT GAATATACAT CAAGACTTTC
3901 TTCCCAGTTC CACTGCAGAT GCTCCCTTGC TTAATTGTGG GGAATGATGG
3951 CTAAGGGATC TTTGTTTCCC CACTGAAAAT TCAGTCTAAC CCAGTTTAAG
4001 CAGATCCTAT GGAGTCATTA ACTGAAAGTT GCAGTTACAT ATTAGCCTCC
4051 TCAAGTGTCA GACATTATTA CTCATAGTAT CAGAAAACAT GTTCTTAATA
4101 ACAACAAAAA ACTATTTCAG TGTTTACAGT TTTGATTGTC CAGGAACTAC
4151 ATTCTCTAGT GTTTTATATG ACATTTCTTT TTATTTTTGG CCTGTCCTGT
4201 CAATTTTAAT GTTGTTAGTT TAAAATAAAT TGTAAAAACA CCTTAAAAAA
4251 AAAAAAAAAA AAAAAAAAAA AAAACATGTC GGCCGCCTCG GCCCAGTCGA
4301 CTCTAGA
(SEQ ID NO:1)
```

FEATURES:
5'UTR:        1 - 378
Start Codon: 379
Stop Codon:  3880
3'UTR:       3883

Homologous proteins:
Top 10 BLAST Hits
```
CRA|147000022596359 /altid=gi|10439647 /def=dbj|BAB15538.1| (AK...    357   4e-97
CRA|18000005192474  /altid=gi|4028547  /def=gb|AAC97114.1|  (AF093...  271   4e-71
CRA|18000005097809  /altid=gi|2342423  /def=dbj|BAA21855.1| (AB00...   263   7e-69
CRA|18000005097808  /altid=gi|2342421  /def=dbj|BAA21854.1| (AB00...   263   7e-69
CRA|18000004901837  /altid=gi|477094   /def=pir|A48084 STE11 prot...   263   9e-69
CRA|18000004909868  /altid=gi|456309   /def=dbj|BAA05648.1| (D2660...   263   9e-69
CRA|117000066865095 /altid=gi|9857521  /def=gb|AAG00876.1|AC0648...    261   3e-68
CRA|18000005097810  /altid=gi|2342425  /def=dbj|BAA21856.1| (AB00...   261   3e-68
CRA|107000045076103 /altid=gi|12322153 /def=gb|AAG51109.1|AC069...     256   1e-66
CRA|18000005097811  /altid=gi|2342427  /def=dbj|BAA21857.1| (AB00...   253   7e-66
CRA|18000005067450  /altid=gi|4505153  /def=ref|NP_002392.1| MAP/...   240   7e-62
CRA|108000024652142 /altid=gi|12740148 /def=ref|XP_008257.2| MA...     240   7e-62
CRA|18000005037648  /altid=gi|2499641  /def=sp|Q61084|M3K3_MOUSE ...   237   5e-61
CRA|108000000500114 /altid=gi|7542557  /def=gb|AAF63496.1|AF2397...    236   8e-61
CRA|18000005171784  /altid=gi|3688193  /def=emb|CAA08995.1| (AJ01...   235   2e-60
```

EST:
gi|1188786 /dataset=dbest /taxon=9606 ...                            311   7e-82

EXPRESSION INFORMATION FOR MODULATORY USE:
Multiple sclerosis lesions

Tissue expression:
Mixed tissue (Brain, Heart, Kidney, Lung, Spleen, Testis, Leukocyte)

FIGURE 1B

```
   1 MPKPERHAES LLDICHDTNS SPTDLMTVTK NQNIILQSIS RSEEFDQDGD
  51 CSHSTLVNEE EDPSGGRQDW QPRTEGVEIT VTFPRDVSPP QEMSQEDLKE
 101 KNLINSSLQE WAQAHAVSHP NEIETVELRK KKLTMRPLVL QKEESSRELC
 151 NVNLGFLLPR SCLELNISKS VTREDAPHFL KEQQRKSEEF STSHMKYSGR
 201 SIKFLLPPLS LLPTRSGVLT IPQNHKFPKE KERNIPSLTS FVPKLSVSVR
 251 QSDELSPSNE PPGALVKSLM DPTLRSSDGF IWSRNMCSFP KTNHHRQCLE
 301 KEENWKSKEI EECNKIEITH FEKGQSLVSF ENLKEGNIPA VREEDIDCHG
 351 SKTRKPEEEN SQYLSSRKNE SSVAKNYEQD PEIVCTIPSK FQETQHSEIT
 401 PSQDEEMRNN KAASKRVSLH KNEAMEPNNI LEECTVLKSL SSVVFDDPID
 451 KLPEGCSSME TNIKISIAER AKPEMSRMVP LIHITFPVDG SPKEPVIAKP
 501 SLQTRKGTIH NNHSVNIPVH QENDKHKMNS HRSRRITNKC RSSHSERKSN
 551 IRTRLSQKKT HMKCPKTSFG IKQEHKVLIS KEKSSKAVHS NLHDIENGDG
 601 ISEPDWQIKS SGNEFLSSKD EIHPMNLAQT PEQSMKQNEF PPVSDLSIVE
 651 EVSMEESTGD RDISNNQILT TSLRDLQELE ELHHQIPFIP SEDSWAVPSE
 701 KNSNKYVQQE KQNTASLSKV NASRILTNDL EFDSVSDHSK TLTNFSFQAK
 751 QESASSQTYQ YWVHYLDHDS LANKSITYQM FGKTLSGTNS ISQEIMDSVN
 801 NEELTDELLG CLAAELLALD EKDNNSCQKM ANETDPENLN LVLRWRGSTP
 851 KEMGRETTKV KIQRHSSGLR IYDREEKFLI SNEKKIFSEN SLKSEEPILW
 901 TKGEILGKGA YGTVYCGLTS QGQLIAVKQV ALDTSNKLAA EKEYRKLQEE
 951 VDLLKALKHV NIVAYLGTCL QENTVSIFME FVPGGSISSI INRFGPLPEM
1001 VFCKYTKQIL QGVAYLHENC VVHRDIKGNN VMLMPTGIIK LIDFGCARRL
1051 AWAGLNGTHS DMLKSMHGTP YWMAPEVINE SGYGRKSDIW SIGCTVFEMA
1101 TGKPPLASMD RMAAMFYIGA HRGLMPPLPD HFSENAADFV RMCLTRDQHE
1151 RPSALQLLKH SFLERSH
     (SEQ ID NO:2)
```

FEATURES:
Functional domains and key regions:

[1] PDOC00001 PS00001 ASN_GLYCOSYLATION
N-glycosylation site

Number of matches: 11
```
    1    105-108    NSSL
    2    166-169    NISK
    3    369-372    NESS
    4    512-515    NHSV
    5    721-724    NASR
    6    744-747    NFSF
    7    773-776    NKSI
    8    824-827    NNSC
    9    832-835    NETD
   10   1056-1059   NGTH
   11   1079-1082   NESG
```

---

[2] PDOC00004 PS00004 CAMP_PHOSPHO_SITE
cAMP- and cGMP-dependent protein kinase phosphorylation site Number of matches: 4
```
    1    131-134    KKLT
    2    415-418    KRVS
    3    505-508    RKGT
    4    534-537    RRIT
```

---

[3] PDOC00005 PS00005 PKC_PHOSPHO_SITE
Protein kinase C phosphorylation site

Number of matches: 28
```
    1    134-136    TMR
    2    145-147    SSR
    3    365-367    SSR
    4    198-200    SGR
    5    201-203    SIK
    6    248-250    SVR
    7    273-275    TLR
    8    353-355    TRK
    9    504-506    TRK
   10    145-147    SSR
   11    365-367    SSR
   12    366-368    SRK
   13    414-416    SKR
   14    491-493    SPK
   15    353-355    TRK
   16    504-506    TRK
   17    530-532    SHR
```

FIGURE 2A

```
    18    533-535  SRR
    19    537-539  TNK
    20    545-547  SER
    21    556-558  SQK
    22    584-586  SSK
    23    617-619  SSK
    24    584-586  SSK
    25    617-619  SSK
    26    634-636  SMK
    27    672-674  SLR
    28    699-701  SEK
```

---

[4] PDOC00006 PS00006 CK2_PHOSPHO_SITE
Casein kinase II phosphorylation site

```
Number of matches: 30
     1      10-13    SLLD
     2      21-24    SPTD
     3      40-43    SRSE
     4      94-97    SQED
     5     107-110   SLQE
     6     145-148   SSRE
     7     161-164   SCLE
     8     172-175   TRED
     9     268-271   SLMD
    10     319-322   THFE
    11     402-405   SQDE
    12     457-460   SSME
    13     466-469   SIAE
    14     491-494   SPKE
    15     543-546   SHSE
    16     602-605   SEPD
    17     611-614   SGNE
    18     617-620   SSKD
    19     618-621   SKDE
    20     647-650   SIVE
    21     653-656   SMEE
    22     657-660   STGD
    23     672-675   SLRD
    24     734-737   SVSD
    25     834-837   TDPE
    26     849-852   TPKE
    27     901-904   TKGE
    28    1058-1061  THSD
    29    1095-1098  TVFE
    30    1161-1164  SFLE
```

---

[5] PDOC00007 PS00007 TYR_PHOSPHO_SITE
Tyrosine kinase phosphorylation site

```
Number of matches: 2
     1     355-363  KPEEENSQY
     2     937-944  KLAAEKEY
```

---

FIGURE 2B

```
[6] PDOC00008 PS00008 MYRISTYL
N-myristoylation site

Number of matches: 11
    1      76-81   GVEITV
    2     336-341  GNIPAV
    3     507-512  GTIHNN
    4     810-815  GCLAAE
    5     909-914  GAYGTV
    6     912-917  GTVYCG
    7     922-927  GQLIAV
    8     984-989  GGSISS
    9     985-990  GSISSI
   10    1054-1059 GLNGTH
   11    1119-1124 GAHRGL
------------------------------------------------------------

[7] PDOC00009 PS00009 AMIDATION
Amidation site 1083-1086 YGRK
------------------------------------------------------------

[8] PDOC00100 PS00107 PROTEIN_KINASE_ATP
Protein kinases ATP-binding region signature 906-928 LGKGAYGTVYCGLTSQGQLIAVK
------------------------------------------------------------

[9] PDOC00100 PS00108 PROTEIN_KINASE_ST
Serine/Threonine protein kinases active-site signature 1021-1033 VVHRDIKGNNVML
------------------------------------------------------------

[10] PDOC00363 PS00339 AA_TRNA_LIGASE_II_2
Aminoacyl-transfer RNA synthetases class-II signature 2

1106-1115 LASMDRMAAM
```

Membrane spanning structure and domains:
Candidate membrane-spanning segments:
```
  Helix Begin   End   Score Certainty
    1    972    992   1.022 Certain
```

FIGURE 2C

BLAST Alignment to Top Hit:

```
>CRA|147000022596359 /altid=gi|10439647 /def=dbj|BAB15538.1|
      (AK026727) unnamed protein product [Homo sapiens]
      /org=Homo sapiens /taxon=9606 /dataset=nraa /length=168
      Length = 168

Score =  357 bits (907), Expect = 4e-97
Identities = 167/168 (99%), Positives = 167/168 (99%)

Query: 979  MEFVPGGSISSIINRFGPLPEMVFCKYTKQILQGVAYLHENCVVHRDIKGNNVMLMPTGI 1038
            MEFVPGGSISSIINRFGPLPEMVFCKYTKQILQGVAYLHENCVVHRDIKGNNVMLMPTGI
Sbjct: 1    MEFVPGGSISSIINRFGPLPEMVFCKYTKQILQGVAYLHENCVVHRDIKGNNVMLMPTGI 60

Query: 1039 IKLIDFGCARRLAWAGLNGTHSDMLKSMHGTPYWMAPEVINESGYGRKSDIWSIGCTVFE 1098
            IKLIDFGCARRLAWAGLNGTHSDMLKSMHGTPYWM PEVINESGYGRKSDIWSIGCTVFE
Sbjct: 61   IKLIDFGCARRLAWAGLNGTHSDMLKSMHGTPYWMVPEVINESGYGRKSDIWSIGCTVFE 120

Query: 1099 MATGKPPLASMDRMAAMFYIGAHRGLMPPLPDHFSENAADFVRMCLTR 1146
            MATGKPPLASMDRMAAMFYIGAHRGLMPPLPDHFSENAADFVRMCLTR
Sbjct: 121  MATGKPPLASMDRMAAMFYIGAHRGLMPPLPDHFSENAADFVRMCLTR 168 (SEQ ID NO:4)

>CRA|18000005192474 /altid=gi|4028547 /def=gb|AAC97114.1| (AF093689)
      MEK kinase alpha [Dictyostelium discoideum]
      /org=Dictyostelium discoideum /taxon=44689 /dataset=nraa
      /length=942
      Length = 942

Score =  271 bits (685), Expect = 4e-71
Identities = 129/287 (44%), Positives = 196/287 (67%), Gaps = 14/287 (4%)

Query: 879  LISNEKKIFSENSLKSEEPILWTKGEILGKGAYGTVYCGLTSQ-GQLIAVKQVAL-DTSN 936
            +I+  +++ S  ++K      W KG+ILG+G YG+VY GL    G+L AVKQ+ + D ++
Sbjct: 155  IINEHEELISNHNIK------WQKGQILGRGGYGSVYLGLNKDTGELFAVKQLEIVDINS 208

Query: 937  KLAAEKEYRKLQEEVDLLKALKHVNIVAYLGTCLQENTVSIFMEFVPGGSISSIINRFGP 996
                +     +E++++++L+H NIV YLGT L ++ +S+F+E++PGGSISS++ +FG
Sbjct: 209  DPKLKNMILSFSKEIEVMRSLRHDNIVRYLGTSLDQSFLSVFLEYIPGGSISSLLGKFGA 268

Query: 997  LPEMVFCKYTKQILQGVAYLHENCVVHRDIKGNNVMLMPTGIIKLIDFGCARRLAWAGLN 1056
              E V   YTKQILQG+++LH N ++HRDIKG N+++   GI+KL DFGC++  +++G+
Sbjct: 269  FSENVIKVYTKQILQGLSFLHANSIIHRDIKGANILIDTKGIVKLSDFGCSK--SFSGI- 325

Query: 1057 GTHSDMLKSMHGTPYWMAPEVINESGYGRKSDIWSIGCTVFEMATGKPPLASMDRMAAMF 1116
                  KSM GTPYWMAPEVI ++G+GR SDIWS+GC + EMAT +PP +++  +AA+
Sbjct: 326  ---VSQFKSMQGTPYWMAPEVIKQTGHGRSSDIWSLGCVIVEMATAQPPWSNITELAAVM 382

Query: 1117 YIGAHRGLMPPLPDHFSENAADFVRMCLTRDQHERPSALQLLKHSFL 1163
            Y A  +P +P H S+ A DF+ +C  RD  ERP A QLLKH F+
Sbjct: 383  YHIASSNSIPNIPSHMSQEAFDFLNLCFKRDPKERPDANQLLKHPFI 429 (SEQ ID NO:5)

>CRA|18000005097809 /altid=gi|2342423 /def=dbj|BAA21855.1| (AB000797)
      NPK1-related protein kinase 1S [Arabidopsis thaliana]
      /org=Arabidopsis thaliana /taxon=3702 /dataset=nraa
      /length=376
      Length = 376

Score =  263 bits (666), Expect = 7e-69
Identities = 135/283 (47%), Positives = 192/283 (67%), Gaps = 11/283 (3%)

Query: 890  NSLKSEEPILWTKGEILGKGAYGTVYCGLT-SQGQLIAVKQV--ALDTSNKLAAEKEYRK 946
            N++   PI W KG+++G+GA+GTVY G+    G+L+AVKQV  A + ++K     +  +
Sbjct: 59   NTVDMAPPISWRKGQLIGRGAFGTVYMGMNLDSGELLAVKQVLIAANFASKEKTQAIIQE 118

Query: 947  LQEEVDLLKALKHVNIVAYLGTCLQENTVSIFMEFVPGGSISSIINRFGPLPEMVFCKYT 1006
            L+EEV LLK L H NIV YLGT   +++T++I +E+VPGGSISS++  +FGP PE V    YT
Sbjct: 119  LEEEVKLLKNLSHPNIVRYLGTVREDDTLNILLEFVPGGSISSLLEKFGPFPESVVRTYT 178

Query: 1007 KQILQGVAYLHENCVVHRDIKGNNVMLMPTGIIKLIDFGCARRLA-WAGLNGTHSDMLKS 1065
            +Q+L G+  YLH + ++HRDIKG N+++    G IKL DFG ++++A A + G      KS
Sbjct: 179  RQLLLGLEYLHNHAIMHRDIKGANILVDNKGCIKLADFGASKQVAELATMTGA-----KS 233

Query: 1066 MHGTPYWMAPEVINESGYGRKSDIWSIGCTVFEMATGKPPLASM-DRMAAMFYIGAHRGL 1124
            M GTPYWMAPEVI ++G+    +DIWS+GCTV EM TGK P +       +AA+F+IG +
Sbjct: 234  MKGTPYWMAPEVILQTGHSFSADIWSVGCTVIEMVTGKAPWSQQYKEVAAIFFIGTTKS- 292
```

FIGURE 2D

```
Query:  1125  MPPLPDHFSENAADFVRMCLTRDQHERPSALQLLKHSFLERSH  1167
              PP+PD   S  +A DF+   CL      + RP+A +LLKH F+   H
Sbjct:  293   HPPIPDTLSSDAKDFLLKCLQEVPNLRPTASELLKHPFVMGKH  335 (SEQ ID NO: 6)

>CRA|18000005097808 /altid=gi|2342421 /def=dbj|BAA21854.1| (AB000796)
    NPK1-related protein kinase 1L [Arabidopsis thaliana]
    /org=Arabidopsis thaliana /taxon=3702 /dataset=nraa
    /length=661
        Length = 661

Score =  263 bits (666), Expect = 7e-69
 Identities = 135/283 (47%), Positives = 192/283 (67%), Gaps = 11/283 (3%)

Query:  890   NSLKSEEPILWTKGEILGKGAYGTVYCGLT-SQGQLIAVKQV--ALDTSNKLAAEKEYRK  946
              N++     PI W KG+++G+GA+GTVY G+      G+L+AVKQV    A +  ++K    +    ++
Sbjct:  54    NTVDMAPPISWRKGQLIGRGAFGTVYMGMNLDSGELLAVKQVLIAANFASKEKTQAHIQE  113

Query:  947   LQEEVDLLKALKHVNIVAYLGTCLQENTVSIFMEFVPGGSISSIINRFGPLPEMVFCKYT  1006
              L+EEV LLK L H NIV YLGT   +++T++I +EFVPGGSISS++  +FGP PE V    YT
Sbjct:  114   LEEEVKLLKNLSHPNIVRYLGTVREDDTLNILLEFVPGGSISSLLEKFGPFPESVVRTYT  173

Query:  1007  KQILQGVAYLHENCVVHRDIKGNNVMLMPTGIIKLIDFGCARRLA-WAGLNGTHSDMLKS  1065
              +Q+L G+  YLH +  ++HRDIKG N+++    G IKL DFG ++++A   A + G        KS
Sbjct:  174   RQLLLGLEYLHNHAIMHRDIKGANILVDNKGCIKLADFGASKQVAELATMTGA-----KS  228

Query:  1066  MHGTPYWMAPEVINESGYGRKSDIWSIGCTVFEMATGKPPLASM-DRMAAMFYIGAHRGL  1124
              M GTPYWMAPEVI  ++G+    +DIWS+GCTV EM TGK P +            +AA+F+IG   +
Sbjct:  229   MKGTPYWMAPEVILQTGHSFSADIWSVGCTVIEMVTGKAPWSQQYKEVAAIFFIGTTKS-  287

Query:  1125  MPPLPDHFSENAADFVRMCLTRDQHERPSALQLLKHSFLERSH  1167
              PP+PD   S  +A DF+   CL      + RP+A +LLKH F+   H
Sbjct:  288   HPPIPDTLSSDAKDFLLKCLQEVPNLRPTASELLKHPFVMGKH  330 (SEQ ID NO: 7)

Hmmer search results (Pfam):
Scores for sequence family classification (score includes all domains):
Model      Description                                      Score    E-value  N
--------   -----------                                      -----    -------  ---
PF00069    Eukaryotic protein kinase domain                 291.2    1.3e-83  1
CE00022    CE00022 MAGUK_subfamily_d                         29.9    9.9e-09  2
CE00031    CE00031 VEGFR                                     16.6    4.3e-05  1
CE00359    E00359 bone_morphogenetic_protein_receptor         2.5       5.1  1
CE00203    CE00203 ERBB_RECEPTOR                              0.9       6.7  1
CE00292    CE00292 PTK_membrane_span                        -15.3    2.9e-08  1
CE00287    CE00287 PTK_Eph_orphan_receptor                  -28.6    2.1e-06  1
CE00291    CE00291 PTK_fgf_receptor                         -30.1     6e-07   1
CE00286    E00286 PTK_EGF_receptor                          -46.4    2.5e-08  1
CE00289    CE00289 PTK_PDGF_receptor                        -69.1      0.53  1
CE00290    CE00290 PTK_Trk_family                          -110.1    7.7e-08  1
CE00288    CE00288  PTK_Insulin_receptor                   -168.9    8.9e-06  1
CE00016    CE00016 GSK_glycogen_synthase_kinase            -225.4    0.00034  1
```

FIGURE 2E

```
Parsed for domains:
Model     Domain  seq-f seq-t   hmm-f hmm-t      score  E-value
-------   ------  ----- -----   ----- -----      -----  -------
CE00289   1/1       901   998 ..     1   109 []   -69.1    0.53
CE00022   1/2       999  1033 ..   120   154 ..    16.0 0.00013
CE00359   1/1      1021  1081 ..   272   330 ..     2.5     5.1
CE00022   2/2      1068  1093 ..   188   213 ..    13.8 0.00058
CE00031   1/1      1005  1099 ..  1051  1141 ..    16.6 4.3e-05
CE00203   1/1      1008  1101 ..   848   937 ..     0.9     6.7
CE00287   1/1       901  1161 ..     1   260 []   -28.6 2.1e-06
CE00292   1/1       900  1161 ..     1   288 []   -15.3 2.9e-08
CE00288   1/1       906  1161 ..     1   269 []  -168.9 8.9e-06
CE00291   1/1       900  1161 ..     1   285 []   -30.1    6e-07
CE00286   1/1       900  1162 ..     1   263 []   -46.4 2.5e-08
CE00290   1/1       904  1163 ..     1   282 []  -110.3 7.7e-08
PF00069   1/1       900  1163 ..     1   278 []   291.2 1.3e-83
CE00016   1/1       830  1167 .]     1   433 []  -225.4 0.00034
```

FIGURE 2F

```
   1 GCTGGCTGTG AGAGATGTGG ACCTGTTTGA GAGTCTTGAC ATGTTAACAG
  51 TGTACAAACC TGTGGAAGTT CTGTCCCAGC TCCTAAGGCA TCATGCGTGA
 101 ATATGAGCAG TTAGTCAGCC CAGCTGAAGG GTGTCAATTC AATTGTTATT
 151 TACAGAAATC ACATGTAAAC CGAACACACAA AGCTTCTTTT TTACCCTTTC
 201 CCTCCCTCCC TCCCATCCTT TTCTTTCTTT CTTTTCTTTC TTTCTTTTTT
 251 CTTTCTTTCT CTCTCTCTTT CTTTCTTTCT CTCTTTCTTT CTTTCTTTCT
 301 TTATTTCTCT GTCTCTTTCT TTTCCCTCTC CTTCCTTCCT TCCTTCCTTT
 351 CTCTCTCTCT CTCTTTCTTT CTTCCTTTCC TCTTTTTTAT ACAGGATCTT
 401 GCTCTGTTGC CTAGGCTGGA GTGCAGTGAT GCAATCATAG CTCACTGTGA
 451 CCTCAAACTC CTGGGCTCCA TGGATCCTCC TGCCTCAGCC TCTCGAGTAG
 501 CTGGAACTAC AGGCACATAC CACTATGCCC GGCTAATTTT TAATTTTTTG
 551 TGGAGATGGA GTCCCACTAT ATTGCCCATG CTGGTCTCAA ACCCCTGCCC
 601 TCAAGCTGCT CTCCCATCTT GGCCTCCCAA GCTGTGGAGA TTACAGGCTG
 651 TTTTCTACTA TATATGCCAA ATGCACATGC ATCATCATAA AAGTGACTTC
 701 ACAATTGCAA AGTGATGTGC AGTTTCTAAA ATTTGCTACC TATTATTCTT
 751 ATGATATCTG GCTCTTTGTT TCATTTCTTG AAATGATTAC TGTTCTGGTA
 801 GTTACTGGGA ATGTCAAATA ATTTCTTGAG TATCCAGCTC TCTACCCCCA
 851 AGATATTACT AATTATTTCA GAAAACACTG TCAATGTCTG AAAAGCAATT
 901 TATAATAGTG TTTTCAAGTT ATCTTAAAAT TACTATATGT CAAATGCTCT
 951 TTTAGGAGGG AGGAGATAAA CAATGCACTT TTTTTTTAAA TAAGAGGGTT
1001 AATAAGCAAT CTCTTATGTT ACAATTGCAG TTTCCTAAAG CTGTTACTTA
1051 GTTATCTTGT CATCAAATAA GAACAGATGG CCTGAGCTCT TTCTCAGTAC
1101 TTCATATGAA TTTTGTTTTG AAAAAAAAAG GAGGAGGGAG CTTCAAGAAC
1151 AAAATTATAG TCAAGAATAC AAGATATTGT AAAAGGATCA GTTAGTATAA
1201 TGGAATGAAA AGGGAATTTT GAAGCTACTT CAGCCTAGTG TTGAGAAATA
1251 GTTTGGCCAA TTGATAAAAG TGGAGATTCC TGGGACGTCA TCCCAGAGAT
1301 GTTCAGTAGG TCTGGATTGG GGTCCAGAAT ACTGGAAATC AAGGTATGCC
1351 ACTTGGAGAC ACCCTAATCT AGGCAGATGA GGAGAGGCCC CAATGAGTTT
1401 ATCTTTACTT GTTTTTATGC ACCCTTAAAT AATTATAAAA ATTTTTGTCC
1451 AAAGTTGGGA ATTCTCTGCA AATATGATAA GTGGCTTGCT TAAAGCCATA
1501 TATCAAGGTA GTGGCAACCC CAATTCTCAG TCCTATGCTA TTTCTTTTGA
1551 ATTACAATCT TTGATGAAGA AAAGTCCATA AGAGAATATT ACTGTGGCTC
1601 ATGACACATT ACCCTGTCCC ATAGCAACGA AGAGATTCAA ATTCAAATGT
1651 TTTAGGACAG AGACCATGAT CAACTTGCTC CTTGTCCTAG AATAGGATAA
1701 GTAAAGCAAG TTTCATCATT GTTTCCCTCA CTGTAATCTA TTAATGGGAT
1751 TCTCATCATT TAACTTTGGA TTTCTCTGAG CTGATATCTA ATGCAAGGGT
1801 TCAGTACAAC ATAGAGAGGA TAAGAAGAGA CTTGTGCTGT CATAATAGAG
1851 AGGATAAGAA GAGACTTGTT CTGTTGTAAA TGGTCCTAAG ATCAGCCAGT
1901 TGGGCTTACC AACCACAAAG CCAGGTAAAG AGGAATGAAA AGGCCATGTG
1951 GGGGCTGGGC GCGGTGGCTC ACGCCTGTAA TCCCAGCACT TTGGGAGGCC
2001 GAGGCAGGCA GATCACGAGG TCAGGAGTTC GAGACCATCC TGGCTAACAC
2051 GGTGAAACCC CGTCTCTACT AAAAATACAA AAAATTAGC CGGGCATGGT
2101 GGCGGGCCCC TGTAGTCCCA GCTACTCTGG AGGCTGAGGC AGGAGAATGG
2151 CGTGAACCCG GGAGGCAGAG CTTGCAGTGA GCCGAGATCG CGCCACTGCA
2201 CTCCAGCCTG GGTGACAGAG CAAGACTCCG CCTCAAAAAA AAAAAAAAAA
2251 AAAAAAAAAG GAAAAGAAAA GGCCATGTGG AGAGGCACAC TTTGGTTTTT
2301 ATGACAAGAT TGCTCCACTC ATCCAAGAGA CCATGAAATA AAAGTATCAG
2351 CTTAATTTTA AAGAGAAGAT TCTATGCCAT TCCACCATTT TGAATCATAA
2401 AAGAGCTAGC TGTTAGCATT AGAAAAAAGA AATATCAAAA AAGTCAGCAG
2451 TTAGCTTAAT TATTGAAAAG AAAAAAATCA AGTGAGCTAT TTGGAATGAT
2501 AAGACAATCA TTTATCAAAA TGTTTTAATC CTTATGACTC ATTGAAAAAA
2551 ATTTAAAAAT ATAAAAAAAA ACAACAAAAG ATGTTTTTAT CTTTACTTGA
2601 TTTTATGTAC CCTTAAAGAA TTATAAAAAT TTTTGTCCAA AGTTGGGAAT
2651 TCTCTGCAAA CCTCAGAATG TTTTTAGAAT GGGGATGGGA ATAAAGATAC
2701 ACAGCAAATT CCTTTTATTT AAAATCTTGT AAAATTGTCA TCCTCTATTC
2751 ACACATTTTG AAATCATTAT TATTATCCCC AAACTACATA AGATTACTTT
2801 TTATTTATTT GATGTAAATG TTTCCCTCTC ATATTAGTTT TCTTTTTTCA
2851 ACAGATTCAA CTAAATAAAC TTTAATGTTG ATTCTGTTCT TCCTAGAGAT
2901 CCTAAACTTT GTGATTTTAG TGGAAAATCA GCAATACATT ATGTGTCACA
2951 AATAGAGAGT TCAAAGAAAC AGCAGCTTTT GGACATTTTA ATGAGTTCTA
3001 TGCCAAAACC AGGTAAATAC TTTCACTCCA CATGCATAAT TTCCCAACCC
3051 AAAAATTCCT GTTAGATCTC TTTCTTTTTC TACATCTGTT TGATGGATCC
3101 ATTTAAAGAA ATCAAGTCCA CGGCTATTTA TGGAGCAGTG ACTCTGTACA
3151 AGGCCCACGA CTAGGTGCTC TGGGGGATGC AAAGAAGTCT AACGCAAGGT
3201 TTAAACTTTT GAAAATATAC AGCATGGTCA GGGGCACATC ACATAAGTCA
3251 GAGAGGACTT GCTGTAAACT TGAAAGGGGA AGAGGGACTT ATAGTGGTTC
3301 TTGAAGGCTG GATAACAGTG GGAAGGTTTG ATATAGGTAG GAAAAGAGTC
3351 CAAACAAAGA CAAAGAAACA GCCACAGCAA GAAGTATAAT GAAAAGTGTG
3401 CCACTGAGCA GCGTGTGACT TTGTGAAAGC TGCCTGACTT TATTGTTTGA
3451 TTCGCTTTCT GTTTGAAGCT TCGGGGGCAG AGGACAAAGC TATACCTAAG
3501 AAGGTTTCAT GAAAGAGGTG AGACTTGATC TGACCTTTGA AAAAAGGATG
3551 CAATTTGATT TTGTGGAGCA GAGGCCCCTT GCTGGGAGTG AGCATAGCTT
3601 ATCCCAGGGG CAAACAAGAA ACTAGAACTG AAAGTTCATG TCAGGGAAAA
3651 GAGAAACAGA AGGTCAGATA CATAAAGAAA CTGGGCCCAT GGAGGGGAGA
3701 GCCTTAGATG TCAGGCTGAA GGACATCACT TTTTTTTTTC AATAAAACAG
```

FIGURE 3A

```
3751 ACACTAAAGA ATTTTAAGCC AGAGAATGAT GAAGGCCATG TTTTAGGAAT
3801 ATTAACCTGT TCCTATCGTG TTGGCTACAT CTGAGGGAAA AGGCAGGGAT
3851 CTCTATTAAG AAATTATAGA AGTGCCCATA TGTATGGTGG TAAGAACTAG
3901 GGAATGTGTC CTTGGGTGGG GTGTGAGAGT GAGCCTAAGA GATGCTGGGA
3951 GTGGTGGGTC TAGGAGACAT TGTGAAAGAA CAATTCACAG AACTGCGAGA
4001 TGTGATGTTG ACAGCGGAGA CACAGAGACA ACCGCTGAGA AACTTGAGTC
4051 AAAGATGACT AAATTTTAAG GCCTGGAAAG TGCAGGAGAT GGAAATACAA
4101 CCAACAAAAT GGGAGCACAT TGGAACTTTC AAGTAGCAAG TTTCTGTAGG
4151 ACTGGGCTTG TGGGAAGGA CCGGTTGAAA GGTTAGTTTG GGAGTTCTCT
4201 ACAGAGAGGA GATTGTGAGG ACATGATGGT GGGTGAGGTC ATTGAGGGAC
4251 TGATGAGAGT GAGAAAATTG CAGAGGGCTG AGCCGAGGAG GTGCACCCGC
4301 AGATAGAGAG GAGCGGTGGG GACATCAGGA CTCAGGAAGT GAGAGGAGGA
4351 GGAGAATCAG AAGAGAGTTG CGGGAAGAAA GGAGCAGGAA ACAATGTTAA
4401 ATTGGAAAAG AGATTACAAA GCAGATGTGG TAAGGATGTG AGACGTTTCA
4451 ATGGCAGGAT GTAGGCAGAA GATAGATTGC AGAGAGTAAA GAAGGAAAAT
4501 ATGATGAAGA AATGAAAGT CTGGGTATAG ATCACTTGTT CAATTTTGTT
4551 TCCACTACAA GATAAATGGA GGAGCCACTG AAAGAGGGGG AGTTTTTGTT
4601 GAAAGAAGCC AATGCTTATT AGAAGAAGCC AGGATAGCAG GAGGGGATAC
4651 ATATGAGAGC AATGTCCCTA GGGTACAAAC TGGGAGTCTG CTGTTTGGTG
4701 TTAGGAACTC TGTCCATTTA ATGTGGCTTT AATCACTAGA TAGGAAGTGT
4751 GTTCAGAGGA GCTGAGTGTC TTTGTCCTGG GCAACTATAG AGCAAATGTG
4801 ATTTCCAGCT TATCATTAGG GTTTCACTTA GCAACTTTGC CTACCACAAA
4851 CCATTAATCC CAAACATTTG AAGTGATAAC TGTTGATCGC TATTAATTTA
4901 ACTTCATGAT CACTCCCTTC TACAAACTAA AGAAGAAAGT TTGAGCGATC
4951 TAAATTTTTT AAATTATAGG ATGGTCTTGTA AGGCCCTGTG TTGCTTTGAT
5001 TTCAGTTGTT AGCCAAATTG TGCAGAAATT ATCCTCAATT CCCAAGAAAT
5051 AACTTCAGGG GCTTCAGGGC AGTGCACAGA TTCAGAGAAA GAAAATACAG
5101 TATCGATTGA GCCAGCAATA AGTCTTCAGT ACCCTGAAAA ATACATGGTA
5151 GTTTTTCAGG GTTTAGTTGG AAGAGGCCAA GAAGCATCTC CTAATCTTCC
5201 ACCAGTAGAA GTCTGTAATG ATGGGTCATC CTCAGGAAAC ATGGAAGACA
5251 GATGTCCTTC CTCTGCGCAG CTCTGGAGAA GAGGATTCCC TAACCTTGAA
5301 CTGCTGATGG CTTTAATGGT TAAAAAGTTC TTACTCATGT CCCAGCACCC
5351 TACAGAGGGT TTTGCAATGA CGACGTAGAC ATTAAGTATG AAGTGACTAG
5401 ATTTAAGCTG AACTAAAATC TGACTCTTGT TAAGTTTTAA TTTCTCATAC
5451 AGCTTAAAAT TTGGTGGGTG CTCAGATCAG ATAGGATGAT CGATTCATCC
5501 TAACTCTCTA AAAAATATTT CACTTGCTCA AAATCTCAAA CTACCTGTTT
5551 GATTTTTTTG TCCTTATGTA ATAGCAGTTA CCATCAAAGC CTTAAAAAAA
5601 AATAGTAAGC CATCCACTCC GTGGACTCTT GTCTTCACAT CTCTTCTTGT
5651 GAAAATTAGT GCTTGAAGCT TCATCAGGAT CCCAGACCAC TATTTCAGGA
5701 AAATCTTTGA CAAAATGGAG CTGATTTTAG AACATAGAGC TAGATCTTCT
5751 TTTGAAATTG CTGGAGATGA ATCTTATCAA AACATACTAT TATGTTTCTT
5801 TTGATAGAAA GACATGCTGA GTCATTGCTT GACATTTGTC ATGATACAAA
5851 CTCTTCTCCA ACTGATTTGA TGACAGTTAC CAAAAATCAA AACATCATCT
5901 TGCAAAGCAT CAGCAGAAGT GAGGTAAGAG CCTCCCTTTA AAGAAACAAC
5951 GGACAGCCTA CTCCATCTAC TACTTTATTT GTGTTGCTTG AATACTTCAT
6001 AACACTCATA TATTACAATT TTATTTTTAA GTGTAATCAT AAAAAAGCAT
6051 ATTTGGTAAG ACACTCTTCT GAAAGTTTAA TCTCAGAGCA GTAATTAGCT
6101 AGTAAACTCT GAGACTCATG CATAAGATGT GTGTGTACAC GTGTGTGTGT
6151 GTGTGTGTGT GTGTATGTGT GTGTGTCTTA GTCAGTTCTG GCTGCTATAA
6201 CAAAGTACCA TAGATTGGGT AGCTTATAAA CAGAAATTTA TTTCTTACAG
6251 TCCTGGAAGT CTGAGATCAG GGTGCCAGCA GGTTTGAGTC TGGTGAGGGC
6301 TGTCTTCTGG ACTGCAGATT GCCAACCTCT CATATGCTCA CTTGATGGAC
6351 AGAGAGCTAG CTAGTGCTCT GGGGTCCCTT TTATAAGAGG CACTAATCCC
6401 ATCATGAGGA CTCTACTTTC ATAATCTACC TCCCAAGGC CCTACCTCCT
6451 ACTTGCCATC ACATTGGTAG TTAAGATTTC AACATATAAA TTTTGGTGGG
6501 ACACAAATAT TCAGTTCTTT ACTCTGGGTG AGCGTGCCTG TGTGTGTGTG
6551 TCTATGTGTC TCCAGTACCA CAGAATATTG TTTCAGCTGA ATCCATACTA
6601 AATAATCAAA TGTACCTTCC TTTTTATGTA CATTAATATT GAAAAGGAAG
6651 TCTAGGCTAG CCGTGGTGGT CCACACCTTG TATTAGTCCA TTTCACACTG
6701 CTATAGATAC TACCTGAGAC TGGGTAATTT ATAAACAAAA GAGGTTTAAT
6751 TGACTCAGAG TTCCACATGG CTGGGGAGGC CCCAGGAAAC TTACAATCAT
6801 GGTGGGAGGC AAAGGGGAAG CAGGCACATC TTCACAAGGT GGTAGGAGAG
6851 ACAGAGAGAG TGCAGGGGAA ACTGCCACTT TTAAAACCAT CAGATCTTGT
6901 GAGAACTCCC CCACTATCAC AAGAACAGTA TGGGGGAAAC CGCCCCCATG
6951 ATCCAATCAC CTTCTACAAA GTCCCTCCCT TGACATGTGG GGATTACAAT
7001 TCAAGATTAG ATTTGCTGGG GAACACAGAG CCAAATCATA TCACACCTGT
7051 AATTCCAGCA GTTTGTGAGG CTGAAGATCT GTTGAGGCCA GGAGTTCTGG
7101 ACTGGCATGG GTAACAAAAA GAGACCTCAT CTCTACTAAA AATAAAAAAA
7151 ATTAGCTGGT CATGATGGCA CACGCCTGTA GTCGCAGCTA CTTGGGAGGC
7201 TGAGGTGGAA GAATCACTTG AGCCCAGGAG TTTCAGGCCT CAGTGAGCTA
7251 TGATTGCACC AGTGAACTCT AGCCTGGGTG ACAGAGCAAG ACCCTGTCTC
7301 AATTTTTTAA AAAAGAAAGA GACAGGCACG GTGGCTCACG CCAGTAATCC
7351 CAGCACTTTG GGAGGCCAAG GCAGGTGGAT CGCCTGAGGT CAGGAGTTCA
7401 AGACCAACCT GGCCAACACG GTGAAAGCCC ATCTCTACTA AAAATACAAA
7451 AAATTAGCCA GGCTTGGTGG TGGGCACCTG TAATCCCAGC TACTCAGGAG
```

FIGURE 3B

```
 7501 GCTGAGGCAG GAGGATCGCT TGAACCAGGG AGGCAGAGGT TGCAGTGAGC
 7551 CAAGATTGTG CCATTGCACT CCAGCCTGGG CAATAAGAGC GAAACTCCAT
 7601 TTCAAAAAAA AAAGGAAAAG AAAAGGAGAT CATTAATCTG ATCATATCAA
 7651 ACCCATCACA GGGTACCAAA AAGGAGGTGC CTCCTCGTGG CCCTGGTTAT
 7701 CATTCTGTCT ATGATGAATG ACTTTACAAA AAGTCCCCTA TAGTACAGTA
 7751 ACAGTATTAG TAACAAGCAT TGCAGCCCAT AGAAAACCGT GGAATGAGAC
 7801 CCAAGATGTA CAACAAACTG GCAACAGTGA TTGCCTACAG AGAGAGAACT
 7851 GGAGATGCAA TTTGCACTGT TTACTCATTT GTACCTTTTG AATGTTTATA
 7901 AAAATTAACA TATCCCAAAT AAAGATCCTA CTACTCTATA TTTTATTGGT
 7951 TAAAAAAAAA AGTCCAAAAA ATTTTTTATT TATTTTGAGA TTGGGTCTCA
 8001 TTCTGTTGCC CAGGCCGAAG TGCCCTGGCA TAAACATGGC TCACTGGAGC
 8051 CTCAATCTCC CAGGCTCAAG CAATCCTCCT ACCTCAGCCT CCTGACTAGC
 8101 TGGGACTGCA GGCACATGCC ACCACACCCA GCTAATTTAA AAAATTTTTT
 8151 GAACTCCTAG CCTCAAGCAA TCCTCCTGCC TCGGCCTCCT AAAGTAGTGG
 8201 GATTACAGGC ATGAGCCACC ATTGCCATTT TCTAATTGGA TTATTTGCTT
 8251 TCTAACTGAT AGGTTTAGAG AAGCCTTTAT ATATTCTAGG TATATGCTTC
 8301 ATAAAATATT TTCTCCTAGT CAAGAAAATA ATTTGACTTT TTTTCATCCT
 8351 TTTAATGTTT TATTAAAAAG AAGTTTTAAA TTTTGATAAA AAACAACATC
 8401 CATTTTTTTC TTTATGGATC ATGATTTTTG TGACTAGGAA TTGTTCACCG
 8451 AAGCCCAGGA CACAATTTTA TCCTATGCTG TCTTCTAAAA GATTTATAGT
 8501 TTCACATTTT ACATTTAGAG TCATAATCCA ATTAGAGCTT TTTTTTTTCT
 8551 TTTTTTTTGA GATGGAGTCT CACTTCTGTC ACCCAGGCTG GAGTGCAGTG
 8601 GCACGATCTC TGCTCACTGC AACCTCTGCC TCCCAAGCAA TTTTCCCGTC
 8651 TCTGCCTCCT GAGTAGCTGG GATTAAAGGT GCCCACCACC ACGCCTGGCT
 8701 AATTTTTGTA TTTTTAGTAG AGATGGGGTT TCACCATGTT GGCCAGGCTA
 8751 GTCTCGCATT CCTGAGCTCA GGTGATCTGC CTGCCTTGGT TTCCCAAAGT
 8801 GTTGGGGTTA TAAGTGTGAG CCGCCACGCC CAGCGGAATT TGAGTTAATT
 8851 TTTACAAAGT ACAAGGTTTA GGTCGAGGTA CGTATTTTTG CCTGTTGTTC
 8901 CTCTATCATT TGTTGAAAAG ACCATACTTC CTCCACTGAT TTACTTTCAC
 8951 ATCTTTGTAA AAAAAGAAAG AAAGAAAAAG AAAAAGAAAA AAGATCTGGT
 9001 CCAGGTGCAG TGGCTTATGC CTGTACTCCC AGCACTTTGG GAAGCCAAGA
 9051 CAGTAGGATC ACTTTGTGGG GGCAAGAGTT TGAAACCAGC TTGAACAACA
 9101 TAGCAAGAGC TGTCTCTACA AGAACTTTTA AAAATTAGCT GGGCATGGTG
 9151 GTGTATACCT GTAGTACCTA GCTATACAGG AGGCTGAGGC AGGATAATTG
 9201 CTTGAGCCCA GGAAATTGAG GCCTCAGTGA GCCAAGACCA TGCCACTATG
 9251 CTCCAGCCTG GCCAACAAGA GGCCCAATCC CTTAAAAAAA TATATATGTT
 9301 GAGCTTCTTT CTTCAATTAA ACTACTATCA ATTCTTTTTT TTTTTTTTTT
 9351 TTTTTTTGCT GTTGTTGCCA AGGCTGCTGG AGTGGAATGG CTCGATCTCG
 9401 GCTCACCACA ACCTCCGCTC CCCGGGTTCA AGTGATTGTC CTAACTCAGC
 9451 CTCTGGAGTA GCTGGGATTA CAGGCATGGG CCACCATGCC CGGCTAATTT
 9501 TGTATTTTTA GTAGAGACGG GGTTTCTCTA TGTTGGTCAG GCTGGTCTTG
 9551 AACTCTCGAC CTGAGGTGAT CTGCCTGCCT CGGCCTCCCA GAGTGCTGGG
 9601 ATTACAGGCA TGAGCCACCG TACCCGGCCT AAACTACTAT CAATTCTAAG
 9651 ATGTGTACTT TGCATTTTAA CCTCTTTGAA GTCAGACATC TTAAAATTGT
 9701 CACTGTCAAA TTGGTACCGT TTTGTCATTT TTAGTGGTAC ATAAAACAAC
 9751 AGTGTAGCTT TTAATCAAGG ACATCTTAGA TTTAGTGAAA CATGGTAGGA
 9801 TACATTGCTA AACCCAAGTC ACAATATAAA ATGTCAGAAA GTGGATAGAG
 9851 AAGTGAGAAA TGATTTTGCA GCATGGAGAA TGGTAAAACC TAATTTCCAG
 9901 AGAAAGGATA TTAATGAGAA TCAAGATGAT GTACTGCAAA GAACCATGGA
 9951 AAAGCCCAGG AATTAGAGGC ACCAGGTACT GCAGACGTTG GGAGTTAGCA
10001 TGAGGTTGAA AAACAGGAGG GTTTGGTTGA AAATGTATAT AAGGAGCAGA
10051 GAGATCCCCA ACATTCTACT TCCACTCTAT GTAACTACAT CACTACTCCT
10101 TCCCCACCCT CACAGAAGGC AGGAAGATTT GGTGGAGGAT TATTTGAGCT
10151 GGAGGAATTC TGGACTTAGT AACAACATAC AAAGTGAAAG ATGGGAATCA
10201 GGTCTCAACC TGCAGGCTTA AGTCTGAATA TTGACAGAGA GATTGCATCC
10251 ATCCTCCTTC CCCACCTAGC TCCCATATGG CCAGCAGCCC GTTTATACTA
10301 CTAAGCCAAA AGACTGGAAG ATTCTTTTCT GGAGATTTAA TAACCCCAGA
10351 AAATAAACCT ACCGATACTG ACATTTTTAA GTTCCCTGAA ACACAAGCAT
10401 TTCACCAGAT TAACCCAGCG AAGCCCACCA ACAGGTAAAT AGCAATATAC
10451 ATAGAGAACT TCTAGTCATA TTTTTAGAGT CATATTTTAT CTTCCTTAAT
10501 ATGAAGAGCC AAGATAGCCA AGGGTTATCA GGTATTTGAG GAAAGCCTCC
10551 AATATGAAAA GTAGCATCAA AACAACAAGG AATGCAGATG ACATCAGGAG
10601 CACAAAGAAA TGAAGGGGAA GAAATAGTTT TAAAGGGAGG AGAGAAAAAT
10651 AAAGAAAAAA ATGTTATCAG AACCAAATGA TATGAGTTTT CAAGTTTAAA
10701 GCACCCATCA CTGCAAGACC CATCATTGCA GGACAGTGAC TAAGTACATT
10751 ACCTTAAAGT ATTATGAACT TTTAAAGCAC TGATGCTACA AGAGAATCCT
10801 AAAAGTTTTC AAAGAAAGAG AGAGAGATAA TATAAAGGAT AGGAAACTGG
10851 AATGGCACCA GATGTCTTAA AAATACCATT GTAAGCTACA AATATATGGA
10901 GCTACAAATA TATGGAGCAA TAAAAGACCT CTACACTGAA AGTAGTAAAA
10951 TATTGCTGAA AATTTTAAGA AGACTTAAAT AAATAGAATG ATGTAACATG
11001 TTAGTGGATT GGAAAATTTA CTTTTATAAA GATGTCAATT CTGCCAAATT
11051 CGTTTGTAGA TTCAACACAG TCCCAATCAA AACCTAGCAG GTTTGTGTGT
11101 GTGTGTAAAT TAACAAGCTG ATTCTAAATT CATATAGAAA GGCAAAAGGC
11151 CAAGAATACT GAGGGCAATA TTGAAGAAGA ACAAAGTAGG AAGATTTACA
11201 CTACTAGATA TCACATCCTA TTATAAAGCT AAATCAATTA AGGCAGTGTG
```

FIGURE 3C

```
11251 ATATTGCTAG AAATATAGAT AAATCCATTA CCTGATTTAT GACAAAGTTC
11301 ATGCTGCAGT GAAATAGGGG AAAGAATTTT CAATACATGG TTCTGGGTTG
11351 CATGGATAGT CATATACAAA ACAATATGCA TGTTGACCCC TACCTCACAC
11401 CATATACAAA ATCAATTCCA CATTGATTGG AACAGATCAC TGCAGCCTAG
11451 CATTCCTGAG CCCAAGCAAA ACTCCTGCTT CAGTCTCCTG AGTAGCTGGG
11501 ACTGCAGGCA CATGCCACCA TTCCCGGATA ATTTTTTTCA ATTTGTTTTT
11551 GGTAGAGATG GGGTCTTGCT TTGTTGCCCA GGGTGTTCTT GAACTCCTGG
11601 CTTCAAACAA TGTCCCTGCC TCATCCTCCC AAAGTGCTGG AATTATAGAT
11651 GTGAGCCATT TTGCCTGACC ACACTAACCC TTTTGAAAGA AAATGTAAGA
11701 AAATCTTTGT GACCTTGGAG CTGGCAACAA ATATTTTTTT TTTTTTTGAG
11751 ATGGAGGCTT GCGCTGTTGC CAGGCTAGAG TGCTGTGGTG CAATCTCGGC
11801 TCACTGCAAC CTCCAACTCC CTGGTTCAAG GGATTCTCCT GCCTCCGCCT
11851 CCCGAGTTGC TGGGATTATA AGCATGCACC ACCATGCCCG GCTAATTTTT
11901 GTATTTTTAG TAGAGATGGG GTTTCACTAT GTTGGCCAGG ATGGTCTTGA
11951 TCTCCTGACC TCGTGATCCA CCCACCTCGG CCTCCTAAAG TGCTGGAATT
12001 ACAGGCATGA GCCACTGTGC CCGGCCAACA ATTTTTACAA CAGAACACAC
12051 ATCACAAAAA ATGCTTGCCA TAAAAGAAAA GTTAATTAAA TGGGCTATAT
12101 TAAATGAAGC ATTTCTTTTT ATCTAAAGAC ATCATTAAGA TAATAATAAG
12151 CAACTCATAA GGTGAGAAAA GATACTTAAA ATGTATGTAT CTGACAAAGG
12201 ACCTGCATTC AGAAAAAATT TAAAAACTCC CACAAATTAG GAACAGATAG
12251 GCTAATAGAA AGTGGGCAAA AACTTGATCA GACACTTAGC AAAAAAAAGA
12301 TGTCTAAATG GCCAACAAAA TATATTAAAA GATGCTCAGC TTTTAGTCAT
12351 TAGATAAATG TAATTTTAAA CAACAATGTG ATAACACTGC ACATCCACAG
12401 AATGATTACA ATTTTACAAG TTGGGAAATA TCAAGTGTTG ACAAGGATGT
12451 AGGGCAACAA GAACTTTCAT GCACTGCTGA TGGGAGAATG AACTGTTAGA
12501 ATAATTTAGA AAGCTGTCTT TTGGTGTCTG TTAAAGAGAA ATATATGCAT
12551 ACTCCATAAT CCAGCAATTC TGCTCCTAAA TACATACCTA ACAGAAATGC
12601 ATCATATGTT TACCATAAGC TACATATTAT AATGATCATA GCAGCACTAT
12651 TATAATAGCC CCCAAATGGA AAATACCCAA GTGCCTATCA AGAATAGAAA
12701 GGATACATAA ATTGTGGTAT ATTCACATAG TGTAAAACTA CACATAAATG
12751 AGAATGAGAG TGAATGATCT AAAATTACAT GCAAAATAC AGATGAATCT
12801 CACAAATACA CTGTTGAGCA AAAGAAACCA GACATAAAAA ATTAAATCCT
12851 GTATGGGTCT ATTTATATAA AAACAAAAGG AGGAATAACA AAGCTAATCT
12901 ATGGTGTTAG AATTCAGAAT AGCACTTGCA TGAGAGTGTT CTTTGGGGAT
12951 ATTGGTAGTG TTCTTTTATT TGATCTGGGT CCTGGATACA CAAATGTATT
13001 GGGTTTATTA AAATTAATCT ATACACATAT GGTAAGTGAA CTTTTCTGAA
13051 TGTATGCTAT ACTAAAATCA AAAGTAATGG AAAAGGGGTG GAGTAGGGAA
13101 TGTCTTCAAA TATCTGACAC ACACAAAAAA GAATATGGTT TTCAGCCAGG
13151 CATGGCTGTG GATACCTGTA CCTGTGGTCC CAGCTACTCA GGAGGCTGAG
13201 ATGGGAGGAT AACTTGAGCC CAGGAGTTTG AGACGAGCCT GGACAACATG
13251 CCTTTTTTTT TTCTTTTCTT CTTTTTTTGGA GACAGGGTCT CACTCTGTCA
13301 CCTAGGCTGG GGTGCAGTGG CCAGTGGCAT GATCACAGCT TACTGCAACC
13351 TCCGCCTTCC AGGCTTCAGC AAACCTCCCA CCTCAGCCTC CTAAGTAGCT
13401 GGGATTACAG GCATGCTCCA CCAGGCTCCG CTAATTTTTG CATTTTTTTG
13451 TAGAGATGGG GTTTCACCAT GTCACCCAGG CTGATCTCGA ACTCCTGGCC
13501 TGAAGTGATC TGCCCACCTC AGATTCCCAA AGTGCTGGGA TTACAGATGT
13551 GAACCACTGG CCCGAATGAA TGTGGTTTTC AAACTAGGAT TCTATGCCCA
13601 AACAAACTCT CAGTTAAGCA TTAGAGTTGA ATAAAGACAT TTTTCAGACA
13651 CAGAAATCTC AAACATATTA CTTCTGATAT ACCTTTTAAG GAAGCTACTA
13701 AGTGCTCTAT TAAATTGAAA AAGTAAATAA AGAAAGAGGA AAAAATAGGA
13751 TCTGTGACTC AGAGGATCAA GAGAGAGGAG GGAATCATTG GTATAATGAA
13801 GAAGGCAGGT CCCAGGACTT CAGCTAATTA GCAACTCTAG AAAACAAAGA
13851 GCTCAGATGA TTGGGGGATT GGGGTGGGGG CAGGGAGCAG GACAGAGGAG
13901 GGAAACAGAA CAGATATTGT TGTCTGATAA ATTTCACCAA GTGGCAAGAC
13951 CATTGTAGGT TGGGAAGATT TAGGCTTTAA ATAAAAGGAC ATAAGAAAGT
14001 AAATAAAATA AACCAACTAG AAATTAAAAA ACCAAGGGAT GAGGGGAAGG
14051 AAGGATGAAT AGGCAGAGCA AAGAAGATTT TTAGGGCACT GAAACTACTC
14101 TGTATGATTC TATAATGGTG GATACAGGTC ATTATACATT TGTTCAAACC
14151 CATAGAATGT ACAACACCAG GAGTGAACCT TAATGTTAAC TACAGACAAC
14201 TGTAACAAAT GTACCACTCT GGAGGGCGAT GTTAATAATG GGTGAGGCTG
14251 TGCATGTATG GGAGCAGGGG GTATATGGGA AATCCCTATA CCTTGTTCTT
14301 CTTCTTCTTC TTCTTTTTTT TTTTTTTGGG ACGGACTCTT ACTCTGTCGC
14351 CCAGGCTGGA GCGCGATCTT GGCTCACTGC AACCTTCACC TCCTGGGTTC
14401 AAGTGATTCT TCTGCCTCAG CTTCCTGAGT AACTGGGGTT ACAGGCATGC
14451 ACCACCATGT CTGGCTAATT TTTGTATTTT TAGTAGAGAC AGGGTTTCAC
14501 CATGTTGACC AGGCTGGTCT CAAACCCTTG ACCTTAGGAG ATCCATCCAC
14551 CTTGGCCTCC CAAAGTGTTA GGATTACAGG CGAGAGCCAC TGTGCCCGGC
14601 CTATACCTTC CTCTTAATTT CTCTGTGAAC TTAAAATGTC CCTAAAAATA
14651 AAGTCTATTC AAACAAACAT ACAAACAAAC AAACAAACAA ACAAGGGTTT
14701 GGGGGTTTGT TCTGGAAAAT AAAACAGTTA TACAAGAAAG AAAGCATAAT
14751 CATACTATAT TACAATTGTA CTACTACATA GTACAATATC CTCATAATCA
14801 AAATTAGCCA TTGACTATTG ATTTAACAGC AAAGAAGGTA AATGTATTGG
14851 GAGGATGGAG GCAGGGCATA AGAACATTAA ATTATTAACT GCCATAATAA
14901 GTCAATAGAT GATGCCTCAC TTTGATGAAT CAAGAGACAG CATGATAACT
14951 ATGCAGAAAT ACGGAAGAAA ATACCAAAAG AAACAGCTAA AAGTTTGGAA
```

FIGURE 3D

```
15001 GTGGTTGCCT CTGAGGAAAA CGGTGACTGT TTTTCTCGGT ATAAGTCTTT
15051 TACCATTATT TGATTTTTTT TACATGTGCA GTTTAATTTT GATAAAAATT
15101 AAGTGAAAAT TAAAAAATAAA CGGTTAAATC AAGACTTCTC TGGGACATGG
15151 GATGGGATGA GCTACCATGG AAACATTCCT TTTTAAATCC TATTTGAATA
15201 TTTTAGCTTT GCGCATTTAT AAATTTTCTA AGTAGTTTAG TCTGCTTCCT
15251 ACCAAAGTGG AATTTAGTAC CCTGGTTCCC AACAAGGGAG TGATTCCCAG
15301 CGCCCACCTC CCACCCCTCC CACCCTAGGG GGTCATTTGA CAATGTTTGC
15351 AGACATTTCT GGTATCATCA CTAGGGGAGA ATGCAACTGG CATCTTGTGG
15401 GTACAAGCCA GGGACGCTCC TAAACATCCT ATCAGACACA CGACAGCCCC
15451 CACAGCCAAG AATTATCTGG TCTTGAATGT CAACAGTGCA GAGACTGAGA
15501 AATTTGCTAC ATGTTGTCAC AATATTGAAG GTTGCACTGT GTTTGGTTAC
15551 TAATATTATA TAGTAATCAA AATAAAATAC CTAGAGACAA ATCTTTAAGG
15601 TGAGTGTCAT GCATAAGATA TTGATAAACA AAAACATACT TTTTATTTTT
15651 ATGGTCTATT TAAGCAATTT TCTTTTTAAA AGGACTAACT ATATCACTTC
15701 ATATTAATAC ATTGAAATAA ATGTTTAAAA ACATTTTTGT AGAGATGGGG
15751 TCTCACTATG TTGCCCAGGC TGGTCTCAAA CTCCTGGCCT CAGCCAGGTG
15801 TGGTGGCATG CACCTGTAGA ACCAACTACT TGGGAGGCTG AGGCAACAGG
15851 ATCATTCAAG CCCAGGAGTT CAAAGTTACA GTGAGCTATG ATCACACCAC
15901 TGCACTCCAG CCAGGATGAC AGAGGGAGAG TCTGTTTCTA AAAAACAAAC
15951 AAACAAACAA ACAAACAAAC AACATCAAAC TCTTAGTCTC AAGAGATTCT
16001 CCCACTTCTG TCTCCTAAAG TGCAGGAATT ACAGGTGTGA GCCACCGTGC
16051 CTGATCAGTA CATTTTTTGA GGCAACTTTA AGACTTTTTT TTTTTTTTTT
16101 TTGAGACAGA GTCTCGCTCT GTCGCCCAGG CTGGAGTACA GTGGCGCGAT
16151 CTCGGCTCAC TGCAAGCTCC GCCTCCCGGG TTCACGCCAT TCTCCTGCCT
16201 CAGCTTCCCG AGTAGCTGGG ACTGCAGGGG CCCGCCACTA CGCCTGGCTA
16251 ATTTTTTGTA TTTTTAGTAG AGACGGGGTT TCTCCGTGTT AGCCAGGATG
16301 GTCTCGATCT CCTGACCTCG TGATCCACCC GCCTTGGCCT CCAAAAGTGC
16351 TGGGATAACA GGCGTGAGCC ACCGCGCCTG GCAAAACTTT TTTTAAAAAC
16401 CTTTCATTAG GTGTTTTTTC TTATTGTAGC CGAAATAAAG TTTAAACTCC
16451 TTTTTGAGGG AGAAATGGAC TTTTTCAGTA TTATATTTGC CTTTCCTTCC
16501 CTAGTGGTTT AACTGGGGTT TAAATCCCTT TCACTCTTTT CTTTAAATGA
16551 AAGCTTTGTT TTCTTTTTGG TTGTCTGAAA TAGGTTTTTA TAGTTTACAA
16601 ATATAAGCAG CTGCCTTGCA TGTAGGACAG CTCCAGAGAG GCTCGTTATA
16651 GACTCGCCCA GTCATCTTTT TTCACCTGAG GAGAATCTTC TTTCAAAATT
16701 TTATCATAGG CTGGATATGG TGGCTCATGT CTGTGATCTC GGCACTTGGG
16751 GAGGCTGAAG TGGGAAGATC CCTTGAGTCC AGGCATTCGA GACACCCCTG
16801 GGCAACATAA TAAGACTTTG TCTCTACAAA AAAATTAAAA AATTAGCTGG
16851 TTATGGGGGC GTGCCTCTGT AGTTCCAGTT ACTTCCTGGA GGCTGAGGTG
16901 GGAGAACCAC TTGAACACAG GAGTTTGAGG CTGCAGTGAA CTATAATTGT
16951 GCTGCTGCAT TCCAGCCTCG GCGACAGAGT GAGCTCCCAT GTCTCTAAAA
17001 TATAAAAATA AAAAAACTTT AATCACGTCT GATTTCCATC GTGCCTTTAC
17051 ATTCTGTATG TTTGGTATGC TGTTGTCTGC AGGCTAGAAT GCGATGCTCT
17101 ATTTCTTATC CATCTATCAG CTCCCGTGGT GTTGTCAATG GTTTATGAAA
17151 TCCATCTATG TTTGGGACTT GCTATTCTGA TGTTTTCTCT CTTTTACTCA
17201 CTCCTAGATG ACACTATTTC AATTCTCCTC CTTGTGGCAC CCAAGCACAT
17251 CTTAAAGTCA TTGCTGGTTA GATTTATAAA ATAAGTTAGA AAATTCTGAG
17301 CTGTTTCTGT TTGAGTCTTC ACTTCCGTCA TCACCTTCAA AGTAGATCTT
17351 ACTCCCTACA TCCTTTTTGA TTGTGATACT TATGGTTTTT CAGTTTGTTC
17401 CAGGGTTTAA ATTTTTGTCA GGTACTTATA GGGATCACAC ATCTTTTATT
17451 ATTATTTTTT CTATGCAAAA CTTATCAATT AGGTTTGAGT ATCCTTTCCC
17501 TTTATTTTGC TCATTAAATTC TTTTTTTTTT TCTGGTTCTT GTTGAAATTC
17551 ATTGTTTCAA ACTTTTCATG CTAACAAGAT CACTGAGTGG TCACAACCTC
17601 TGGACCCAGA TTTCACAGTC TGGGTGTAAA TTCTGGCTCT GCCACTGGCT
17651 AGCTGTGTGA CCTCGTGTAA GCTACTTAAC TTTTCTGGGC CTCAGGTACA
17701 AAATGAAGAT AATAGATCCT AACTTTTAGAG TTGTGAGGAT TAAATTAGTT
17751 AACCCATTTA TGCTTAGTGT TCCATTATTG GAACGGTGAG CTTGTGGGGG
17801 TTATTTATAT CCCACTGCTC AAGGTCATTG CCAAGGTCTG ATTTTTCACA
17851 CAAAAAAATT TGCAACCTCC GAGATAAATG GGTTAATATG TGTAACGCAT
17901 ATAGAACAGT GTCTGGTACT ATATATGTAA ATGCTAGTCA TCATTATGGA
17951 TTTTGTAGGT GGGTATGACC ACACTGCCGG CTTCCAACTT TTCCTACAGG
18001 ACCAACTGAC AAATGAACTG AGTAGCTGAG ATTGACCACA GCCCAGTAAT
18051 CAACATGGAA ACTTGATGTG AGAACCTGCT GTATGACTAA CACTTCCAAA
18101 TGAAGGCTGC TGTTTTCTCA AAGCTCAGCA TAAAAATTTC ACTGAATCAC
18151 TGTAATTAAA TGAAATGGTT GAAATGTGTT TTGAGGTCTC TTAGAGTGTT
18201 CTAGACTAAG GATCTACACA AAAACTATAT ATAATACTAA AAAAGAAAAA
18251 TTCAAATGAC CCATAAGCAT CTAAAACTAT CTCCAACTTT TCTATTAATC
18301 AAAGTATGAA CATTCAAACA ATAATAAGAA GACCAATTCC ATCTATTACA
18351 TTAAATATAA TAAAATGAAA AGTCGGCCAG ACGTGGTGGC AGGTGCCTGT
18401 AATCCCAGCT CTTTGGGAGG CAGAGGGAGG TGGATTACTT GAGATCAGGA
18451 GATCGAGACC AGCCTGGTAA ACATATTGAA ACGCCATCTC TACTAAAAAT
18501 ACAAAAAAAA AAAAAAAAAA TTAGCCAGGC ATGGTGGTGG GCACCTGTAA
18551 CCCCAGCTAC TTGGGAGGCT AAGGCAGGAG AATCGCTTGA ACCTGGAAGG
18601 TGGAGTTTGC AGTGAGCCGA GATTGCACCA CAGCACTCCA GCCTGGGCAA
18651 CAGAGCAAGA CTCTGTCTCA AAAAATAAAA AATAAAATGA AAAGGGGCAG
18701 GGCATGGTGG TACATACTTA TAGTTCCAGC TACTCAGGAG GCTGAGGTGG
```

FIGURE 3E

```
18751 GAGGATCACC TGAGCCCAGG AGTTCAAGGC TGCAGTGAGC CATGATAGTG
18801 CCACTGCATT CCAGCCTGTG TGCCAGAGTG AGACACTGCC TCAAAATAAT
18851 AACAATAATC ATATAAACAC CTGTGAAAAG AAGGGAAAAC AATAATAATT
18901 AATTAATTAA TTAAATGAAA AGGAATGATG ATAAGGGAGA AGATATGATA
18951 TAGCACATTC ATGCACTGCT GGTGGATTAT AAATAGGGAT AAACTTTACT
19001 TTTAAGGCAA TGTGTGTACA AAAAAACAAC TTTTTCATAG TATTTGGGTC
19051 AATAATTCCA TATCTAGGGA TCTACTCTAA AGAAATAATG CAAAATTGGG
19101 GTATTAGTTG CAAATATTTA ATAATACTAT GTGTAAGAGT GAAGAATTTT
19151 AAATTACCTA CTAAGCATCA TGGGAGTTAC ATTGTAAGAC TAACGGGGCT
19201 TATTAAAGAA GTACTATTGG CTGAGCGTGG TGGCTCACGC CTGTAATCCC
19251 AGCACTTTGG GAGGCCGAGG CAGGCAGATC ACGAGGTCAG AAGTTTGAGA
19301 CCAGCCTGGC CAGCATGGTG AAACCTCGTC TCTACTAAAA ATACAAAAAT
19351 AAGGCGGGCA TGGTGGCGGG TGCCTGTAGT CTCAGCTACT CGAGAGGTTG
19401 AGACAGGAGA ATCTCTTGAA CCCGGGAGGT GGAGGTTGCA GTGAGCTGAG
19451 GTCGCACCAC TGCACTCCAG CCTGGGCGAC AGAGCAAGAC TCCATCTCAA
19501 AAAAAAAAAA GAAGTACTGT TATGACCCTC TGATATTTGT TGAAGGAAAG
19551 AAATTTTAAA TTCCATTAAA ATTAAAATGA CACTTACTTA GTAAATTGCT
19601 TATGAATTTA CACTTAAGTG AAAAAGCCAG ATACAAAAAT TATGTGATGC
19651 AACTATATTT TTAAATACTT AAGAGAAACA CAAAGAAAAT ATGATTCCTG
19701 TGTTAACAGT GTTTGCTCTT TGGTTGTCAG GTTATAGGTG ATTTTTTAAA
19751 TTTTGCTTTA AAAAATACTT TTTTGTATTT TTGTATGTTC TAGGAAGAAT
19801 AAATCCCCCT TTGTGATTTG ATAGGAAGGA GGAGGAATTT GCCAGATAAT
19851 GGTAGAATTT TTGAAATACA GAGAAGGTTA AGCAGTGAAA TTGACAACAG
19901 CCTAGGAGCT GAGTGAACCC ATCCGCCATT GACAACCAGG ATAGTCTGAG
19951 GTAGGGCACC CAACTTTTGC CAGGAGATAG AAAACGCTTT AGAAAGTATT
20001 AATAAGGGTA GTGGGGAGTA GGGAGGAAGG GGGATGGTTA ATGGGTACAA
20051 AAAAAAATAG CTAGAAAGAA TGAATAATCA ACCCAATGAG AGAACAAAAA
20101 GAAAAAAAAA GGAAAAGAAA GAGTAAGAAC TAGTACTGAT AGCACAACAG
20151 GGTGACTATA GTAATAATTT AATTGTACGT TTAAAAATAA CTAAAGTAT
20201 AATTGAATCA TTTGTAACAC AAAGGATAAA TGCTTGATGT GATGAATACT
20251 CCATTTACCC TGATGTCATT ATTATGCATT GCATGCCTAT ATCAAAATAT
20301 CTCCTGTATC CCATAAATAT ATATACCTAT GTACCCATAA AAATTAAAAA
20351 ACAATGTTTA AGTATAAACT GCTGAATAAA AGTAAGGTAT GACAACTAAG
20401 TTATTATGAT TGAATACCTA AAATATTTTT AATGACTGTA TAAATGGAGG
20451 GTTTTACTTC TGGTTTTTTT TTTTGAGACA GGGTCTCACT CAGTTGCCCA
20501 GGCTGGAGTG CAGTGGTGCA ATCATGGCTC ACTGCAGCCT CAACCTCCTA
20551 TGGCTCAAAT GATCCTCGCA CCTCAGCCTC CTGAGTAGTT GGGACTACAG
20601 GCACGTGCCA CCATGCCTGG CTAATTTTTG TATTTTTTGT AGAGATGGGG
20651 CTTCACCATG TTGTCCAGGC TGGCCTCAAG CAATCCACCC ATCTCGGCCT
20701 CCCAAAGTGC TAGGATTATA GGTGTGACTC ACCATGCCTG GCCAGGTTTT
20751 ACTTTTATTT CCTTTTTCTT TTCTTCTTCT TTCTTTTTT CTCTCTCTCT
20801 CTTTCTCTCT CTCTTTTCTT TTCTTTCTTT TGACAGGGTC TCACTCTGTC
20851 ACCCAGGCTG GAGTGCAGTG GCGTGACCCT AGCTCACCAT AGCCTTGACC
20901 TCCCGGGTTC AAGCCATCCT CCTGCCTCAG CCTGCCAAGT AGCTGGGACA
20951 ACAGGGGTGT GCCATCACGT CCAGCTAATT TTTGTATTTT CAGTAGAGAC
21001 AGGGTTTTGC CATGTTGCCC AGGCTGGTCT CGAACTCCTG AGCTCAAGTG
21051 ATCCACCCGC CTCAGCCTCC CAAAGTGCTG GGATTACAGG AGTGAACCAC
21101 CATGCCTGGC CAACTTTTAT TATTTGCTAC GACAATTAAA ATGAACAAGG
21151 AGAGAAAAGC AAGAAATTTC CTAGCTCTCT TGGGAATTAA TAAATGAGCT
21201 ATCAGAGAAT TTTTGTGACT CGCCACTTCT CTGACATTTC AGATGACAGG
21251 CTTGAGCACT TAGGGCAAAG ACTTATTGTC CATCAGTCCC CTTAAATAGG
21301 TAGTCCACCT AGATCATAGA AACCAGACAG ATAGTTGTAA CATTCGGGTT
21351 GTGATGGGAT GTTTTAACTA TTACTTGGAT CTATCATGGT TCTAGAAATT
21401 TAAAGGCACA AAATCATCAG CTATAACTTC GAATGAAGGA AACTATCAAA
21451 AACAATGAAT TCTACTAAGA AAACATTTCT TCTTTAAAAT GTTTGGAGTA
21501 CTTTTTTGTAA ATCAAGTTGG TTTTCAACTA TAATGATTAT TTTCTAGAGA
21551 GTGAAAAGGA AGTTTAAGAG GTTATGCACC ATGATTTAGA TCAGAACGCC
21601 GTCATAGGGA AGACTTTAAT CAGCTTTGCT GCCTCCTTTC AGTCTAGGGT
21651 TATATCTGTA GCTTCCACAG GGGCAGGGAT TTCCATTCTT GCCATATGTA
21701 AATGATGCCC CAGGGAGGCA TTATGGAAAA GATCATGCTC CTTTGGGGTT
21751 GTTCACTGTG ACTGTGGCCA AAGGATTCTT TCCAGTTACC TACCCAGATG
21801 GAATTTGGGG CAGCTTAGCA GCCTGGGCAC TGAGATGATA AAGTATAAAA
21851 TACTGAGTTT CTATGTGTCG ATGTGATTTC AGCTTTGCTC CTCATTTTTG
21901 ATTATGCAAT TAATCACAAC CATGACTGTC TGAGCCTAGT GCTCCAAGGG
21951 CAGATACTTT CTTATTATTT TAGTCCTAAA TACTTTATCC AATTTAAAAG
22001 GAATCCATGG TGTAAATCTT TAGCCCAGAA AAATCAACAT TCACTCTGCC
22051 AACAAACTGG TACATCGAAT AACTAATAAC TGAGTTTTGA ATTTTATGAT
22101 ATTGCAGGAG TTCGACCAAG ATGGTGACTG CAGTCATTCC ACACTGGTTA
22151 ATGAAGAAGA AGATCCCAGT GGTGGTAGAC AGGACTGGCA ACCCAGGACA
22201 GAAGGTACTG GGCTTTACTC CTTGATGTGT TTACAAAGAT AACATTATCA
22251 TATGGGCTTC TCTCCAATTT CAGAAGGGCT TATTGTAGAA GTTTGAACAA
22301 CATACACTGG AGCCTATCAG AGGGTAGAGG GAGTGGAGGA GGGAGAGGAT
22351 CAGGAAAAAT AATTAATGGG TACTAGGCTT AATACCTGGG TGATAAAATA
22401 ATTTGTACAA CAAACCCCAT GATACATGTT TACCTATGGA ACAAACCTGC
22451 ACTTGTACCC CTGAGCTTAA CTCTTGCAAT AAAAGTTAAA AAAATTATAA
```

FIGURE 3F

```
22501 TAAATAAGTT TGAAAACACA GAAAAAGCCC AAAGGAGAAG AAAAACCACT
22551 CACAATACTA CCTTTTGGTC CATATCTGAA TCAGTGGGTC TAGGCAGCTT
22601 GACTGGCCAG AATAGGCAAA TGCTCTCTGG CTCTTTTATT CCACCTCACT
22651 CCAGCTCAGC CGACCCATTC CCTGTCCATT TCTTTTTGTC TGATAACATC
22701 CTTTCCCCAA TTTCTTCCTC TCAGAATCTT CCAGCGGCTT CAGTGATCGG
22751 TTCCCTTCCG GAACCACACG TGTCTCCATG AGCCGTTGTC CCTGAGGGGA
22801 AGGTGGGGGA GTGTACGAGA CCTGAAAGTC CCCAAGTCTC GGTCTTTTAT
22851 TTACAAGGCC ATAAGTCTGG AATCTTCCAG AACACCACCC ATTTCAAACA
22901 TGTTATCCTG TCACACCGTA AGTGCCCTTG CACTTAACAG ACCACAAGGT
22951 ATTTGCAGAT TCTCGCCTCA GAGCATAGTT GCCACGGCTA TCCCATTTGT
23001 CTGTCATCTA TTCATCCATA ACCTTCTTAA AGTAAATGTT TATTTGAACT
23051 GCTGCAATTT CTCCCGGGCA ATCTTCTGGC TTCTATTTCT AGCACTCCAG
23101 GGAAGCCGCC CTCTTTGATG CCCGTGTTTC TCATCCCTTC GCACCTCTCA
23151 GAAGGCTGCA GCTCTCCCGA GTAGCGTCTC CTCCGGGAGG TGGTGCGATG
23201 CTGCCCTCTC CTGGGCAGCC GCCTGCCTTT CTCACGCCCA CTGGGAATCT
23251 TCCCTCCCCA GGCTGAGGGC CGAGAGTAAT TTAGTAACCA TTAAAATTAT
23301 GAAAACCATT AAGCCTGAAA GAGCTAACAG AAAGAAAATA AACCCCGAAA
23351 CCCTTCAGAA CGGTCCTTGC AGTCCTCCTT CGACTTTCAT AGACTTCAAA
23401 GCCAAGCTCT TAGAAGCCTA ATGGTGTCCC AAGCACCTTC CAGGAGGTTA
23451 AATATTTCAT TTATTCTGCT CCATATGGAG ATAACTCACC ATTTGGGATG
23501 TTAGTCATTC TTTTAAACTT GATTTGCAAT ATTTTCAGTT TTCATATGGG
23551 AGCCATAATA CTTATGAGGC ATCTCCACTA AGTTATTTCA GTTTTAAGCT
23601 TTTAACAACT TGAGTTACAC ATTTGGAAGA AGCAATTCTC TTCCTGATAA
23651 AATTGCATCT CACAGTTGAT AGAGACTTCA GTTGAGCTAG CTACTCTTTC
23701 TAATCAGAAA TTCTGAAATA AAAGTGTTTT AGATATTATT GTCCATTATA
23751 TTCATTTTAA ATATCGGTTT AAATCTCTTT AAATGGACCG GGCACTGTGG
23801 CTCACGCCTG TAATCCCAGC ACTTTGGGAG GCCAAGGTGG GCGGATCACC
23851 TGAGGTCAGG AGTTCAAGAC CAGCCTGGAC AACATGGTGA AACCCCGTCT
23901 CTACTAAAAA TACAAAATTA GCCGGGTGTG GTGGTGCGCA CCTGTAATCC
23951 CAGCTACTCG GGAGGCTGAG GCAGAAGAAT CGTTTGAACC CGGGAGGCGG
24001 AGGTTGCAGT GAGCTGAGAT TGTACCATTG CACTCCAACC TGGGTGACAG
24051 AGTGAGGCTC CGTCTCAAAA CAAACAAACA AATGAAACAAA CAAACACTAT
24101 TTTCTCAGAA CATAACAGAC ACAAATCTTA TAGACTAGAA ATTGAGCCTA
24151 CAAATTTACT GTTTTCATGA GTGAACAAGA GAGCCTATTC CCTAAAACTA
24201 ATGGGCTTAA AAATATTTTA ATTCAGTATA AATTCATCAG GATTTGTAGT
24251 TGCAGGTATA CAAGAACCTA CTCTTGGTTG GGTTAAAAAG GAAGGGAATT
24301 TTGAAAGATA TTAGGAAGTT CATATACCAT TGAAAAACCA GAGGAGAGGA
24351 ACTTTCTTAG TCCACTCATG CTGCCAAAAC AAAATACCAT AGACTGGGGG
24401 GCTTAAAATAG CAGACATTTA TTTTCTCACA GTTCTTAAGA ATGGGAAGTC
24451 CAAGATCAAG ATTCTAGCAG GGATGGGTTT CTGGTGAGGG CTCTCTTCCT
24501 GGTTGCAGAT GGCTGGTCTG TCCCCACGTG GTCTTTCCTC TGTGCACACA
24551 GAGGCAGAGC ACAAGTGAGT GAGCTCTCTT CTTAGAAGGA CACAAATCCA
24601 GCTGGATCGG GGCCCCACCC TTGACACCTC ATGTAACCTT CGTTTCTTCC
24651 TTAGAGGCCC CATCTCCAAA TAAGCCACAC TTGGGGGTTA GGGCTTCAAC
24701 ATATTAATGT GCGGTGGGGG ACACAAACAT TCAGAACATC CAGTCCATAA
24751 CAGGAAGGCC CCAGGTTGGA TTGTCAGGAA GGATTCCCAT AACTGCATTT
24801 CAAAACTGGC TGCTACTGAC CCTCAAATCA TGCCACGTCT GCCATAACCA
24851 GAGAGCCGCT CCCACTATCA ATGTAAGAAC CCCCTCCCTC TGCTGGTACC
24901 CACATCAGCA CACAGCATGC CTGCACCTTA TCTTTTTTCA TGTAACTCAC
24951 ATGCATCAGT CTCTGAAGTA ATCTAGCAGC GCAGGAAGCC
25001 GGAAATACAG CTGTTTTTTT TTTTTAAAGT CTGTGTTGAG CTTCACAATT
25051 TAGGAAATCA TCAAAATGTG AAGATGGCAT CAAAATATTT TGAACCTCCA
25101 TGCTCGCAAT CCAGACAGAT ATGCACATCC ATTGAAATAG AACAAGGACC
25151 TCATTGATAT ATGCTCCTAT TATGTACCCA CGGAAATTTA ACAAATAAAA
25201 TAAAATAAAA TAAAATTTTC TAAGGAGACC AAACAGGAAA GTAAGGCTTT
25251 TCTGGAGAAA ATAATTTTTC TTTATTGAAA TCAGTTAAGC TGGGCCTGAT
25301 TTTAAGTTTT TGTTTTAATA ATGGTTTTGA CACTAACAAC AACAAATTAA
25351 TGATCATTTT TCTGACTGGT TATGAATGTC ATTTTCACCT CTTCTATAAA
25401 GAAAATATAT TCGTGGCTTAT GTTGAAATGT TGTCTTTTAA TTTCTCTCTA
25451 TGGTAATATT TTCTGATAGC GTTAATTTAC CCTCATTATG TGAAAAATGC
25501 ACTTGCTAAG AGCAAGTGTT TTGTCTTTAC CTGTGACAAT GCATCCTCTT
25551 CCCTGGCCTA CTGGGTAGCT TGAGAGGCCT TATCCACAGC AACGTCAGCA
25601 ACTCACAGTA TTCAAGAGGC AGAACAAAGA GAACATCTGT ATGTTTCTAG
25651 TGGATTTCAG AATCAATATT CTGTAATCTT TTTTCCAATT TAGGACCAAC
25701 AATTAGGACG GTGGCCATTA GCTCTTAACA ATATCTTAAA AGGCAGGTAT
25751 TTCTTACATG TGCTTGTTAT ATCTTTGTTT CTTGGTTTGA AAAAGAAGTC
25801 AGCTGATGAA CAGACTTTGA AGCACATTAC ATTTGTTTGA AAACATTCTG
25851 GGTTTATTAA TTCTTGACAA CTGCAAAAGT ACAGTTGTTC TTAAATATGG
25901 TTCATGTGAA TACACTCAGT TTTCTAACTT CCACAGCAAA GAACTAAATA
25951 CATTTAGCTT TTGTACCAGA ACATCCTTTT CACTGACAGT TTAGTTTTTA
26001 GGAATGTATG CTGTATGTTT TTCTCACTCT AACATGTCAG CTAGGTGTTT
26051 GCACTCAAGG ATAACTACAA AAATATTATG AAAGACATCC ATCTTCCTTT
26101 CAAATAGGAG AACGACCTTG AGCATGTCAT GCAAACTCAT TGCTATCAGT
26151 TTCTTCGTCT CTAAAACGAA AGGCTTGGGT TAGGTGACCT CTAAGTTCCT
26201 TCCAGCTCAA TAATTCCAAG TCTCTCATTT TTTGCTACAT AGTCTGGTGA
```

FIGURE 3G

```
26251 TAGCCTCTTT GAAAACTTAA AAAACAATGG ACTATTCCAG GGAAACTTCA
26301 TTTTTAGACA AGTGTTCCAT GCAATTGTAT AGTATTAGAA AACATGCAAT
26351 CAAGTTGTCT CCTTTGAGAA ACATTAAGAA AACCAAAGCT AGCTACATTT
26401 TTATGGTAGC ACAAAACATA ATATTGGATA ACAATGATAG TAAACACTAT
26451 TATCATTTGC CTGATTGTAA ACAAAACTTT TCATTTTGGA ATTTTTTACT
26501 GTGTTTTTTT TTTTAATGCA CTTGTTTCAT TAAATGGCAC AGGTATAAAA
26551 ATTGAACAAC AAAAATGCTT TCACTATGGT AGTTCCTATG TATTACACAA
26601 ATATATCCAA AGTCCTTTAA AATAATAAAA ATCTACTAAT TTAGATAATG
26651 ATGATAGCTA TTAAGCAACT TTCCCAAGGT CACCCAGGTA GTGGCAGAAA
26701 AGGGATGTCT GATTCACACC TTAACCTTAT CCTCCCTGCG ATACTCCTTC
26751 CCCAGCCTTT AATTAGTGGA GCTCATACAG CCATTGCTCC TCCAGGCACA
26801 AGCAGATTGA GTGAATAAAT GGCTCTGACA GATAAATGGA TAGAAATGAA
26851 TACCGGGGCA AGCATTGCGT CCTCCCGGAA GGACACGCCT CTCTGCTCCC
26901 ACATCACCAC TTGCTTCTAT CACAGTGCTT ATCTCACTGC ATTCTTTATT
26951 TTCTTATCAG CTCTACTAGG GCCTCAGCTG CATCTTGTTT ATTTCCCTGT
27001 TTTCAGCACT AAGTGCTGGG CTTGGCATAT CCTTAATAAA AGTTCGTTAA
27051 ATGGAAAAAA GGAATGAATG AACACACCTT AAAGAACAGG CAATGTTAGA
27101 ATAGTTCACA CTAGTTTTTT ACATAATTTT GCTTAACATC TTATATTGTG
27151 AGCAAGCGCG TATTCTATAA GTTGGAACTT TCTGTCTTAA GGGTTATTCT
27201 GGAAATTAGT TCATGAAATG AGACAGGAGA TGACCAAAAT TACAAATACA
27251 AGCAAACATC TTTGGTGTTA CATAAATTAT CTCATTGAAT GCTCACAATA
27301 GTTCTGGGAG ATAGGTGTCG TTACACTTTA TAGAAGGTGG TTCTGTTTTC
27351 TCCATCCTGA GGACAACATA GTTGTTATA AAACTTTATT TTACATCTGT
27401 AAAATATTAT TATATGGTTT TTTGCTCTTT AAGCAAGCAT TTATTTAGGA
27451 TCTATCATAT CCTGAACAGG AAAGATACAA AGATGGCTAA ACCTCAGCTC
27501 CTGATTAATG TCCATTTTGT AATCATTAAG AAGAGATTAG CCAAACAGAA
27551 ATAAAGTACG TCTCCCGCTT TCCGCTGGAA TTCATTACTT TCTTCCTTCT
27601 ACTACTGTGG TATGTTTCTA CAGGTGTTGA GATCACTGTA ACTTTTCCAA
27651 GAGATGTCAG TCCTCCCCAA GAAATGAGCC AAGAAGACTT AAAAGAAAAG
27701 AAGTAAGGAA TATTCTTTGA AGTATCAGAT TTGAAATGAA GTATGAAGCA
27751 ATGATAGTCA TATGGCAACC TACATTATTA GTAATTGAAT CCATAATAAT
27801 GCTTAAAAGT AGAGGTCACA ATAAATAGTA TGTGGCAGAG GCCAGATCAT
27851 AAACACTTTG GCTGTGTGGG CCATATGGTC TCTGTTGTGA TGATTCAACT
27901 CTGCAACTGT CATTTGAATG CAGCCATAGA CAATATGTAA ACAAATGAGT
27951 GTGGCTGTGA TCCAATTAAA GCTACAGAAA AAGGCTGAAG GCTGGATTTG
28001 GTCCCCGGGC TGTAGTTTGC TGACCCTACT GCAGGGCAGA GCTACTTAGA
28051 ATGTGGTTCT GTGGTCCTGT TACTAGTCCA TGATGAGGTC AGGACAGGCT
28101 GCGAGGGTGA CCATTAAAAA AGTTGCAAAG CAATTTGGCA AATAACTTAC
28151 GTTCATTGAT CGGGTAGTGA AACAAATTGA GGCTTATTTT TTGCATGTCT
28201 TTTATTTTTC TTCCATTTTT ATGGCAATTC ATTTATATTT TACAAAAGTA
28251 TCAGTTCACA ATGACTGGAA ATTTAAATGC TGGTTCTTCA TCAAAAATAG
28301 TTTGAGAAAC ACTGGGCTAG TCAGTACCTG TGGAGATAAA AGGGTACATC
28351 CCCCAGGCCT GCCCTTGGTC TCTGATTTCT CTGTGCAAGG AAATGGTGAT
28401 TGGGAAAACG AGAGTGAGCT GAAACCTAAT CCATCCAAGC GATGGTACAG
28451 AGGGCTAAGG AGGCCAGGAG GAGTCAGCAG GTGGAGATGT CTTACCCTCT
28501 CAGGATTCAG CCTTTCCTTT CAGCAGCACC ATTTGGAAGT AGTTCTTCAA
28551 ACTTTCTAGT GATGTCAGGC TGAACTGAGG ACTGGAGATC CAGAAGATGT
28601 GGCAACTGAG TTTTAAATCA AACATTTCCC TCCCCCTTTA GTCTGATAAA
28651 CTCATCGCTT CAAGAATGGG CACAAGCACA TGCAGTTTCT CATCCAAATG
28701 AAATAGAAAC GGTGGAGCTC AGGAAAAAGA AGCTGACCAT GCGGCCCTTA
28751 GTTTTGCAAA AAGAGGAAAG TTCCAGGGAG CTCTGCAATG TGAACTTGGG
28801 CTTTTTGCTA CCAAGATCTT GTTTAGAACT GAACATTTCC AAGTCTGTAA
28851 CCAGAGAAGA TGCTCCTCAT TTTCTGAAGG AGCAGCAAAG AAAATCTGAA
28901 GGTAAGTTGA ACATTGAATT CCACAGTGAG TCCTTTTGGT CAACAAATAT
28951 TTATGTATTG TGCCAGGCAC TGTTCTAAAT GCTAGAGATA AAGCAGTGAA
29001 CATACCAGAA AATAACCCCA GCCCTTGTGT AATTTACATT CCTGGGGGTC
29051 ATGGGGGTGC GAGACAGACA ATAAACTAGT AAACAAGTAA AATGAAGGAT
29101 GGCATAAATGT TCCAGCAGAA AGAGCACTAT ATGTGCAAAT GTTTATATAT
29151 TTGTTCAAGG AATAGAAGGC AAATATTTTG AGAATATCTT ATTGTTTAGA
29201 TTATTTCATT GCTTATTTCT TTAAACATTT CAGACATTAT TTTGTAAACT
29251 ATACTTGATA ATTTCAGTAT CAATATCCTA CTGATTTGCA CTATGGTTGA
29301 CTTTTTTCTT GAGTGTTTGA AAATCTTCAT TGTGAGCTCA TATTTGGTTG
29351 ATGTTTATCT GTGGAATCT TGGGGGCCCA CGCTGTGGAT GCTTTTGGCC
29401 AGAAGTATTG AATTTACTTC TACCAGGTCC CAGGGTCATT ATGGACTTGA
29451 GTCTACGTTA GCCTTATTCC TGGATCCCCA AGTTAATGTG CAAGTCTAAG
29501 AGCCAACTTC CAACTACATT GAGCCCAAGA CTCATTTGCT AGATAGCAGC
29551 ACTGATGCCA GCATTTCCCC CTGCGGCAAT ATTGTCTTTG CTACTTGTTT
29601 ACCACTGTCC TCAACCAACC AGCCAAACC ACCAGGAACA ACCTTATAAT
29651 CCAACAAGTT ACATTCATTG ATTTATCACA ATGAGGGAGA CTGCATGCCA
29701 GTGGAGCTGT GACACATCCT ACCAAAAAAG AAAAAAAAGA ATAATTATTA
29751 TGGGATTTTA AGAGAAGGGT ACATTTTAAG TGAAATTTAA ATGAAGCAGT
29801 GCTTAAAGTT TTTTTTTTTT TGAGACGGAG TCTCGCTCTG TCACCAGGCT
29851 GGAGCACAGT GGCCCAATCT CAGCTCACCG CAACCTCTGC CTCCTGGGTT
29901 CAAGCAATTC TCATGCCTCA GCCTCCCAAG TAGCTGGGAC TACAGGCGCA
29951 TGCCACCACG CCCAGCTAAT TTTTGTATTT TTAGTAGAGA TGGGGTTTCA
```

FIGURE 3H

```
30001 CCATGTTGGC CAGGATGGTG TCGATCTCTT GACCTCGTGA TCCTCCCACC
30051 TTGGCCTCCC ACAGTGCTGG GATTACAGGT GTGAGCCACT GCGCCTGGCC
30101 TAAATTTTTT TTTGTTTTAT TATGCTAAAA TGTGTGTAAC ATAAAATTGA
30151 CCATTTTAAT CATTTTCAAG TGTACAGTTC AGTGGCATTT AAGTACATTC
30201 ACATTGTTGT GTAACCATCA CAACTATTCA TCCCCAGAAC ATTTTCTTCT
30251 TGCAAAACTG AAACTCTGTG CCCCTTAAAC AATAACTCTA TATTTCCCAC
30301 TCTCCCAAAG CCTCTGGTGA CCACTATTCT ATTTTCTGTC TCAATACGAA
30351 TTTGACTATT CTAGGTCTTT TATAGAAATG GAATCATGCA ATATTTGTCC
30401 TGTGTCTGGC TTGTTTCATT TGGCATAATG GTGAAGCAGT GTTTTGATGG
30451 GCTATATGTA AAATAGTTCA TAAGAAATCT GGACTTGAAG TGGACCTAGA
30501 CTCTTGTTCC TTGAAATTTA CAAAGTTAGT TCCCAAATCT TGATAGCGTT
30551 TTTTTGTTTT TTGTTTGTTT GTTTGTTTGT TGGTTTGTTT GAGACACATT
30601 CCGGCTGTGT TGCCCAGGCT GGAGTGCAGT GGCGTGATCT TGGCTCACTG
30651 CAACCTCTGC CTCCTGGGCT CAAGCGATCC TCCCACCTCA GCCTCTTGGG
30701 TAGCTGGGAC TACAGGTGCA TGCCACCACG CCTGGCTAGT TTTGTTTGTT
30751 TGTTTGTTTG TTTTTTGGTA CAGATGGGGT TTCACCATGT TGCCCAGGCT
30801 GTTACTGAAC TCTTGGGCTA AAGTGATCCT CCCATCTTGG CCTCCCAAAG
30851 TGCTGGAATT ACAGGCATGA GCCACCGTGT TCAGCTTCAA CAGCCTCTTT
30901 CAGCCTCATA TCTTGCCACT CTTCCTTCGC AGCATGATAA ACTTTAGCAC
30951 ACTAAATGCC CTCTATTCCC TAAACATGCA TGTGAATATT TGCACCTACT
31001 GTTCTTTCTG CTGGAGCATT ATGCCATCCT TCAGGTTTTG TCTTAGAAAC
31051 CCCTTCCTCT GGGAAGTCTT CCTGAACTTC CCAAGACTGG ATGAGTTGCC
31101 CTTTCTTTGT TCCGCTATAG GATCCTGACC TTACCTACAA CATAGCACTA
31151 ATCAAGCATA ATTGTCACTA TTTGTTTACG TGTTCATCTT CGCCGGATTA
31201 CAAAAGCAAG AATAATTCAA CCTCCAAGCA TTTGGCATCA TACCTGGCAC
31251 ATAGCCATTA CAAATGCACT TTTAATTAAT AATAACAATA ATCAGGTCCA
31301 GGGCAGCACT TTGGGAGGCC AAGATGGGCG GATCACTTGA AGTCTCAAAA
31351 AAAAAAAAAA AAAAAAAGAA ATAAGAAGTA CTAGCTGTGC ACAGGCACAC
31401 GCCTGTAACC CCAGCACTTT GGGAGGCTGA GGCAGGAGCA CTGCTTGAGG
31451 CCAGGAGTTT GAGACCAGCC TGGGCAACAT AGGCAGACTC CACCTCTAAA
31501 AAAAGTACAT ATATAAAAAT AAATTTTAAA AATTAGGTGG CTGTGGTGGT
31551 GCACACCTAT AGGCTCAGCT ACTCGGGAGG CTGAGGTGGG AGGATTGCTT
31601 GATTCCAGGA GGCCAAGGCT GCAGTGGATG ATGATTAGTC CATTGCACTC
31651 CAGCCTGGGT GACAGACCTC ATCTCTTAAA AAAAAAAGTA CAGCTAGTAC
31701 AAGACTTTCT TCTAGTGTGT ACTTTCATAT TGCTAAATAT CATGTTTAGA
31751 ATGGTATTTA TTAATTGTTC AGTTTGGGCT TCATCTATTA AGATTTATTA
31801 CTTTTACATT ACTTGCCTCA CACACAAGCA ATGCCCAATT TTCCCAATCT
31851 TTGTGTCTAT TTTTTTAAAA TCAATATTCA ATGTCTCTGT TATTATGACT
31901 AGGTAAAATA TTATTTGCAG CTGAGCTCCA TAGTGTGTTG ATTACATTTC
31951 CTCTCCTTTT AGACATTGTA TTTATCTCAG CATTAGTAAT AACCACTTCA
32001 TTTCTTCATT TGCTTACTTT TTGTATATCT GTTACTAATT CATCCCATCC
32051 TGTGTATTGC ACCTATAAAA CAAATCTCAA TACAGGTGAT TAGATATCAG
32101 GCAATCTGTT GGTTCCTTTT GTTTTTGGAG ACATTGCTCC TGGACCCTCC
32151 TGGCCTCTAA TTTTACTCCA CACCACCTGC TCTCTGGATC CACTGCCCAG
32201 CCGCCCATCT GAGATTCCCT TCGTGTCATC CTGGGAATTC CCTTGCCTCC
32251 TTGCTGTGTT GAATCCTTGT GTACTGGATA TGTGGCTTAA TCTTCCTTTC
32301 CTTACTTTTT TTTTTTTTTT TTGAGACAGA GTCTGACTCT GTCACCCATG
32351 CTTGGAGTGC AATGGCGCGA TCTCAGCTCC CTGCAGCCTC CGTCTTCTGG
32401 GCTGAAGCCA TTCTCCCCTC TTCAGCCTCC TGAGTAGCTG GGACTACAGG
32451 CATGCACCAC CAGGCCTAGC TACTTTAAAA AAATTTCTTT GGTAGCGATG
32501 GGGTCTTACT ATATTGCCCA GGCTGGTCTT GAACTCTTGG GCTCAAGTGA
32551 TTTACCCACC TCAGCTTCCC AAAGTGTTGG GATTACAGGC TTGAGCCACC
32601 TTGCCTGGCT TCCTTGCTTT ACTTAATCCT CTTTTACTAG GGCATATTTC
32651 CCAGCAGCTT CTTGAGAAAG GGTACACGGA GAATATGAAA GATAGAGTTG
32701 TTTGTTGTCT CTAATTCTTC TGAGCTCTTT TCTTTCTTTC AGTTTGATCT
32751 GTTCTCTGTA TGTTCATATT GGAGCATTTC CTCACATATC AGTTGAATCA
32801 CATATCCTCA CATATCAGTT GAATTTGTAT CTAAAAGAGT TTCACTAAAA
32851 AGTTCTGTAT GTTTGAGTGA GCTTGTTGAA TGGGCCTCAA AGGAGCTGAA
32901 TAGGTGGAGA ACTGGACGAT TGATAGAGGG ATTCCCAAGT GTCAGCTTGT
32951 ATAGATCAAT GGACCTTTTC TCTCAGCTAG TTTTCCCCAG AGAGATAATC
33001 CAAACACCTG CCTGTAGGTT ATGAGACTGG AGGCAACATT CTTGGCACTG
33051 AATGGGGTTC ATATTTCAGT GTGTAGACTC TTCTTTGTCC TCATATTTTC
33101 ACTCCAGCTC CCCATTTCTG CTCCCAGCCA TACCCAGCTC CTTAGCATCT
33151 TTGTTTCAAG CCCTCCAGGG AGTAAACTTC CAGCCAACTG CCAGGAAAGG
33201 AGAAGAGTAA CTCCTCATAG GGGACAGGGC AGGGAATCCA GTACTTATTC
33251 CAGCACAGAC TTATGAGCAC CCTCTCGTTT CAGTCTTGCC TGCATCCCTG
33301 TCTTCAGAGG TACCTTCAGT TCCCATTCCT TTCTGAAATT CTTATTTCTG
33351 GTTGGGCTGT CCCCTTGCAA GCATTGGGCA GAACACAGAA AGCTGACAAC
33401 TCAATCAGTT ATTATTCGTC CATATAGTTT TCTCTGTCCA AAATGTTGAT
33451 ATTGCTCATC TGTTGTTTTA TCATTTGGGT GTTTTTATTT TTTGTCCTTA
33501 TTTACATGTT TTTTAATTCT TTTACTGTGA TTTTAGTGTG ATTTGTGGAG
33551 GGATTGGAGA AAAGCTTGTA CATTCAATCT GCCATTTTTA ATTGGAACTC
33601 TGTACTTATT TTATTTTATT TACTTTTTTG GAGATAGGGT CTCGCTCTGT
33651 TGCCCATGCT GGAGTGCAGT GGTGCAAACA TGGCTCGCTG CAGCCTCAAT
33701 ATTCCAGGCT TAAGTGATCC TCCACCACAG CCTCCTGAGT AGCTGGGAGT
```

FIGURE 31

```
33751 ACAGGTGCAT GGCACCACAC CTGGCTACTT TTAACATTTT TTGTAGAGAT
33801 GGGGTCTCGC TATGTTGCTC AGAGTGGTCT CTACACATTT TTAAAAGGCT
33851 TTGACACATG TTACCAAATT ACCTACCAGA AAGATCTTGC CTCTACATTC
33901 CCACCAAAAG TCTTTACCCC ACATAATTCC TGACCAATAC TGGATAATAC
33951 ATATTCAAAT ATTTATAAGA ATACTTGAAA GCGTTTTTTT AAAAAATTCA
34001 GGATGCTATC CATTATGTAC CCAACTATAA ATTATATTCA GTTGTATTTC
34051 TAGATTAACT TCTAACATCT TTTCAATAGA AAACCTCAAC CTCTAGAATG
34101 CAACCTCTGG GAGCAAAGAG CAAAGATCTG TCTTTCCTGC CCACAACTAT
34151 AAATTGCCAT CTTCTGGGAC AGTGTTGGCC ACTCAGCAGG CACTCAGTAA
34201 ATAATTGTTG AGTAAATGCA TTAAGAATGA AGGGGAGGTG CCATGGCCAG
34251 CTGTGTCCAA GGGGAATGCC TGTGCCCCCT CCTGTTGCCT GTTGGGGTCC
34301 TCTTCTTAGG TGACTTGTTT TTCACCTGGG ATTGGCTTTT CTACTGTGTT
34351 AAATCTTAGA AGTCTTTTTC TCTCCGTGTG AAACTTCAGA ATGACAGCCT
34401 GAGGCTGAAA TGGACCTACA GACATTTGTT TGACCCTCAC AACATTGAAA
34451 AACAAGGGAG GAGAGGCCAG GCCCAGTGGC TCACACCTGG AATCCCAGAA
34501 CTTTGGGAAG CCAAGAAGGG AGGATTGTTT GAGCCTAGGA GTTTGAGACC
34551 AGCCTGGGCA ATACAGTAAG ACCCTGTCTA TACAAAAAAT TAAAAATATA
34601 AAAATTTTAA ATAAATAAGC AAGGGTGGGG GAAGGAGATT TCACATAAAA
34651 CCTGCAGCTT GGGTTGGGCG CGGTGGCTCA CACCTGTAAT CCCAGCACTT
34701 TGGGAGGCCG AGGCCGGTGG ATCACGAGGT CAAGTGTTCG AGACCAGCCT
34751 AGCCAACATA GTGAAACCCC GTGTCTACTA AAAAATAAAA AATACACAAA
34801 AAATTAGCCG GGCATGATGG CAGGTGCCTG TAATCCCAGC TTCTCGGGAG
34851 GCTGAGGCAG GAGAATTGCT TGAACCCAGG AGGTGGAGGT TGCAGCGAGC
34901 TGAGATCATG CCACTATACT CCAGCCTGGG CGACAGAGCG AGACCTGTC
34951 TCAAAAAAAA AAAATCTGCA GCTCTCTGGC TTCTTTTGGA AGATGTAGCA
35001 GGGCTGGACT ATCTATCTGG GTTGGATAAC ATCACTGCGA GCTGGGTAAT
35051 GATGCCCCTT TAGTTGGGCA TATGATCTCG ATTTACTGCT GTGTCTTCCT
35101 GTCCCACATC ATCCATTTCT GTGAACTGTT TTGACCCTGG AGACACTGGA
35151 GCTTTTGGCT TCAGCTTTTAG AAAGTCCAAA CTATGCAGAA GTGGTGGTGG
35201 TGGTGGTTCA TGGGGTTTTG GGGATCATTC TGACTTTTTG GTAAGAAGAG
35251 AACAACTTGT AAGTTTTATA CTACCTAGTA AGTCCCATCT CGTTCCCTAG
35301 GTGAGTCTTC CTCACACTCA CCTTTCAGTT TTTATGGTCG ATCTAGTTTA
35351 AACAACTGTT GGGAGACACT TATACAAGAA TATTTTCACA TTTCTGCACA
35401 GTTCAGGCTT TCTAAGCAAA AAACACTAGG AAACTAAGTT AAAAGATGAC
35451 TGAATGTCAG AAACGCCTCC GAAGTTAGTG TATTGCTCCA GAGAAATTTA
35501 GAGGCTGATT TTCCCAAAAG CTGTTTGCTT ATATTCTAGG GTAATAAAAC
35551 ATAGAGTCAT CTTTTCTCCTG GAGGCATTTG CTTACAATTC ATAGTAAAGT
35601 GCTCTCTCCT TCTCTGGAGG GAAAGATGGG CTAAAGTGCC ACCACCCAAT
35651 ATACCACCTG AGTCTCATCA TTCCAGAGCT CCCTCCTGTG ATGCAGCTCT
35701 GCCAGCTGTG CAGGTCAACA CCCGGCTCTC ATCACGTTGC CCTGTGAGGA
35751 ACTGGGTTGT GGGGAACTGG CATTACAATG TTCTGTGAGT GATAAATGGT
35801 CTGCTCTCTG GTCCAGAGAT CTCAGGTTTT CTGTCAGAAT AGAGATATAA
35851 ATATAAAACA GCAACCCCTG CTAGTGGCAG CAGCCTGAAG TTTTGTGTGA
35901 TGATTCCACC TCTGTGTGAA TTCCACAGGG GAAACCTCCA ATTTCTACAA
35951 CTTTTCCTCA GACCCCTTAG CATCTGTATT ACTCCATCCC CAGACTCTGG
36001 CTTGAGACTG TTTTCTTTCT ACTACTAAGA ATATCCAGTT ATTGTTTTTC
36051 TTGTTGTAGA GTTTTCGACC TCTCATATGA AGTACAGTGG CCGAAGCATC
36101 AAGGTAAGAT TAGTGCTAGC ATTTTTGACT TGAGAATTAA AACCAAACAA
36151 CTCTATTCAC TAATTTAGAA CCAAATCCTC AGCAATTACA CTTGACCCTT
36201 CAACAATGCA GGGGGTAGGG TCACTGATGT CCCCAACACA GTCAAAAATC
36251 CACACATAAG CTTTGATTCC CCCAAAACTT AGCTACTAAT AGCCTACCGG
36301 TTGTTTTGTT TTGTTTTGTT TTGTTTTGTT TTGTTTTTTG AGACAGAGTC
36351 TCACTCTGTC ACCCAGGCTA GAGTGCAGTG GTGCAATCTC GGCTCACTGC
36401 AACGCTCCGC CTCCCGGGTT CACGCCATTC TCCTGCCTCA GCCTCCCGAG
36451 TAGCTGGGAC TACACGCACC CGCCACCACG CCCGGCTAAT TTTTTGTATT
36501 TTTAGTAGAG ACGGGGTTTC TCCATGTTAG CCAGGATGGT CTCGATCTCC
36551 TGACCTCGTG ATCCGCCCGC CTCGGCCTCC CAAAGTGCTG GGTGTTCTGT
36601 TTTGTTTTGT TTAGAGACAG GGTCTCGCTA TGTTGGCCAC GTTGGTCTTG
36651 AACTCCTGGC CTCAAGCAAT ACTCCCCCTT AGCCTCCCAA AGTGCTAGGG
36701 TTACAGATGT TAGCCACCGC ACATGGCTGC AGTAGCCTAC TGTTGACCAG
36751 AGCCTTATAG ATAACATAAA CAGTTGATTA ACACACACAT TTTGTGTTAT
36801 ATGTATTATA TGCTGTATTC TTACAATAAA GCCAAGAAAA TAAAATGTTA
36851 TTAAGAAAAT CATAAGGGGC CAGGTGTGGT GGCTCACGCC TTAATCCCAG
36901 CACTTTGGGA GGCCAAGGCG GGTGGTTCAC GAGGATAAGA GATCGAAACC
36951 ATCCTGGCCA ACATGGTGAA ACTCCGTCTC TACTAAAATA CAAAACATTA
37001 GCTGGGCATG GTGGCGGGTG CCTGTAGTCC CAGCTACTCG GGAGGCTGAG
37051 GCAGGAGAAT TGCTTGAACC TGGAAGGTGG AGGTTGCAGT GACCCGACAT
37101 CATGCCACCG GACTCCAGCC TGGCAACAGA GCAAGACTCC GTCTCAAAAA
37151 TAAAACAAAC AAACAACCAA AAAAAAAAAA CAAAAAAAGA AAATCATAAG
37201 GAAGAGAAAA TATATTTACT CTTCATTAAG TGGAAGTGGA TCACCATAAA
37251 GGTCTTCATC CTCACTGTCT TCATGTTGAA TAGGCTGAGG ACGAGGAGGA
37301 ACAGGAGGGC TTGGTCGTGC TGTCACAGAG GTAGCAGAGG AGGAAGAAAA
37351 TCCACATATA GGTGGACTTG CGTAGTTTGA AGCCCTGTTG TTCAAGGGTC
37401 AACTGTATTT CTTGGAAAAA CAACAACTCA CATATAGTTC CTAGAGTAGC
37451 AAATCGTTCC TGGGAAAATT ATGCCTTGCC ATGTGCAGTG CTTTTCTGGA
```

FIGURE 3J

```
37501 GTGTTTCTGT TCTTTACATA ATGAGCTGAG TAGCTCCCTT AGACATTTTT
37551 TTTTTTTTGA GACAGAGTCT CACTCTGTTG CCCAGGCTGG AGTGCAGTTG
37601 GCACAATCTC GGCTCACTGC AACCACCACC TCCTGGGTTC AAGCGTTTCT
37651 CCTGCCTCAG CCTCCTGAGT AGCTGGGATT ACAGGCACCT GCCACCACAC
37701 CCAGCTAATT TTTGTATTTT TAGTAGAGAT GGGGTTTCAC CATGTTGGTC
37751 AGGTGGGTCT TGAACTCCTG ACCTTGAGTG ATCCGATTGC CTCGGCCTCC
37801 CAAAGTGCTG GGATTACAGG TGTGAGCCAC CACACCTGCC CAGACATATT
37851 TTAATTTGTC TTTTTTCAAC CTATTTAGAA ATTAGGCAAT TCTTTTCTTT
37901 CCCCCAGTGG TGGAAAGATT TTCCTAGCTG TCTAATTTAT AAGTTTTTGG
37951 AAAGATATTT GCAATTCTTA GTTTCTCAAC TACCTGACCC TTCTTTTCCT
38001 ATGAGCCTTT GAGAAATACT TATGCATAGG TACTGCTTAG CATTGTAAAA
38051 GGAGTTTATT GACCTAAAAA ATTGTAATGG CTGTTACTAG GCAGATGGTT
38101 AAGCACTGGA TGAATCTGCC TTTATGTCCT AAGTCATTTT TGAGAAATGA
38151 GGAAAATCAT CTAGACAGTA AAACTGGGGT CTACACTACA TCTCATCTAC
38201 TTTTAATGCC TAAGTTTCTA GAGTCAGGTT CCATTTCCTT CCTTCTTACA
38251 CACAGGTGGC AATAGAATGA AAATTAAACA TACATTTCTT AATTACTACC
38301 CATGACCCAT GCCTATAAAT ATTGTGATAT AAATAGGTAT TGAATCTGTA
38351 TACACAGGAA AAGACCACAA TGAAAAGAAG CATAAAGTTA AGGAGTTTAT
38401 AGCTTACTGC CCGCAAAGTT TAATATTATA CATTGGGTTA CACTGACCTC
38451 TACAGGATGA TAATAAAAAC TAGCTTAGTT TGAAACTAGA GGAGGGCAAA
38501 GGAGAAAGGA AAAACTAGCT TAGTTTGAAA CTAGAGGGCA AAGGAGAAAG
38551 GAAAGCCATC CATTTGCCTG TCATCCACAA AAATGAAATT TTGTACATTT
38601 CATTCACAAA CTAATTCAGC AAAACGATGG TGAGGTAGTT GTGTTTCGGA
38651 TATGAATTCT GAGTTAGTCA AATAACTGGT AATTTTTGAG GTATTTTAAC
38701 AGCAATTTTA AACTGTTTTC AGTGGGATTT CAAAAATTCTT AAATCAATTC
38751 TATGGAAAGT AAAAAGAAAA AAGAAGAGAA ATAAAATGCT TCTTATCTTA
38801 AATTTTTTACC ATTTACATTA TAGGGCCTTC ATTTAAAAAT ATATAACCAT
38851 GAATATTTAC ATCTATAATA ATCCTGGTTT TAAAACGTGT TGTTTTAAAT
38901 TGGTTCTAAA AAAAATATTG GGAATGAGGT TTTAATTTTA AAAATTGTGA
38951 TCTTTCCAGG CATAGTGGCT CATGCCTGTA ATTCCAGCAT TTTGGGAGGC
39001 AGAAGTGGGA GGATTGCTTG AGGCCAGGAG TTTGAGACCA GCCTGGGCAA
39051 CATAGAGAGA CCTTGTCTCT ACTAAAATTT AAACATTAGC CGAGCATAGT
39101 GGCACATGCC TGCAGTCCCA GCTACTTGGG AGGCTGAGGT GGGAGGATCG
39151 CTTGAGCCCA GGAAGTCAAG GCTGCAATGA GCTGTGATTA TGCCACTGCA
39201 CCCCAGCCTG GGTGACAGAG CGAGATCTTG TCTCAAGAAG AAAAAAAAGA
39251 ATTGTGATTT CCAGGATAGC TTTGAACTTT AAAAGCCTTC CTTAAGAGGA
39301 TATTATAATC TCTTTAGACT ACTTTAAACG AGTTAGCGTG ATATTTATAT
39351 ATGTTTCTGC ATTCACAGCT TTTTCTGTCT TCCTTTTAGT TCCTTCTGCC
39401 ACCACTGTCA CTCTTGCCCA CGCGATCTGG TGTCCTTACT ATCCCCCAAA
39451 ATCACAAGTT TCCAAAAGAA AAAGAAAGAA ACATTCCAAG TCTCACATCT
39501 TTTGTGCCTA AGCTCTCAGT GTCTGTTCGT CAATCTGATG AGCTCAGCCC
39551 ATCAAACGAG CCTCCGGGAG CCCTAGTTAA GTCGTTGATG GATCCGACTC
39601 TCAGGTCTTC TGATGGCTTC ATTTGGTCAA GAAACATGTG CTCTTTTCCT
39651 AAGACTAACC ATCACAGGCA ATGCCTGGAG AAGGAGGAAA ACTGGAAATC
39701 CAAGGAAATA GAAGAATGTA ACAAAATTGA AATCACTCAC TTTGAAAAAG
39751 GGCAGTCTTT GGTGTCTTTT GAGAATTTGA AGGAAGGCAA TATTCCTGCA
39801 GTTAGGGAAG AGGATATTGA CTGCCATGGT AGTAAAACGC GAAAACCTGA
39851 AGAAGAGAAC TCTCAATATC TTTCATCAAG AAAGAATGAG AGTTCAGTAG
39901 CCAAAAACTA TGAACAAGAT CCAGAAATAG TATGTACCAT TCCAAGCAAG
39951 TTCCAAGAAA CCCAGCATTC AGAAATAACT CCAAGCCAGG ATGAAGAGAT
40001 GAGAAATAAT AAAAGCTGCTT CAAAAAGAGT TTCATTACAT AAAAATGAAG
40051 CAATGGAACC AAACAATATT TTAGAAGAGT GTAATGTACT TAAAAGCTTA
40101 TCCAGTGTAG TCTTTGATGA CCCCATTGAT AAACTCCCAG AAGGTTGTAG
40151 CAGCATGGAG ACAAACATAA AAATATCAAT AGCAGAAAGA GCCAAACCAG
40201 AAATGAGTAG GATGGTGCCT CTTATCCACA TCACCTTCCC TGTGGATGGA
40251 AGCCCAAGG AACCAGTGAT AGCCAAACCA AGCCTCCAAA CAAGAAAGGG
40301 AACCATTCAT AACAACCATA GTGTCAACAT ACCTGTACAC CAAGAAAATG
40351 ACAAGCATAA GATGAATTCC CATAGGAGTA AGTTGGATTC AAAGACCAAG
40401 ACAAGTAAGA AGACACCTCA GAATTTTGTG ATTTCTACTG AAGGTCCCAT
40451 TAAGCCTACC ATGCATAAAA CCAGCATAAA AACACAAATT TTCCCGGCTT
40501 TGGGACTTGT GGACCCCAGG CCTTGGCAAT TGCCCAGGTT TCAAAAGAAA
40551 ATGCCACAGA TAGCAAAGAA GCAATCAACT CACCGGACTC AGAAACCTAA
40601 AAAGCAATCA TTTCCTTGCA TCTGTAAAAA TCCAGGAACA CAGAAGTCAT
40651 GTGTTCCTCT CTCTGTTCAA CCGACAGAGC CAAGACTAAA TTACCTAGAT
40701 CTTAAGTATA GTGATATGTT CAAAGAAATC AATTCAACTG CTAATGGACC
40751 TGGAATCTAT GAAATGTTTG GGACCCCTGT TTATTGTCAT GTGCGAGAGA
40801 CTGAAAGGGA TGAAAACACG TATTACCGTG AGATATGTTC GGCTCCATCA
40851 GGCAGACGTA TCACCAATAA ATGTCGATCT TCACACAGTG AGAGGAAGAG
40901 CAATATCAGA ACAAGACTTT CTCAGAAAAA AACACATATG AAATGCCCAA
40951 AGACTTCATT TGGCATTAAA CAAGAGCACA AAGTCTTAAT TTCTAAAGAA
41001 AAGAGTTCCA AGGCTGTACA TAGCAACCTA CATGACATTG AAAATGGTGA
41051 TGGTATTTCA GAACCAGACT GGCAGATAAA GTCTTCAGGA AATGAGTTTC
41101 TATCTTCCAA AGATGAAATT CATCCCATGA ACTTGGCTCA GACACCTGAG
41151 CAGTCCATGA AACAGAATGA ATTCCCTCCT GTCTCAGATT TATCCATTGT
41201 TGAAGAAGTT TCTATGGAAG AGTCTACTGG TGATAGAGAC ATTTCTAACA
```

FIGURE 3K

```
41251 ATCAAATACT CACCACAAGC CTCAGAGATC TGCAAGAACT TGAAGAGCTA
41301 CATCACCAGA TCCCATTTAT CCCTTCAGAA GACAGCTGGG CAGTGCCCAG
41351 TGAGAAGAAT TCTAACAAGT ATGTACAGCA AGAAAAGCAG AATACAGCAT
41401 CTCTTAGTAA AGTAAATGCC AGCCGAATTT TAACTAATGA TCTAGAGTTT
41451 GATAGTGTTT CAGATCACTC TAAAACACTT ACAAATTTCT CTTTCCAAGC
41501 AAAACAAGAA AGTGCATCTT CCCAGACATA TCAATATTGG GTACATTATT
41551 TGGATCATGA TAGTTTAGCA AATAAGTCAA TCACATATCA AATGTTTGGA
41601 AAAACCTTAA GTGGCACAAA TTCAATTTCC CAAGAAATTA TGGACTCTGT
41651 AAATAATGAA GAATTGACAG ATGAACTATT AGGTTGTCTA GCTGCAGAAT
41701 TATTAGCTCT TGATGAGAAA GATAACAACT CTTGCCAAAA AATGGCAAAT
41751 GAAACAGATC CTGAAAACCT AAATCTTGTC CTCAGATGGA GAGGAAGTAC
41801 CCCAAAAGAA ATGGGCAGAG AGACAACAAA AGTCAAAATA CAGGTTGGTA
41851 TAATTAGAAT CCAAGATTCA TTGGGGTGGG AAGGACCTCA GAGACAATCT
41901 GGTTCAAACC CCTTATTTTC AAATGAGGAA TTATAAACCC TAAACAATTA
41951 AATAGTTTTT TCAAGGTCTC ACTGTTTGAT CACAAGGTTG GAAATCAGGT
42001 CCTCTGACCC CCAGGCTAAG ATGTTTTCAT TATATTGACT CCCTTCTGGA
42051 ATTTAGCTAG CTTGACATTG CAATGAAATC AGTTTGGTTA AATTAATTTA
42101 GCAAAACCAT TCAAATAGGT CAGTATTTTA TTCAATGATG ACATTTTCAA
42151 TCAACAGCAT ATCATTTCCA ACTATCAGCA GATACATAAT TATAGGCAAG
42201 ACATTGCTCT AGGTATGTGA GATAGAAAGA AATGAACATG GCTCCAGAAG
42251 TGGCTCACCA TTTTGTTCAT AGGAAGACAT GAAATGTACA TTTCTCAGAG
42301 CCCCTACACC TGAGCATTTG CTCTCAGATG ATTCACTACT TTAATGCAAA
42351 ATTATTATTG ATGCCTACTG TGCTTCTGGC AGTGGGCCAA GAACTAGGAG
42401 CATAGTGCTG TACAAGACTC GGCCATTGCT CTCATGGAAG TGTAAGCAAA
42451 AATCCTGAAA TAAGATTTTT AAAAATTTTG TTTGGCATGA GAGTTGGCAT
42501 GGAGTGGGGA AGAAGATCAA CACATAGTCG GGTTTTCTTT GTTATCGTTT
42551 TCACTAAAGT ACACAAGCCT CCCAAACTGA AATTTTAAAG ACAGAAACAG
42601 TAGGTAAACT GAAATATTAT TTATTGAACA CTAACTCAGG TCATACTGCA
42651 CTATATCCAC ACTATATCAG GATCAGGAAT AATTTTTTTT TGAGATGGAG
42701 TCTTGCTCTA TTGCCCAGGC TGGAGCGCAG TGCTGCGATC TCGGCTTGCT
42751 GCAAACTCCA CCTCCTGGGT TAAAGCGATT CTCCTGCCTC AGCCTCCCAA
42801 GTAGCTGGGA TTACAGGCAC TCACCACCAC GCCTGGATAA TTTTTGTATT
42851 TTTAGTAGAG ACGGGATTTC ACCATCTTGG CCAGGCTGGT CTTGGAACTC
42901 CTGACCTCGC GATCCACCTT CCTCGGCCTC CCAAAGTGCT GGGATTACAG
42951 GCGTGAGCCA CGGCGCCCAG CCAGGAATAA TTATTTTAAA TAATTATTGG
43001 TCAGAAGAAC ATACAAGGTA AATAATTATC CCATAGCTTC CTGGACTGTT
43051 TGCTAGAGAT ACTAGTCTGA CTTACTGCAA GTCTGGCTTG TGGATGGTAA
43101 ACTGGCTTCC TGTTTTGGTT ACTGTAGATA ATGGGTTGAT TTCCTGGGTT
43151 GGTTGCTGCA CATTGTAGGT CAGAGTTCTA TTTTTATATA TGATCTGGCC
43201 ATTGTTGGTT TGTATATTAT CTCTCAGTAC ATATGTGTAT GTATATATAT
43251 GATATATATG TGTGCATGAT ATATATTTAT GTTTATGTGT GTGTACATTT
43301 GTGTGAACAC ATATGTGAAT ATGTGTGTAT GAGTTTGTGT GTCTCTATGT
43351 GTGTGTCCAG CTCTGTGTAT GTTTCTCTTT CTGAACTTGT CTGTGTTTAG
43401 GAGCAAGCTG ACCACGATAA TGGGAATTTT GAGGAGAGAG TTGAGGTTAG
43451 GGGGCTGAGG AGATGGCACA CACTAACATA TTCTGTCATG ATAGGGACCT
43501 TGTGAAAGAT AATTCTCAAA AGACAGTGGT TAGTAGCTGC AGGGCTATGT
43551 GGGGCCTGAG ATGAACAGGA CTAAGATCTC CTCCTATAAA ATATGCAGAG
43601 CAAGATGTGG TTTTAAAATG TGTATAATTA ACAAGGCTGA AGTTCACAAC
43651 TAAGATACAC TATGTGGTCA TTTGGGGGAA TGATGTGTCT CTAGAAGTTA
43701 CCTGTAAGAG TGGCCACAGA CAGGAACATT TGAAAAGAAG ACTTTACTCT
43751 CACCCCTTTC TCTCCATCCC AGTGACTTGG TTTAATGGTC ATCTTTCCTT
43801 TTGTCTCATT CTTCCAGAGG CATAGTAGTG GGCTCAGGAT ATATGACAGG
43851 GAGGAGAAAT TTCTCATCTC AAATAAAAAG AAGATATTTT CTGAAAATAG
43901 TTTAAAGTCT GAAGAACCTA TCCTATGGAC CAAGGGTGAG ATTCTTGGAA
43951 AGGGAGCCTA CGGCACAGTA AGTTAAACTG GAAACTTGAA ATCAAACCTT
44001 CCCCCCACCC CCCCACAGTC CCTCCCTCCA CCCCTCCCAC TCCCCCAGTC
44051 ATCCTCCCTG CTTCCTCTGG CAAGCACTCT TTTACTTAGA ACTCTTTCAG
44101 TTGGAAGTAA CAGAAAATCC AACCACTGAG GGAAAGGACA GTTACTGCTT
44151 TATCCGACTG AAAGGTCTGG AATAGGTCTG GCTCTGGGTC CAGGAGGCTT
44201 CAGGGATCAG ACAATGTCAT CAGGATCTGG TCTCTCTCTC TCTTTGCCTG
44251 GCTTTTTCTC AGGCACATAT AGTGACTCAA TGGCCACTGC ATTTCTAACC
44301 TCTCATCCTC CCAGGTTCAA GTCCAGATGG AAAGAAATAT CTTCCTTCAA
44351 CAGCTGAATA TGTTACTGGA AGTTTGGAGA ATCATTACTA GATGGCAAAA
44401 ACAAAAGATG TTCCTTCCAT TTTGTGAACT GCATAAGAGA TCTTGGGGGG
44451 TGGGCGATGA AGAGAGGTGG GTACAAACAT ACAGTCAGAT AGAAGAAATA
44501 AGTTCTAGTG TTTGATAACA CAGTAGGGTG ACTATAGTTA ACAACAATAT
44551 ATTGTGTATT TCCAATTAGC TAGAAGATTG AAATGCCCCC AACACAAAGA
44601 AAATGACAAA TGTTTGAGGT GATGGATGTC CTAAACACAC TGTCTTGATC
44651 ATTACACATT CTATGCATGT ATTAATATAT CAGATGTGCC TCTTAAATAT
44701 GTACAAACAT TATATATCTA AACCCTAGCA CTTTAGATAG TTATTTACAT
44751 AGACGAGTAA AGAAAAGGCT GGCCCCCAAA TAAGACTTGT GCTGTCTCCA
44801 GATGGGGACA TTTCAGAAAT CAGTGAGAAG ACAGGAAGAC ACAAAACCAC
44851 TGAGATTACA TCACAATGGT GATTTCCAGG GCCTGTCTCC TTCTCACTCC
44901 AGAGAGCTTG GGAGCTGAAC CAGCTCTATT TTACATATTA TCAGGAGCTT
44951 TTCCAAACCA CCATCTCATG TAGTCATCAT AGAAATCTGG GAGGCAGGCC
```

FIGURE 3L

```
45001 AGGTGTGGTG GCTTTCACCT GTAATCCCAG AACTTTGGGA GGCCGAGGCG
45051 GGTGGATCAC TTGAGGTCAG GAGTTCGAGA CTAGACTGGC CATATGGTAA
45101 AACCCCGTCT CTACTAAAAA TACAAAAATT AGCCAGGTGT GGTGGCACAG
45151 ACCTGTAATC CCAGCTACTC AGGAGGCTGA GGCATGAGAA TTGCTTGAAC
45201 CCCGGGGCAG AGGTTGCAGT GAGCCCAGAT CACACCACTG CACTCCAGCC
45251 TGGGCGACAG AGCGAGACCC TGTCTCCAAA AAAAAAAAAA AAAGAAAAAA
45301 ATCTGTGAGG CAGCCTGGGC AACATAGAGA GACCTCGTCT CCACAAAAAT
45351 ACTTTAAAAA TTAGCCTAGT GTGGTGGTAC ATGCCTGTAG TCCCAGCTAC
45401 TCAGGACACT GAGGCAGGAG GATCGCTTGA GCCCAGGAAT TTGAGGCTGC
45451 AGTGAGATAT GATCAGGGCC ACTGCACTCC AGCCTGGGTG ACAGAGAGAG
45501 ACTCTGTCTC CAAAAAAAAA AAAAAAAAAA AAGAAAGAAA AAGGTAGCAC
45551 GGTGGCTCTA CAAAAAGTAC ACACACACAA TTAGCCAGGT GTGGTGGCAC
45601 ACACCTGTGA TCCTAGCTAC GAGCTGCTCA GGAGGCTGAG GTAGGAGGAT
45651 TGCTTGAACC CAGGAGGTTG AGCCTGCAAT GAGCTGTGAT TGTGCCAATG
45701 CACTCCAGCC TGGGCAACAG AGTGAGACCC TGTCTAAAAA CAACCAAAAA
45751 AAAAAAAAAA AAAAAGAAAA GAAATCTCTG AGGCAAGTAT TGTTACCTCA
45801 GTTTTACAGA TGAGAAAAAC TGAAGTCAAA AGATTACACA TTTATCCCAA
45851 GTTATATAGC TGGGGAAAGA TGAAGCCAGG ATTCTAGCCA ATTCAAGCCA
45901 CTTGACTTTA AGCCAATATG ACATCCATCC ACCATGTTTC TCATACCCAT
45951 CTTGGCTCCA CTGAAACACT GAATTTGCTT AAACACTTTG CATTTAGGAA
46001 GGGAGGTATC AACTTAGAGA AAGACAAGGG TTTAGAAAGA GAAGGGAAAG
46051 TCAAGTGTCA CCTGAGGCAT TTTGTGAATA AGTTATGTCA TTAATTTAAT
46101 AACAAGGTAT TATTGATTTG CTTCTAGGTA TACTGTGGTC TCACTAGTCA
46151 AGGACAGCTA ATAGCTGTAA AACAGGTGGC TTTGGATACC TCTAATAAAT
46201 TAGCTGCTGA AAAGGAATAC CGGAAACTAC AGGAAGAAGT AGATTTGCTC
46251 AAAGCACTGA AACATGTCAA CATTGTGGCC TATTTGGGGA CATGCTTGCA
46301 AGAGAACACT GTGAGCATTT TCATGGAGTT TGTTCCTGGT GGCTCAATCT
46351 CTAGTATTAT AAACCGTTTT GGGCCATTGC CTGAGATGGT GTTCTGTAAA
46401 TATACGAAAC AAATACTTCA AGGTGTTGCT TATCTCCATG AGAACTGTGT
46451 GGTACATCGC GATATCAAAG GAAATAATGT TATGCTCATG CCAACTGGAA
46501 TAATAAAGCT GATTGACTTT GGCTGTGCCA GGCGTTTGGC CTGGGCAGGT
46551 TTAAATGGCA CCCACAGTGA CATGCTTAAG TCCATGCATG GGACTCCATA
46601 TTGGATGGCC CCAGAAGTCA TCAATGAGTC TGGCTATGGA CGGAAATCAG
46651 ATATCTGGAG CATTGGTTGT ACTGTGTTTG AGATGGCTAC AGGGAAGCCT
46701 CCACTGGCTT CCATGGACAG GATGGCCGCC ATGTTTTACA TCGGAGCACA
46751 CCGAGGGCTG ATGCCTCCTT TACCAGACCA CTTCTCAGAA AATGCAGCAG
46801 ACTTTGTGCG CATGTGCCTG ACCAGGTAAG AAACTGAAAG CAAGAGGAGG
46851 AAGATAAATG CCCGGAGATT CCAAGTGGCA GACATTTCCC TTTCAATTTA
46901 TGGCCCATTA AAAGCTCTGT TTTGGTTATG AAGTCAAGTA GACAGTGATT
46951 TTGTGCCGAA AGTAATCATA ATCAGTCATA TTGGGTAATT GTGTTCATTG
47001 TTGTATCAGG GTATAGGAGG CAATGCTTCA AGTAGAAAGT GCCTCAATTA
47051 AATGTCTTAT CAAGTTCTGT CAATACTTGC CCAAATCAAT GGGTTTGCAA
47101 AATTTGTTAA AGATCTACTT ATTTACCAAT GAGACATCTT CCTAGGAACT
47151 GGCTAGGGTG AAATGACATC ATCTTGCATT TAAAGTGAGG GGAAACATTT
47201 TGAGCCAAAG AAACAAATTG GAGATTTCAA GCGTCAAGTG GGGGAGTATT
47251 TGGTGAATCG GAAAAGCCTT AGAAAATTGC CTGTTTTCCC CTTCCTTATC
47301 TTCTCTCCTA TCTATGGAAT TAAATTGTGG GTAAAATGTT AGAACTGTAA
47351 CTGTAATGTA ATGGAAATTA ACTAGTGCTG TGATTTTCAA ATTTTTAGCC
47401 AGGTACTCTG CTCATAGAAA TCTTAAATCA AAGAATAAAA TAAAAGCAGA
47451 CAGATGGCTC TAGTTAAAGT GTGTATCCAT GGGGCGGGGA AGAGTTAAGG
47501 AGTAGGGCTG TGGGTGCTGG AGCCCACTCT AGGATACTGC ACAGCAGCCC
47551 CAAACCCACC TACCTAGCAA GGCTCAACTT TAATTGGAGG ACAAGAAAGG
47601 CCTGAGACTC AAAGTCAATT TCCTGTCTTT CAAGTAAGTT TGCCTTCTTA
47651 TCCCTAGATG AAAAACTCCA GTGTCCCATC TTTTAGCAAG CACATATGGC
47701 AACCCCCAAC TCCCAGGGGG TTCATTTTGC CTTTCTGAAT AAATCTTAGA
47751 ATCTACAGGT CTCCCTCTCT GCCAATGAAT GTGCCTCTCT TTCAGTCTCT
47801 GTCTCTCTCT CCCAGCACAT GTGTATCAGC CTGTCCTGGC TGATTTCAGG
47851 ATGATTACAT GGGCCAGGGC AGGAATGCCA CTCCAGGGGT ACAGTTTTTG
47901 GCATTGCTAG ATGCAGAGAA CCCTTAGGTT TCCAGCGTGG ATTTTGTGGA
47951 CAGAGCCCCA GTCATTGAGC TGCCCACCCT CTCCAAAAAA AAAAAAAAAA
48001 AAAACCGCAT AAATGTGTTG GAAAATCGTA TAGACAAGTA CTAGTTTGAT
48051 ATTGGTGTTA ACTGTTAAAA CTATTGTAGT TGCTTTGTTC CGAATTTAAC
48101 AATTACCTAT ATTATTGACT CACAGCTAGA AACCACTTGT TATTCTCATT
48151 TTCTTTCAAG TTGTGATTAC ACACACACAC ACACACACAC ACACACACAC
48201 ACGAAGCACT TTAAAGAGAA AGGGTGGAAT CTTCTTTTAT GGCTCTCCTT
48251 TTGAACCGTT GCTTCATAAA CTAAGCAATA TACAATTCAC ACCACTAATA
48301 AAAATTAACA GGGTTATTGT GAAGGTTAAG TGAAATGGTG CATGTAAATT
48351 GCTTAGCAGA GTGTGGGGCA CAAAATTAGG AGTTTACAGT TAATAATCAT
48401 TAGGAAGAAT ATTAACATAC CTTACCTAAT TAGAGTCATA TACAAGTATA
48451 TAATTACCTC CTAAAATTCT ATGGCAAAGA CCCTGAGGAC CCTAGCATCT
48501 CACCTGATAT CAATAACAAT ACTCCTTGGA GATAGGGATA TTCAGAAAAT
48551 AAAGGGCGAG GCACTCTTAA AGATTCAGAA ATAGAGATAA TCAGGCATAG
48601 ACTAGGGAAA GTCTAAAGAA AACAGAAATG AACTTGGGGA AGCTGAGAGA
48651 AATAAGCATG GAGGGGGTAC TCCTATTGAC AGATCAAGTT CCTGGGAAGT
48701 CAGGCCAAGG AGTTTAGCTT TGTTGCAATA GGCAGTGAGG AGCAGGGGGC
```

FIGURE 3M

```
48751 TGCAAAAGAT TTGGGGTAGA AAAGGCCATA AAGAAAAGGG TCTTTGGGAA
48801 GGCAGGTCAG ATGGCAATGT ATTGAAGGGC CTGGGATGGA TGTCGCTTGA
48851 GACTAGAAAG CTCTGCAGAA ATCCAGAGCT TGGATGCTGA TGGTGGTAGA
48901 AGCAGTGGGA TTGTAAAGGA TTCCAGAAAA TTTCAGAGAA AAGGTGAATC
48951 AAGACTTGGT AATGGAGCAG AATGATAGGA TTTCACATTT TTGACTCTGG
49001 ATAATGGGAG AAATCACAGT TGTGAGAGAA GAACAGGGAG GCAGCTAAAC
49051 CCTTCCCACC TCCTGTAAGG AGACATTTGA AGCTATGGAA TTGCAGCTCA
49101 GGAAAGCAAT TAAGATTGGA AGGACACATT TAAAAATAAT TATAACAGCC
49151 AGGTGCAGTG GCTCATGCCT GTAATCCCAG CACTTAGGAA GGCCGAGGTG
49201 GGGGGATCAC TTAAGCCCAG GAGTTCAAGA TGGAGACCAA CCTGGGCCAC
49251 ATGAAGAAAC CCCATCTTTA CAAAAAAATA CAAAAATTAG CCAGGCATGG
49301 TGGTGTGTGC CCGTAGTCCC AGCTACTCAG GAGGCTGAGG TGAGAGGATG
49351 AGAGGATCGC TTGACCCCGG AAGTTGATGC TGCAGTGGGC TGAGATGGCA
49401 CCACTGCACT CCAGCCTAAG GGACAGAGTG AGACTCTGTC TCAAAAAAAA
49451 AAAAAAATCA TTATAAGGTT GATTGCTACA GTCATAACAA AATTATAGGG
49501 CTGAGGAAAA TATTTTGAAA ATGCTCACAA TGGAAGCTAA CAGAAATGCA
49551 TGGCATCAAG TCTAGCACAT AACTGGAGAA GGGAAGGGAG GAAGGGAAGG
49601 GAGTTGCCCC AAGGTGTAAG AAGAAACAAG AGGACAGAGT GTCCCTAAGT
49651 CTAAGCAGAG GTAGTTTCAG GTAGGAGGGA GTAGTGAATG TTTCAAGCGC
49701 TACAGAAATG ACAAACAGCT CATTAAATCT GGTTAATTTC AAGAGGGCAA
49751 TTTCTATAGA GGAATGGGCC AAATGGTTAA GAATACAGGG GGGAAGTCAC
49801 CGAGCTTAGC CTTGTTAGAG ACATTTGGCA GAGACATTTA AAATGGGATG
49851 GGCCAGGCGC AGTGGTCCAC GCTTGTAATC CCAGCACTTT GGGAGGCTGA
49901 GGCAGAATAA CTGATTGAGC GCAGGAGTTT GAGATCAGCC TGGCCAACAT
49951 AGGGAGACCC TGTTTCTACA AAAAATTTAA AAATTAGCCG GGCGCGGTGT
50001 CACGCCAGTA ATCCCAGCAC TTTGGGAGGC CGAGGCGGGC GGATCACGAG
50051 GTCAGGAGAT CAAGACCATC CTANNNNNNN NNNNNNNNNN NNNNNNNNNN
50101 NNNNNNNNNN NNNNNNNNNN NNNNNNNNNN NNNNNNNNNN NNNNNNNNNN
50151 NNNNNNNNNN NNNNNNNNNN NNNNNNNNNN NNNNNNNNNN NNNNNNNNNN
50201 NNNNNNNNNN NNNNNNNNNN NNNNNNNNNN NNNNNNNNNN NNNNNNNNNN
50251 NNNNNNNNNN NNNNNNNCT GGGTGACAGA GCGAGACTTC ATCTCAAAAA
50301 AAAAAAAAAA AAAAAAAAAT TTAAAAATTA GCAAGTCATG GTTGTGTACA
50351 CCTGTAGTCC CAGTGACTCA GAAGGCTGAG GTGGGAGGAT CACTTGAGCC
50401 TGGAAGGTTG AGACCACAGT GAACCGTGAT CATGCCACTG CACTCCAGCT
50451 TTGGCAACAG AATGAGACCC TGTCTCAAAA AAAAAAAAAA GTGGGTGGGG
50501 GAGCGGTGGT AGCTAGAAAT GGTATCCAGT TCAAGGAAAG GATTTTAAAG
50551 GAGAGAGATT TCTGCATATT TTAAAGGCCG GAGAAAGGGC CTCCAGATAG
50601 TGAAAGAATT TTTTTTTTTT TTTTTTTTCC GAGACGGAGT CTTGCTTTGT
50651 TACCCAGGCT GGAATGCGGT GGTGTGACCT TGGCTCACTG CAACCTCCGT
50701 CCATGGGTTC AAGCAATTCT CCTGTCTCAG CCTCCCAAGT AGATGGGACT
50751 ACAGGCGCCT GCCACTGGGG CCAGCTGATG TTTTTGTTTT TTTAGTAGAG
50801 ACGGGGTTTC ACCATGTTGG CCAGGCTGGT CTCGAACTCC TGACCTCGTG
50851 ATCCACCCAC CTTAGCCTCC CAAAGTGCTG AGATTACAGG TGTGAGCCAC
50901 TGTGCCTTGC TGTATTTTTT TTTTTTTTAC TTTTGAAATG ACACAAAATA
50951 TAATACTTTT ATACAAAATA CTTTTAAGAG TATTTATTTC CATTTTCACC
51001 TGGAAAATGA TCTGGTGGCC ATTGTGCTTT CAAAATTATT AAAAGAGGAG
51051 GGGCTTCAAG ATGGCTGACT AGAGACATCT GGCACTTACT TCCTCCACAA
51101 AGAACTAAAA TAGCAAGTAG ATAAGCACAT TTCAAATATA GCATCCTGAG
51151 AGAGAACACT GGATTTCAAC AGAGAAGTTA CAGGAAACAC CTGAGACATG
51201 GAAGAAAAGG AAAGGAAGAC AGTCAGTTTG GTTGAGATTG GCCGAGAGCC
51251 CAGAGAGCCT CCCTAGTGTG GGGAAAGGGT GAGCAGATCC TCAGTGGTCC
51301 ACATTCTCAC AGTGAACTCC TGCAATCCTA GCCATGGGAG AACCCTTTAG
51351 TCCTTGCAGA CACTGAGACT AGAATATGGA GCTGCCTGGA AACCATGTGA
51401 CAGCATTGCT CCGGAGAGGG AGCTCACACC TGAGTCCTAA GCAGCTACAG
51451 CATGGCACCA TTTTGAGAGT CCAGCCCCCA CCAGACTCCA TCCCGCCCTG
51501 GGGTCCAACA GCCCCTGCAA CTCCATATCC TTGGAACCCT ACTTACATCT
51551 TCTTGTGTTT ACCTGGAGGG CTGCAGCAGT GTGATGCCAG TTGTACCCAG
51601 TGGAGTGGCC AGATCCCCAG CATTGTAGCA CACATGGTGT CCTGCACCCC
51651 AGAAACAACA GTGCAGCGCA CCAGGGAGGC TGCTCCTGGG ACAAAGGGAG
51701 CCAAAGCATG TGCTCCCCAG TGCCTAAGAA CTGCCTACCT GAGGTGGCTA
51751 TTACAGATAG CAACCCCACC CTTTCTAGCA GCAGGGCTGC CACACACATG
51801 CTCTGAGGAC AGACTCTGCT GCTGTCCACT GCAGCTTCTG CTTAGGCTGA
51851 AGTGTGTGCC ACTGGCAGTG ACCCCACCCG CTTCAGCAAC AGGGTTGCAG
51901 CACATTTGCA TGTGCCCTGA GGACTGGCTT TCTTGGCTGC AGCTGCTGCC
51951 ACCACCAGAA GCCAAACCAT GAGCTCCCTG GAACCTGAGA GCCACCTGCC
52001 TGAAGCTGCT GCCACTGACG GCAACTCTGC TTCCACCAGT AGCAGGGCTA
52051 TAGCACACTT GCACATGCCC TAATGACAGG CTCCCCTTGC CCACCACCAC
52101 CGGAGCTGCA GCCACCCAAT CATCATGCCA GGGCCCTGGG GATCACCCCA
52151 CCCTGCCCAC TACTGCTGAC CCCTGCGTGT ACCACTGGAG GGCCTGAGGA
52201 AAGGTCAACC AAGCCTGGCC CAGCAGCCCT GCCGGTGTCT GAGCACATTG
52251 CCTGGGGCCT GGGGATTCTC TGCCCTATCA CTGCTGGTAT CTGTACATTC
52301 CTCATGAGGA CCTGAGGACC GGCCCATCCA GCCCATTGCA GCCACTATTA
52351 ACACCAGTGC CTGCTGCTAT GGAGCCCAAG CATTATCCCA GTACCACTAT
52401 TGCCATTGCC CATGCCATGC ATGCTGCCCA GGAGTCTAAG GACCTATCCA
52451 CCCACCCAGC ACACCACTGC CACTACCAGG ACCTGAGCAA GCCTTGGAGG
```

FIGURE 3N

```
52501 CCCAAGAATT GGCTCATTTG AACCCACTAA CACTAGTGCC CATGTATGTC
52551 ACCCAGGGGC CCAAGGATGG GCATGCTTGA CACACCACTG CTACCACTCA
52601 GNNNNNNNNN NNNNNNNNNN NNNNNNNNNN NNNNNNNNNN NNNNNNNNNN
52651 NNNNNNNNNN NNNNNNNNNN NNNNNNNNNN NNNNNNNNNN NNNNNNNNNN
52701 NNNNNNNNNN NNNNNNNNNN NNNNNNNNNN NNNNNNNNNN NNNNNNNNNN
52751 NNNNNNNNNN NNNNNNNNNN NNNNNNNNNN NNNNNNNNNN NNNNNNNNNN
52801 NNNNNNNNNN NNNNNNNNNN NNNNNNNNNN NNNNNNNNNN NNNNNNNNNN
52851 NNNNNNNNNN NNNNNNNNNN NNNNNNNNNN NNNNNNNNNN NNNNNNNNNN
52901 NNNNNNNNNN NNNNNNNNNN NNNNNNNNNN NNNNNNNNNN NNNNNNNNNN
52951 NNNNNNNNNN NNNNNNNNNN NNNNNNNNNN NNNNNNNNNN NNNNNNNNNN
53001 NNNNNNNNNN NNNNNNNNNN NNNNNNNNNN NNNNNNNNNN NNNNNNNACC
53051 CATTCAGACA AAAATAAAGA AAAAAAAGAG TGAACAAAGC CTACATGACA
53101 TGTAGGAAAC TATAAATTGG CCAGATATAC AATTTTGATT GTTCCAGAAG
53151 GTGAAGAGAA GACCAAAGGT ATAGAAAATC TATTTAAAGA CAGAATAGTT
53201 GAAACTTTCC CAGGTCTAGC AAGAGATTTA AACATCCAGA TACAGGAAGC
53251 TAAGAGATCC ACAAATAGAT ACAACCTAGA AAGGTCTTCT CCAGGGTACA
53301 TTGTAGTCAA ACTGTCAAAA GTCAAGACA AAGAGAAAAT TCTAAGAACA
53351 GCAAAAGAAA AACATCTAGT AATGTATAAA AGAACCCCCA TCAGACTAAC
53401 AGTGGATTTA TCAGCAGAAA TCTTACAGGC CAGGAGAGAA TGAGATAATA
53451 TATTAAAAGT TTTAGGCCAG GCATAGTGGC TCGCACCTGT AATCCCAGCA
53501 CTTTGGAAGG CTGAAGTGGG TGGATCACCT AAAGTCGGGA GTTTGAGACC
53551 AGCCTGACCA ACATGGAGAA AATCCATCTC TACTAAAAAT ACAAAATTGC
53601 CCAGGTGTGG TGGTACATGC CTGTAATCCC AGCTACTCTG GAGGCTGAGA
53651 CAGGAGAATT GCTTGAACCT GGGAGGTGGA GGTGCAGTG AGCCGAGATT
53701 GTGCCTTTGC ACTCTAGCCT GGGCAACAAC AGCAAAACTC CATCTCAAAA
53751 AAACAAACAA ACAAAAAAAA AAGTTTTGAA AGGCATAAAA ACAAAACAAA
53801 ACTGTCAGCC AAGAATGCTA TACTCAGCAA AGTTATCCTT CAAAAATGGA
53851 GAAAGTTCTTT CACAGACATG CAAAACTGA GAAACTTCAT CACCATTAGT
53901 GGCCCTACAA GAAATGCTTA AGAAAGTCCT ACACCTGGAA GTGAAAGGTC
53951 ATATCTATCA TCATGAAAAC ATATGAAAGT GTAAAACTCA CAGGTAGAGG
54001 AAACCACACA AAAGAGGTAG AGAAAGGACT CAAACGTTAA CACTACAGAA
54051 AACCACCAAA CCACAATGAT AAATAACAAG AGAGAAAGAA AGAAAGAAAC
54101 AAACAAACAA ACAAACAAAC CAACCAGAAA ACAATCAACA AAATGACAGG
54151 AATAAGAACA TAAATGGATT AAAATTTCCA ATTAAAATGG CTGAATAGAT
54201 TTTTAAAAAG TGACCCAAAA ATATACTGCT TTCAAGAAAC TCACTTTACC
54251 TGTAAAGACA CATATAGACT GAAAGTGAAA GGATGGAAAA AGATAGTTCA
54301 TGCAAATAGA AACCAATAGA GAGCATGAGT AGCTATATTC ATATCAGATA
54351 AAACACACTT TATGTCAAAA ACAGTAAAAA GAGACAAAGT CACTATATAA
54401 TGATAAAGAG AAAAATTCAG CCAGAGGATG TAACAGTTCT GATGCACCCT
54451 GCACCAGAGC ACCCAGGTAT ATGAAGCAAA TATTATTAGA TCTGAAGAGA
54501 GAGATAAACT CTAATACAAT CATAGATGGG GACTTTAACA CCCCACTCTC
54551 AACATTAAGC AGATCATCTA AACAAAACAT CAATAGAGAA ACCTGGATTT
54601 AAATTGCACT TTAAACCAAA CAGACACAAC AGATACCTAC AGAATATTTT
54651 CTCCAACAAT GGCAGAATAA ATGTTCCCAT TAAAACATGG AACATTTTCC
54701 AGGATAGGCC ATACATTAGG CTGCAAAACA AGTTTCAACA AATTTTTAAA
54751 AATCAAAATC ATACCAAGTA TTCTTTCAGC CACAATGGAA TAAAACTAGA
54801 AATCAATAAC AAGAGGAACT TTGGAAACTG TATAAATACA TGGAAACTAA
54851 ACAACATGTT CCTGAATGGC TACTGGGGCA AGAAAAGAAAT TAAGAAGAAA
54901 ATTAAAAAAT TTCTCAAAAC AAATGAAAAT CAAAACACAA CATACCCAAA
54951 TCTATGTGAC ATAGTAAAAG CAGTGCTAAG AGGGAGGTTT ATAGCAATAA
55001 AAGCCTACAT CAAAAATGTA TGAAGATTGG CTGGGCATGG TGGCTTACAC
55051 CTGTAATCCC AACACTGTGG GAGGCCAAGG TGGGAGGATC ACTTGAAGCC
55101 AAGAGTTCAA GACCAGCCTG GGTAGCAATG TGAGACCTTG TCTCAAAAAG
55151 AAAAAAAAAA AATTAGCTAG CTAGGTCACT TGGTAGGCTA GGGTGGGAGG
55201 ATTGCTTGAA CCCAAGAGTT CGAGACTGCA GTAAGCCATG ATTGCACCAT
55251 TGCATTCCAG ATGGGGTGAC CTTTTAAAAA AGTATAAAAA TTTAAATAAA
55301 TAATCAAGGA AACAAGAAA AAAGGGAACA AACCAAACCC CAAATTAGTA
55351 GAAAAAAAGA AATAAAGATC AGATTATGTT AAGTGAAATA AACCAGGATC
55401 AGAAAGACAA ACATTGCATG TCCTCACTTA TTTGTGGGAT CTAAAAATAA
55451 AAACAATTAA ATTCATTAAC ATAGAGAGTA GAAGGATGGT TACCAGAGGC
55501 TGGGAATGAT AGTAGGAGGA TAGGAGTAGG GCAGATAGGG ATGGTTAATG
55551 GATTAAAAAA AAAATAGAAA GCTTGAATAA GACCTACCAT TTGATAGAAC
55601 ATCAGGGAGA CAATAGTCAT TAATAACTTA ATTGTACATT TTAAAATAAT
55651 TAAAAGAGTG TAATTTAGATT GTTTGTAACA CAAAGGATAA ATGCTTGAGA
55701 GGATGGATAC CCCATTCTCC ATGATGTAAT TATTTGACAT TGCATGCCTG
55751 TATCAAAACA TCTCATGTAC CCCATAAATA TATACACCAT GTACCTACAA
55801 AAATTAAAAA TAAAAAAATA TAAAAATCAA TAGAAAAGTA ATAAAGGTCA
55851 GAGTAGCATT AAATGAAATA CAGAAAAAAA TACAAAGGAT CAGTGAAATG
55901 AGAAGTTGGT TAAAAAAAAA ATAAAATCAA TAAACTGCTA GCTAGACTAA
55951 CCAAGAAAAA AAAGAGAGAT GACTGAAATA AAAATCAGAA ACAAAAAAGG
56001 AGACATAACA ACTAATACCA CAGAAATGAA AAAACCCACC AGAGAACATT
56051 ATGAACAAAT ATAAGCTAAC AAAATGGAAA ACCTAGAGGA AATGGATAAA
56101 TTCCTGGACA CATACAAGAC TGAGTCAGGA AGAAATAGAG AACCTGAACA
56151 GACCAATAAT GAGCAATAAG ATTGAATCAG TAATAAAATA TCTCCTAACA
56201 AAGAAAAGCC CAGGACTGGA TGGCTTCACT GCCATATTCT ACCAAACTCA
```

FIGURE 30

```
56251 TAAAGAAGAA CTAACACCAG TTATCCTCCA ACTATTCCAA AAAATTGAGA
56301 AGGAAGGAAT TCTCCCTAAC TCATTCAATG AAGCCAGCAT TACCCTGATA
56351 CCAAAACCAG ACAAGGATGC GAAAACCACA AAAAAAGAAA ACTATAGGCC
56401 AGTATCCTTG ATGAACACAG ATACAAAATT CCTGAACAAA ATACTAGCAA
56451 ACCTAACCCA ACAGCACATC AAAAAGATAA TACACCATAA TCAAGTGAGT
56501 TTTATACTAG TGATGCAAGG ATGGTTTAAC ATGCACAAAT CAATAAACAT
56551 GATACATCAC ATTAACAGAA TGAAGGACAA AAACAATATG ACCATCTCAA
56601 TAGAAACAGA AAAGACATTT TCTAAAATCC AACATCCCTT TGTGATAAAA
56651 ACTATCAACA AACTAGGCAT AGAAAGAACA TACCTCAATA TAATAGGCCA
56701 TATATGACAA ACCCACAGCT AACATCATAC AGAATGGGGA AAAGGTGAAA
56751 GCCTTTCTTC TTAGAACTGG AACAAGAGAA GGATGCCAAC TTTCACCGCT
56801 CCTATTCAAC ATAGTATTGG AAGTTCTAGC CAGAGTGATT AGGCAAGAGA
56851 AAGAATAAAA GGCATTCAGG CTGGGCGCAG TGGCTCATGC CTGTAATCCC
56901 AGCACTTTGT GGGGCTAAGG CAGGCAGATC ATGAGGTCAG AAAATCGAGA
56951 CCATCCTGGC TAACACAGTG AAACCCCATC TCTACTAAAA ATACAAAAAA
57001 TTAGCCAGGT GTGGTGGCGG GCACCTGTAG TCCCAGCTAC TCAGGAGGCT
57051 GAGGCAGGAG AATGGCATGA ACCCGGGAGG TGGAGCTTGC AGTGAGCTGA
57101 GATCGCACCA CTGCACTCCA GCCTGGGCGA CAGAGTGAGA CTCCATCTAA
57151 AAAAAAAAAA AAAAAAAAAG GCATTCAAAC TGGAAAAGAG AAAGCCAAAC
57201 AGTGCCTCTT TGCAGATGAC GTGATCTTAT ATCTAGAAAA ACCTAAAGAC
57251 TCCACCAAAA AACTCTTAGA TCGATTCAGT AAAGATTCAG TAAAGTTGCA
57301 GGATACAAAA TTAACATACG AAAATTTGTT GTGTTTCTAT ATACCAACAA
57351 TGAAGTAGCT GAAAAAGAAA TCAAGAAGGC AATCCCATTT AAAATGGCTA
57401 CAAAAATAAA ATAAAATACC TGGGAACAAA TGTAACCAAG GAGGTGAAAG
57451 ACCTCTACAA GGAAAACTAC AAAACATTGA TGAAAAAAAT TGAAGACACA
57501 AACAAATGCT CATGGGTCAC AAGAATCAAT ATTGTTAAAG TGGTCATACT
57551 AACCAAAGTT ATTTATGGAT TCAATGCAAA AATACCAATG TAATTTTTCA
57601 CAGAAATATA TACAAAACAA TCCTAAAATT TGTGTGGAAC CAAAAAGGAG
57651 CTCAAGAGC CAAAGCAATA CTAAACAAAA AGAACAAAGC TGGAGGCATC
57701 ACACTATGTC ACTTCAAAAT ATACAGAAAA TATATACAAA ATATATTACA
57751 AGGCTACAGT AACCAAACAG CATGGTATTG GTGTAAAAAT AGACACATAA
57801 ACCAATAGAA CAGAGTAGAG AACCCAGAAA TAAGTCCCCA TATGTAAACC
57851 AACTTATTTT TGACAAAGGG ACCAAGAACA TATACTGGGG AATTGACACC
57901 CTCTTCAATA TATGGTGCAT ATTCATATGC AGATGAACGA AGTTAGACCC
57951 CTATCTCACC ATATACAAAA ATCAACTCAA AATTGATTAA ATACCTAAAC
58001 ATAAGACTCA AAACTATAAA ATTACTAGAA GAAAACATAG GGAAACACTC
58051 CAGGTTATTG GTCTGTGCAG AAGCTCTTTA ATATATAGTT CCATTTGTCT
58101 ATTTTTTGGTT TTGTCACCTG TGCTTTTAAG GTAAAGGAAA GCACAGTGTG
58151 AAGAGACGAC CTGTTGAATG GGAGAAAATA TTTGCAAAAT GTTCATCCAA
58201 CAAGAAACAT ATCTCAAAAG AAGACACAAA TAGCCCACAG GTATATGAAG
58251 AAATGCTCAA CATCACTAAT CAACAAGGAA ATGCAAATTA AAACCACCAA
58301 GAGATACCTA CCATCTTATC CCAGTTAAAA TGACTACTAT TAAAAACACA
58351 CAAAAGCTCT CCCTCTCCCT TTCCCTCTCC CTCTCGTCTC CCTCTCCCCA
58401 CGGTCTCCCT CTCCCTCTCT TTCCACGGTC TCCCTCTGAT GCCGAGCTGA
58451 AGCTGGACTG TACTGCTGCC ATCTCGGCTC ACTGCAACCT CCCTGCCTGA
58501 TTCTCCTGCC TCAGCCTGCC GAGTGCCTGC GATTACAGGC ACGCGCCGCC
58551 ACACCTGACT GGTTTTCGTA TTTTTTTTTG GTGGAGACGG GGTTTCNNNN
58601 NNNNNNNNNN NNNNNNNNNN NNNNNNNNNN NNNNNNNNNN NNNNNNNNNN
58651 NNNNNNNNNN NNNNNNNNNN NNNNNNNNNN NNNNNNNNNN NNNNNNNNNN
58701 NNNNNNNNNN NNNNNNNNNN NNNNNNNNNN NNNNNNNNNN NNNNNNNNNN
58751 NNNNNNNNNN NNNNNNNNNN NNNNNNNNNN NNNNNNNNNN NNNNNNNNNN
58801 NNNNNNNNNN NNNNNNNNNN NNNNNNNNNN NNNNNNNNNN NNNNNNNNNN
58851 NNNNNNNNNN NNNNNNNNNN NNNNNNNNNN NNNNNNNNNN NNNNNNNNNN
58901 NNNNNNNNNN NNNNNNNNNN NNNNNNNNNN NNNNNNNNNN NNNNNNNNNN
58951 NNNNNNNNNN NNNNNNNNNN NNNNNNNNNN NNNNNNNNNN NNNNNNNNNN
59001 NNNNNNNNNN NNNNNNNNNN NNNNNNNNNN NNNNNNNNNN NNNNNNNNNN
59051 NNNNNNNNNN NNNNNNNNNN NNNNNNNNNN NNNNNNNNNN NNNNNNNNNN
59101 NNNNNNNNNN NNNNNNNNNN NNNNNNNNNN NNNNNNNNNN NNNNNNNNNN
59151 NNNNNNNNNN NNNNNNNNNN NNNNNNNNNN NNNNNNNNNN NNNNNNNNNN
59201 NNNNNNNNNN NNNNNNNNNN NNNNNNNNNN NNNNNNNNNN NNNNNNNNNN
59251 NNNNNNNNNN NNNNNNNNNN NNNNNNNNNN NNNNNNNNNN NNNNNNNNNN
59301 NNNNNNNNNN NNNNNNNNNN NNNNNNNNNN NNNNNNNNNN NNNNNNNNNN
59351 NNNNNNNNNN NNNNNNNNNN NNNNNNNNNN NNNNNNNNNN NNNNNNNNNN
59401 NNNNNNNNNN NNNNNNNNNN NNNNNNNNNN NNNNNNNNNN NNNNNNNNNN
59451 NNNNNNNNNN NNNNNNNNNN NNNNNNNNNN NNNNNNNNNN NNNNNNNNNN
59501 NNNNNNNNNN NNNNNNNNNN NNNNNNNNNN NNNNNNNNNN NNNNNNNNNN
59551 NNNNNNNNNN NNNNNNNNNN NNNNNNNNNN NNNNNNNNNN NNNNNNNNNN
59601 NNNNNNNNNN NNNNNNNNNN NNNNNNNNNN NNNNNNNNNN NNNNNNNNNN
59651 NNNNNNNNNN NNNNNNNNNN NNNNNNNNNN NNNNNNNNNN NNNNNTTTGG
59701 ACAATACGGC GCTTTCAAGG GCAGAGCTCC CTGAGCTTTC CACAGTGTAT
59751 GTTGCCCCTG ATTTATTGAG ACTGGGGAGT GGCGATGACT TTTACCAAGT
59801 ATACTGCTTG GAAACATCTT GTTAGCAAGG CGCATCCTGC ACAGCCCTAG
59851 ATCCCTTAAA CCTTGATTTC ATACAACACA TGCTTTTGTG AGCTTCAGGT
59901 TGGGTCAAAG TGGTTTGTTC AAAGTGACTG GGGCAAAGCT ACAGATTAAC
59951 AACATCTCAG CAAAGAAATT GTTGAAAGTA CAGGCCTTTT TCAAAATGGA
```

FIGURE 3P

```
60001 GTCTCTTATG TCTTTCCTTT CTACATAGAC ACAGTAAGAG TCTGATTGCT
60051 CTTTCTTTAG CCTACACTCA CTGAACTGCC CTTCCCCTCC GCTGGGCCAT
60101 GACCATGGAG AACAGGTCCA CTGTCCTCCC TGCGTGGTGC ACCATGGAGG
60151 CTCAGACTCC GTCCTCGAGG CTGGCAAGAA GACAGGGTAA GACATGAGCC
60201 TCCTGATACA GGAGATGTCT GTGGAGCCCA CAGGACTGCA ACCTCACACT
60251 GCAGGGCTGG AGGCACAGAC TGACTATTTA CTATTCTGTG GCCTGGGGGG
60301 CTCAAGGCAC AGAGCTCCTC ATTAGCCAAA GTCACCCAAG TTCCCAACCT
60351 CTAAGGATTT CCTCATAATA ATGCAAGAAG AAGAAAAGTG AGTGCCCGTA
60401 GAAGCTTTGG GGCTCTTCCT CTAATCAGGA GAAAGCTGGT GTGTATTCTT
60451 CACTTCTTTC TTTTCTTTTT AAACATCCAA CTGCTTTAAT TTTCATCTTT
60501 TATTATGGGA AAATATATCA CTTATAAATA TTAAAAAAAA CCCACAAAAA
60551 TAACAGATGC TGGCAAGAAT GTGTAGATAA GGAAACTCAC GTACTGTTGG
60601 GTGTGAATGT AAATTAATAC AGCCATTATG GAAAACAGTA TGGAGATTTC
60651 TCAAAAAAAC CCCAAAAAAC TAAAAATAGA ACTACCTGCC GTGTGATCCA
60701 GCAATCCTCC TACTGAGTAT TTATCCAAAG GAAAGAAAAT CATTATCTCT
60751 AAGGGATACC TGCATCCTCA TGCTTATTGC AGCACTATTC ACAATAACAA
60801 AGGTATGGAT CCACCTAAGT GTCCCTCAAC AGATGAATAG ATAAAGAAAA
60851 CTTAGTATAT ATGCACAACA GAATGCTACT CAGCCATAAA AAAAATGAAG
60901 TCTTATCATT TTCAGCAACA GAGATGGATC TGGAGTTCTT TATCTTAAGT
60951 AAAATAAGCC AGGCCCAGCA AGACAAATAC CACGTTCTCT CTTATGTGGG
61001 AGCTACGAAA GTAGATCTCA TGGAAGTAGA GAGTAGAATG ATAGTTATCA
61051 GAGGCTGGGA AGGGTGTGTA TGTGGTGGGG CAGGGAGGAT AAAAAGAGGT
61101 TGGTTAATGG GTACATAATT AGATAGAAGG AGTAAGTTCT AATGTTTGAT
61151 AACAGAGCAG GGTGACTGTA ATTAACAACA ATGTATTCTG TATTTCAAAT
61201 AGCTAGAAGA GAGGACTTGA AGTGTTCCTG ACACATAGAA ATGACAAATA
61251 CTCATTATAT ATCAATAAAG AAAGTGGTTG CACAATGTAG CGGGTAGGGG
61301 AAGTTACCTG GTTGTTAAAG CCTTAATAAA TATTTATGTA TCTGAAAAAA
61351 AAATCAAAAG ATGGCCAATT TAACCAAAAG AATGCCTCTG GAATAGGCCA
61401 TTGCAGCTAA TCATTGACTA TTTCATTAGC TCATTGGTTC ATTAACTGGC
61451 TCATTGACTG ATACCTTTCT AAAATCTTTT GAATTTCTTG AAGAAAAAAA
61501 CTATGCCACA ATAGTACTGA ACAACTGTCT CCCTCTATCT TACGTTAATC
61551 CAGGAGTGCC CAAAACGGGA TTATTTCAAT TAATCACCAA AGCATATTTG
61601 AATATCTATT TTAAAAGGTT TTCAATTCTG GATTTTAATG CTTCTGAATT
61651 TTAAAAGTAA ATGTAAGTGT GAATTTTACC ATACGTAAAT TAGACTCCAA
61701 ACAAATTGCA CAAAAGTACA ATGGGAAAGT AGGGCCTAGT TTTCAATCAC
61751 AATAGCTACC ACTTTTCAAA CAAGTACCAT GCTATTGTTT AAAAGTTGTA
61801 TATATATTAT TTAATTCTCC CAATGAGTTA GGTATTATTG TTATCTCCAT
61851 CTTACTGATG AAGAGAGTTT TAGTCACTTA GCTTAAGGTC ACACAGCTAA
61901 AAATTGGAGA CTGGACTCAA CCCAAGTCTG TTTGACTATC AGAAGTTGTA
61951 TTTCCGTCTT TAAAAGTTCA CATTTAAGTA GATCTACATT GGCAGTCTCA
62001 TTACTGAGTG CTGCTGCTTC TAATGTGTTT TTCCCTTCTT AGGGACCAGC
62051 ATGAGCGACC TTCTGCTCTC CAGCTCCTGA AGCACTCCTT CTTGGAGAGA
62101 AGTCACTGAA TATACATCAA GACTTTCTTC CCAGTTCCAC TGCAGATGCT
62151 CCCTTGCTTA ATTGTGGGGA ATGATGGCTA AGGGATCTTT GTTTCCCCAC
62201 TGAAAATTCA GTCTAACCCA GTTTAAGCAG ATCCTATGGA GTCATTAACT
62251 GAAAGTTGCA GTTACATATT AGCCTCCTCA AGTGTCAGAC ATTATTACTC
62301 ATAGTATCAG AAAACATGTT CTTAATAACA ACAAAAAACT ATTTCAGTGT
62351 TTACAGTTTT GATTGTCCAG GAACTACATT CTCTATTGTT TTATATGACA
62401 TTTCTTTTTA TTTTTGGCCT GTCCTGTCAA TTTTAATGTT GTTAGTTTAA
62451 AATAAATTGT AAAAACAACT TATATTTTCT TGCTTGGTGA GTAAAGATGC
62501 TTACTTAATT CGTCCAAAGC AGAGCAGAGG AAGGCAGGAA GGTAAGTTAA
62551 AGAGATTCTA GATTCTGTAC TTTGGCAGCA ATCTTAGCCT AAAAGATTCT
62601 AGGAGGCTCA AGGCCTAATA GGGAGGAGGT GAGGGCCTCG GCATTTCATT
62651 ATCAGAGGGC CCCCAAACTC CTCAGATGTC TCTGAGAAAT TGTGCTAGTT
62701 AAGGCGGCAT CATAAACCTT GGGCTCTTTT CTCTGTAATT TATTTGTAGT
62751 GATTTGAAGT TTTTAATCTA TTTGCAGTGA ATCAGGTCAT TTCCATATGC
62801 AGAACTAGCT AAGTCTAAAT CAGCTGGTAG GACAAAAGCT AGGTCTGGTA
62851 AGGGAAGGAT GATTTTTTCCA CAGACCTTTG CTCATTTCAT TTGAATAGTT
62901 ACCTCTGCTG AGGTCATCCT TCAAATACTG CCATTCCCAG AACATTAGTA
62951 GACCTCACAA AAGTGAGCAT GGATGAGTTA GTAGTATTAC AAGCCATTTT
63001 AAGTTGGTGG ATTAAGCAAT ATTTTTTTTA GACTGAGTCT TACTCTACTG
63051 CCCCAGGCTG GAGTGCAGTT GCGTTATCTT GGCTCACTGC AACAACCTCC
63101 GCCTGCTGGG TTCAAGTGAT TCTTTTGCCT CAGCCTCCCA AGTAGCTGGG
63151 ATTACAGTTG CCCACCACCA CGCCCAGCTA ATTTTTGTAT TTTTTGTGGA
63201 AATGGGGTTT CACCATGTTG GCCGAGATGG AGTTTCACTG TGTTGGCCAG
63251 GCTGTCTTGA ACTCCAGACC TCAAGTGATC CACCTGCCTT GGCCTCCCAA
63301 AGTGCTGGGA TTACAGGCGT GAGCCATCGT GCCCAGCCAG GATTAAGCAT
63351 TTTTTATAAG GTTTCCATTG CTGTTGATCT CACTCATCCA CTAAACTTCG
63401 CACCTATTGT TCTTTTTTTT TATTATTATT ATTTGAGATG GAGTCTCACT
63451 CTGTTGCCCA GGCTGGAGTG CAGTGGCGTG ATCTTGGCTC ACCGCAACCT
63501 CTGCCACCTG GGTTCAAGCA ATTTTCCTGT CTCAGCCTGC CAAGTAGCTG
63551 AGATTACTGG GACCTGCCAC TGTGCCTGGC TAATTTGTGT AGTTTTAGTA
63601 GAGATGGGGT TTCACCATCT TGGCCAGGCT GGTCTTGAAC TCCTGACCTC
63651 ATGATCCACC CGCCTTGGCC TCCCAAAGTG TTGGGATTAC AGGCGTGAGC
63701 CATCGCGCCC AGCCAGCACC TATTGCTCTA AGCTATAGCC ACAGATATTT
```

FIGURE 3Q

```
63751 TTATTGGCTG CCGTCATTTC AAGCTGGTAC AACTAAAAAT TAACTTTAGG
63801 AGTATTCTAA TACTGGTATC AGGATTTGTC AAAACAAAGC TGGTTTAGTT
63851 TTTATGAAAT AAATGTGAAA TGCTGTCCAG GTGAGGTAAA AACAGATTTT
63901 ACTCTGGACA TGTAACATTA GATGAGTCTT TGTGGGTATA ACTTTTCTCA
63951 AATTTTTTTT TCATATTTAA GAAATTAAGG GAAGAATATG TCCTTTATTT
64001 TACTTACTTG TATCTCAACA TGACCAGAAA CAACATAATT TTGAAAGGTT
64051 AGGGCTTATT CCTTTTCCAT TTTGGAGGGA TCTTCAGCAT TCTTTCAAAT
64101 CTGAATATTA TATTGGATTT TAAAGCAACT ATTTACAATC AAGCCTGTTA
64151 AACCCTATGG GGAAAGGGCA AAGAGTAAGA CCTGTTAATA CTGTGTATAG
64201 AGATCACCGT AATGGACACA AGAAGTTGGT GTTAACAAGT TTATTCCTAT
64251 TCTACTGAAA TATAAGGGTA CTGAAGACAA TTTTGGAATA TTGAACAGAA
64301 ACTTCAAAAA GCTGAAGTTT TGGCCAGGCA GGGTGGCTCA CCCCTGTAAT
64351 CCCAGCACTT TGGGAGGCCG AGGCAGGTGG ATCACTTGAG GTCAGGAGTT
64401 GGGAGACCAG CCTGGCCAAC ATGCTGAAAC CCCATCTCTA CTAAAAATAC
64451 AAAAAATTAG CTGGGCA
```
(SEQ ID NO: 3)

FEATURES:

| | |
|---|---|
| Start: | 3000 |
| Exon: | 3000-3012 |
| Intron: | 3013-5807 |
| Exon: | 5808-5918 |
| Intron: | 5919-15793 |
| Exon: | 15794-15797 |
| Intron: | 15798-20836 |
| Exon: | 20837-20837 |
| Intron: | 20838-22107 |
| Exon: | 22108-22204 |
| Intron: | 22205-27623 |
| Exon: | 27624-27702 |
| Intron: | 27703-28641 |
| Exon: | 28642-28901 |
| Intron: | 28902-36059 |
| Exon: | 36060-36103 |
| Intron: | 36104-39389 |
| Exon: | 39390-40377 |
| Intron: | 40378-40851 |
| Exon: | 40852-41843 |
| Intron: | 41844-43817 |
| Exon: | 43818-43967 |
| Intron: | 43968-46127 |
| Exon: | 46128-46825 |
| Intron: | 46826-62042 |
| Exon: | 62043-62106 |
| Stop: | 62107 |

SNPs:

| DNA Position | Major | Minor | Domain | Protein Position | Major | Minor |
|---|---|---|---|---|---|---|
| 53 | T | C | Beyond ORF(5') | | | |
| 1841 | C | T | Beyond ORF(5') | | | |
| 1842 | A | G | Beyond ORF(5') | | | |
| 2051 | G | A | Beyond ORF(5') | | | |
| 3573 | G | A | Intron | | | |
| 3686 | C | T | Intron | | | |
| 5117 | A | G | Intron | | | |
| 10079 | A | G | Intron | | | |
| 10160 | C | G | Intron | | | |
| 11517 | A | T | Intron | | | |
| 11592 | A | G | Intron | | | |
| 12727 | A | C | Intron | | | |
| 14671 | - | A | Intron | | | |
| 14694 | A | - | Intron | | | |
| 16395 | T | A | Intron | | | |
| 16857 | G | T | Intron | | | |
| 17666 | T | G | Intron | | | |
| 21891 | T | C | Intron | | | |
| 23148 | T | C | Intron | | | |
| 25026 | A | - | Intron | | | |
| 25028 | A | - | Intron | | | |
| 25193 | A | - | Intron | | | |
| 25223 | A | - | Intron | | | |
| 26689 | T | A | Intron | | | |

FIGURE 3R

| | | | | | | | |
|---|---|---|---|---|---|---|---|
| 35187 | A | G | Intron | | | | |
| 39491 | T | C | Exon | | 237 | S | S |
| 39668 | G | A | Exon | | 296 | R | R |
| 39821 | C | T | Exon | | 347 | D | D |
| 45607 | G | A | Intron | | | | |
| 45740 | A | C | Intron | | | | |
| 45744 | A | C | Intron | | | | |
| 49079 | G | C | Intron | | | | |
| 50768 | G | T | Intron | | | | |
| 51845 | G | A | Intron | | | | |
| 62386 | T | G | Beyond ORF(3') | | | | |

Context:

DNA
Position

53
GCTGGCTGTGAGAGATGTGGACCTGTTTGAGAGTCTTGACATGTTAACAGTG
[T,C]
ACAAACCTGTGGAAGTTCTGTCCCAGCTCCTAAGGCATCATGCGTGAATATGAGCAGTTA
GTCAGCCCAGCTGAAGGGTGTCAATTCAATTGTTATTTACAGAAATCACATGTAAACCGA
GACACAAAGCTTCTTTTTTTACCCTTTTCCCTCCCTCCCATCCTTTTCTTTCTTTCTT
TTCTTTCTTTCTTTTTTCTTTCTTTCTCTCTCTCTTTCTTTCTTTCTCTCTTTCTTTCTT
TCTTTCTTTATTTCTCTGTCTCTTTCTTTTCCCTCTCCTTCCTTCCTTCCTTTCTC

1841
TTTCTTTTGAATTACAATCTTTGATGAAGAAAAGTCCATAAGAGAATATTACTGTGGCTC
ATGACACATTACCCTGTCCCATAGCAACGAAGAGATTCAAATTCAAATGTTTTAGGACAG
AGACCATGATCAACTTGCTCCTTGTCCTAGAATAGGATAAGTAAAGCAAGTTTCATCATT
GTTTCCCTCACTGTAATCTATTAATGGGATTCTCATCATTTAACTTTGGATTTCTCTGAG
CTGATATCTAATGCAAGGGTTCAGTACAACATAGAGAGGATAAGAAGAGACTTGTGCTGT
[C,T]
ATAATAGAGAGGATAAGAAGAGACTTGTTCTGTTGTAAATGGTCCTAAGATCAGCCAGTT
GGGCTTACCAACCACAAAGCCAGGTAAAGAGGAATGAAAAGGCCATGTGGGGCTGGGCG
CGGTGGCTCACGCCTGTAATCCCAGCACTTTGGGAGGCCGAGGCAGGCAGATCACGAGGT
CAGGAGTTCGAGACCATCCTGGCTAACACGGTGAAACCCCGTCTCTACTAAAAATACAAA
AAAATTAGCCGGGCATGGTGGCGGGCCCCTGTAGTCCCAGCTACTCTGGAGGCTGAGGCA

1842
TTCTTTTGAATTACAATCTTTGATGAAGAAAAGTCCATAAGAGAATATTACTGTGGCTCA
TGACACATTACCCTGTCCCATAGCAACGAAGAGATTCAAATTCAAATGTTTTAGGACAGA
GACCATGATCAACTTGCTCCTTGTCCTAGAATAGGATAAGTAAAGCAAGTTTCATCATTG
TTTCCCTCACTGTAATCTATTAATGGGATTCTCATCATTTAACTTTGGATTTCTCTGAGC
TGATATCTAATGCAAGGGTTCAGTACAACATAGAGAGGATAAGAAGAGACTTGTGCTGTC
[A,G]
TAATAGAGAGGATAAGAAGAGACTTGTTCTGTTGTAAATGGTCCTAAGATCAGCCAGTTG
GGCTTACCAACCACAAAGCCAGGTAAAGAGGAATGAAAAGGCCATGTGGGGCTGGGCGC
GGTGGCTCACGCCTGTAATCCCAGCACTTTGGGAGGCCGAGGCAGGCAGATCACGAGGTC
AGGAGTTCGAGACCATCCTGGCTAACACGGTGAAACCCCGTCTCTACTAAAAATACAAAA
AAATTAGCCGGGCATGGTGGCGGGCCCCTGTAGTCCCAGCTACTCTGGAGGCTGAGGCAG

2051
TCTCATCATTTAACTTTGGATTTCTCTGAGCTGATATCTAATGCAAGGGTTCAGTACAAC
ATAGAGAGGATAAGAAGAGACTTGTGCTGTCATAATAGAGAGGATAAGAAGAGACTTGTT
CTGTTGTAAATGGTCCTAAGATCAGCCAGTTGGGCTTACCAACCACAAAGCCAGGTAAAG
AGGAATGAAAAGGCCATGTGGGGCTGGGCGCGGTGGCTCACGCCTGTAATCCCAGCACT
TTGGGAGGCCGAGGCAGGCAGATCACGAGGTCAGGAGTTCGAGACCATCCTGGCTAACAC
[G,A]
GTGAAACCCCGTCTCTACTAAAAATACAAAAAAATTAGCCGGGCATGGTGGCGGGCCCCT
GTAGTCCCAGCTACTCTGGAGGCTGAGGCAGGAGAATGGCGTGAACCCGGGAGGCAGAGC
TTGCAGTGAGCCGAGATCGCGCCACTGCACTCCAGCCTGGGTGACAGAGCAAGACTCCGC
CTCAAAAAAAAAAAAAAAAAAAAAAAAAGGAAAGAAAAGGCCATGTGGAGAGGCACACT
TTGGTTTTTATGACAAGATTGCTCCACTCATCCAAGAGACCATGAAATAAAAGTATCAGC

3573
AAAGGGGAAGAGGGACTTATAGTGGTTCTTGAAGGCTGGATAACAGTGGGAAGGTTTGAT
ATAGGTAGGAAAAGAGTCCAAACAAAGACAAAGAAACAGCCACAGCAAGAAGTATAATGA
AAAGTGTGCCACTGAGCAGCGTGTGACTTTGTGAAAGCTGCCTGACTTTATTGTTTGATT
CGCTTTCTGTTTGAAGCTTCGGGGGCAGAAGGCAAAGCTATACCTAAGAAGGTTTCATGA
AAGAGGTGAGACTTGATCTGACCTTTGAAAAAAGGATGCAATTTGATTTTGTGGAGCAGA
[G,A]
GCCCCTTGCTGGGAGTGAGCATAGCTTATCCCAGGGGCAAACAAGAAACTAGAACTGAAA
GTTCATGTCAGGGAAAAGAGAAACAGAAGGTCAGATACATAAAGAAACTGGGCCCATGGA
GGGGAGAGCCTTAGATGTCAGGCTGAAGGACATCACTTTTTTTTTTCAATAAAACAGACA
CTAAAGAATTTTAAGCCAGAGAATGATGAAGGCCATGTTTTAGGAATATTAACCTGTTCC
TATCGTGTTGGCTACATCTGAGGGAAAAGGCAGGGATCTCTATTAAGAAATTATAGAAGT

3686
ATAATGAAAAGTGTGCCACTGAGCAGCGTGTGACTTTGTGAAAGCTGCCTGACTTTATTG

FIGURE 3S

```
        TTTGATTCGCTTTCTGTTTGAAGCTTCGGGGGCAGAGGACAAAGCTATACCTAAGAAGGT
        TTCATGAAAGAGGTGAGACTTGATCTGACCTTTGAAAAAAGGATGCAATTTGATTTTGTG
        GAGCAGAGGCCCCTTGCTGGGAGTGAGCATAGCTTATCCCAGGGGCAAACAAGAAACTAG
        AACTGAAAGTTCATGTCAGGGAAAAGAGAAACAGAAGGTCAGATACATAAAGAAACTGGG
        [C,T]
        CCATGGAGGGGAGAGCCTTAGATGTCAGGCTGAAGGACATCACTTTTTTTTTTCAATAAA
        ACAGACACTAAAGAATTTTAAGCCAGAGAATGATGAAGGCCATGTTTTAGGAATATTAAC
        CTGTTCCTATCGTGTTGGCTACATCTGAGGGAAAAGGCAGGGATCTCTATTAAGAAATTA
        TAGAAGTGCCCATATGTATGGTGGTAAGAACTAGGGAATGTGTCCTTGGGTGGGGTGTGA
        GAGTGAGCCTAAGAGATGCTGGGAGTGGTGGGTCTAGGAGACATTGTGAAAGAACAATTC

5117    TAGGGTTTCACTTAGCAACTTTGCCTACCACAAACCATTAATCCCAAACATTTGAAGTGA
        TAACTGTTGATCGCTATTAATTTAACTTCATGATCACTCCCTTCTACAAACTAAAGAAGA
        AAGTTTGAGCGATCTAAATTTTTTAAATTATAGGATGGTCTGTAAGGCCCTGTGTTGCTT
        TGATTTCAGTTGTTAGCCAAATTGTGCAGAAATTATCCTCAATTCCCAAGAAATAACTTC
        AGGGGCTTCAGGGCAGTGCACAGATTCAGAGAAAGAAAATACAGTATCGATTGAGCCAGC
        [A,G]
        ATAAGTCTTCAGTACCCTGAAAAATACATGGTAGTTTTTCAGGGTTTAGTTGGAAGAGGC
        CAAGAAGCATCTCCTAATCTTCCACCAGTAGAAGTCTGTAATGATGGGTCATCCTCAGGA
        AACATGGAAGACAGATGTCCTTCCTCTGCGCAGCTCTGGAGAAGAGGATTCCCTAACCTT
        GAACTGCTGATGGCTTTAATGGTTAAAAAGTTCTTACTCATGTCCCAGCACCCTACAGAG
        GGTTTTGCAATGACGACGTAGACATTAAGTATGAAGTGACTAGATTTAAGCTGAACTAAA

10079   GATTTAGTGAAACATGGTAGGATACATTGCTAAACCCAAGTCACAATATAAAATGTCAGA
        AAGTGGATAGAGAAGTGAGAAATGATTTTGCAGCATGGAGAATGGTAAAACCTAATTTCC
        AGAGAAAGGATATTAATGAGAATCAAGATGATGTACTGCAAAGAACCATGGAAAAGCCCA
        GGAATTAGAGGCACCAGGTACTGCAGACGTTGGGAGTTAGCATGAGGTTGAAAAACAGGA
        GGGTTTGGTTGAAAATGTATATAAGGAGCAGAGAGATCCCCAACATTCTACTTCCACTCT
        [A,G]
        TGTAACTACATCACTACTCCTTCCCCACCCTCACAGAAGGCAGGAAGATTTGGTGGAGGA
        TTATTTGAGCTGGAGGAATTCTGGACTTAGTAACAACATACAAAGTGAAAGATGGGAATC
        AGGTCTCAACCTGCAGGCTTAAGTCTGAATATTGACAGAGAGATTGCATCCATCCTCCTT
        CCCCACCTAGCTCCCATATGGCCAGCAGCCCGTTTATACTACTAAGCCAAAAGACTGGAA
        GATTCTTTTCTGGAGATTTAATAACCCCAGAAAATAAACCTACCGATACTGACATTTTTA

10160   ATGATTTTGCAGCATGGAGAATGGTAAAACCTAATTTCCAGAGAAAGGATATTAATGAGA
        ATCAAGATGATGTACTGCAAAGAACCATGGAAAAGCCCAGGAATTAGAGGCACCAGGTAC
        TGCAGACGTTGGGAGTTAGCATGAGGTTGAAAAACAGGAGGGTTTGGTTGAAAATGTATA
        TAAGGAGCAGAGAGATCCCCAACATTCTACTTCCACTCTATGTAACTACATCACTACTCC
        TTCCCCACCCTCACAGAAGGCAGGAAGATTTGGTGGAGGATTATTTGAGCTGGAGGAATT
        [C,G]
        TGGACTTAGTAACAACATACAAAGTGAAAGATGGGAATCAGGTCTCAACCTGCAGGCTTA
        AGTCTGAATATTGACAGAGAGATTGCATCCATCCTCCTTCCCCACCTAGCTCCCATATGG
        CCAGCAGCCCGTTTATACTACTAAGCCAAAAGACTGGAAGATTCTTTTCTGGAGATTTAA
        TAACCCCAGAAAATAAACCTACCGATACTGACATTTTTAAGTTCCCTGAAACACAAGCAT
        TTCACCAGATTAACCCAGCGAAGCCCACCAACAGGTAAATAGCAATATACATAGAGAACT

11517   CCTATTATAAAGCTAAATCAATTAAGGCAGTGTGATATTGCTAGAAATATAGATAAATCC
        ATTACCTGATTTATGACAAAGTTCATGCTGCAGTGAAATAGGGGAAAGAATTTTCAATAC
        ATGGTTCTGGGTTGCATGGATAGTCATATACAAAACAATATGCATGTTGACCCCTACCTC
        ACACCATATACAAAATCAATTCCACATTGATTGGAACAGATCACTGCAGCCTAGCATTCC
        TGAGCCCAAGCAAAACTCCTGCTTCAGTCTCCTGAGTAGCTGGGACTGCAGGCACATGCC
        [A,T]
        CCATTCCCGGATAATTTTTTTTCAATTTGTTTTTGGTAGAGATGGGGTCTTGCTTTGTTGC
        CCAGGGTGTTCTTGAACTCCTGGCTTCAAACAATGTCCCTGCCTCATCCTCCCAAAGTGC
        TGGAATTTATAGATGTGAGCCATTTTGCCTGACCACACTAACCCTTTTGAAAGAAAATGTA
        AGAAAATCTTTGTGACCTTGGAGCTGGCAACAAATATTTTTTTTTTTTTGAGATGGAGG
        CTTGCGCTGTTGCCAGGCTAGAGTGCTGTGGTGCAATCTCGGCTCACTGCAACCTCCAAC

11592   ACAAAGTTCATGCTGCAGTGAAATAGGGGAAAGAATTTTCAATACATGGTTCTGGGTTGC
        ATGGATAGTCATATACAAAACAATATGCATGTTGACCCCTACCTCACACCATATACAAAA
        TCAATTCCACATTGATTGGAACAGATCACTGCAGCCTAGCATTCCTGAGCCCAAGCAAAA
        CTCCTGCTTCAGTCTCCTGAGTAGCTGGGACTGCAGGCACATGCCACCATTCCCGGATAA
        TTTTTTTCAATTTGTTTTTGGTAGAGATGGGGTCTTGCTTTGTTGCCCAGGGTGTTCTTG
        [A,G]
        ACTCCTGGCTTCAAACAATGTCCCTGCCTCATCCTCCCAAAGTGCTGGAATTTATAGATGT
        GAGCCATTTTGCCTGACCACACTAACCCTTTTGAAAGAAAATGTAAGAAAATCTTTGTGA
        CCTTGGAGCTGGCAACAAATATTTTTTTTTTTTTGAGATGGAGGCTTGCGCTGTTGCCA
        GGCTAGAGTGCTGTGGTGCAATCTCGGCTCACTGCAACCTCCAACTCCTGGTTCAAGGG
        ATTCTCCTGCCTCCGCCTCCCGAGTTGCTGGGATTATAAGCATGCACCACCATGCCCGGC

12727   AATATCAAGTGTTGACAAGGATGTAGGGCAACAAGAACTTTCATGCACTGCTGATGGGAG
        AATGAACTGTTAGAATAATTTAGAAAGCTGTCTTTTGGTGTCTGTTAAAGAGAAATATAT
        GCATACTCCATAATCCAGCAATTCTGCTCCTAAATACATACCTAACAGAAATGCATCATA
        TGTTTACCATAAGCTACATATTTATAATGATCATAGCAGCACTATTATAATAGCCCCCAAA
```

FIGURE 3T

```
        TGGAAAATACCCAAGTGCCTATCAAGAATAGAAAGGATACATAAATTGTGGTATATTCAC
        [A,C]
        TAGTGTAAAACTACACATAAATGAGAATGAGAGTGAATGATCTAAAATTACATGCAAAAA
        TACAGATGAATCTCACAAATACACTGTTGAGCAAAAGAAACCAGACATAAAAAATTAAAT
        CCTGTATGGGTCTATTTATATAAAAACAAAAGGAGGAATAACAAAGCTAATCTATGGTGT
        TAGAATTCAGAATAGCACTTGCATGAGAGTGTTCTTTGGGGATATTGGTAGTGTTCTTTT
        ATTTGATCTGGGTCCTGGATACACAAATGTATTGGGTTTATTAAAATTAATCTATACACA

14671   GGCTCACTGCAACCTTCACCTCCTGGGTTCAAGTGATTCTTCTGCCTCAGCTTCCTGAGT
        AACTGGGGTTACAGGCATGCACCACCATGTCTGGCTAATTTTTTGTATTTTTAGTAGAGAC
        AGGGTTTCACCATGTTGACCAGGCTGGTCTCAAACCCTTGACCTTAGGAGATCCATCCAC
        CTTGGCCTCCCAAAGTGTTAGGATTACAGGCGAGAGCCACTGTGCCCGGCCTATACCTTC
        CTCTTAATTTCTCTGTGAACTTAAAATGTCCCTAAAAATAAAGTCTATTCAAACAAACAT
        [-,A]
        CAAACAAACAAACAAACAAACAAGGGTTTGGGGGTTTGTTCTGGAAAATAAAACAGTTAT
        ACAAGAAAGAAAGCATAATCATACTATATTACAATTGTACTACTACATAGTACAATATCC
        TCATAATCAAAATTAGCCATTGACTATTGATTTAACAGCAAAGAAGGTAAATGTATTGGG
        AGGATGGAGGCAGGGCATAAGAACATTAAATTATTAACTGCCATAATAAGTCAATAGATG
        ATGCCTCACTTTGATGAATCAAGAGACAGCATGATAACTATGCAGAAATACGGAAGAAAA

14694   TGGGTTCAAGTGATTCTTCTGCCTCAGCTTCCTGAGTAACTGGGGTTACAGGCATGCACC
        ACCATGTCTGGCTAATTTTTGTATTTTTAGTAGAGACAGGGTTTCACCATGTTGACCAGG
        CTGGTCTCAAACCCTTGACCTTAGGAGATCCATCCACCTTGGCCTCCCAAAGTGTTAGGA
        TTACAGGCGAGAGCCACTGTGCCCGGCCTATACCTTCCTCTTAATTTCTCTGTGAACTTA
        AAATGTCCCTAAAAATAAAGTCTATTCAAACAAACATACAAACAAACAAACAAACAAACA
        [A,-]
        GGGTTTGGGGGTTTGTTCTGGAAAATAAAACAGTTATACAAGAAAGAAAGCATAATCATA
        CTATATTACAATTGTACTACTACATAGTACAATATCCTCATAATCAAAATTAGCCATTGA
        CTATTGATTTAACAGCAAAGAAGGTAAATGTATTGGGAGGATGGAGGCAGGGCATAAGAA
        CATTAAATTATTAACTGCCATAATAAGTCAATAGATGATGCCTCACTTTGATGAATCAAG
        AGACAGCATGATAACTATGCAGAAATACGGAAGAAAATACCAAAAGAAACAGCTAAAAGT

16395   TTTTTTTTGAGACAGAGTCTCGCTCTGTCGCCCAGGCTGGAGTACAGTGGCGCGATCTCG
        GCTCACTGCAAGCTCCGCCTCCCGGGTTCACGCCATTCTCCTGCCTCAGCTTCCCGAGTA
        GCTGGGACTGCAGGGGCCCGCCACTACGCCTGGCTAATTTTTTGTATTTTTAGTAGAGAC
        GGGGTTTCTCCGTGTTAGCCAGGATGGTCTCGATCTCCTGACCTCGTGATCCACCCGCCT
        TGGCCTCCAAAAGTGCTGGGATAACAGGCGTGAGCCACCGCGCCTGGCAAAACTTTTTTT
        [T,A]
        AAAACCTTTCATTAGGTGTTTTTTCTTATTGTAGCCGAAATAAAGTTTAAACTCCTTTTT
        GAGGGAGAAATGGACTTTTTTCAGTATTATATTTGCCTTTCCTTCCCTAGTGGTTTAACTG
        GGGTTTAAATCCCTTTCACTCTTTTCTTTAAATGAAAGCTTTGTTTTCTTTTTGGTTGTC
        TGAAATAGGTTTTTATAGTTTACAAATATAAGCAGCTGCCTTGCATGTAGGACAGCTCCA
        GAGAGGCTCGTTATAGACTCGCCCAGTCATCTTTTTTCACCTGAGGAGAATCTTCTTTCA

16857   TGTTTTCTTTTTGGTTGTCTGAAATAGGTTTTTATAGTTTACAAATATAAGCAGCTGCCT
        TGCATGTAGGACAGCTCCAGAGAGGCTCGTTATAGACTCGCCCAGTCATCTTTTTTCACC
        TGAGGAGAATCTTCTTTCAAAATTTTATCATAGGCTGGATATGGTGGCTCATGTCTGTGA
        TCTCGGCACTTGGGGAGGCTGAAGTGGGAAGATCCCTTGAGTCCAGGCATTCGAGACACC
        CCTGGGCAACATAATAAGACTTTGTCTCTACAAAAAAATTAAAAAATTAGCTGGTTATGG
        [G,T]
        GGCGTGCCTCTGTAGTTCCAGTTACTTCCTGGAGGCTGAGGTGGGAGAACCACTTGAACA
        CAGGAGTTTGAGGCTGCAGTGAACTATAATTGTGCTGCTGCATTCCAGCCTCGGCGACAG
        AGTGAGCTCCCATGTCTCTAAAATATAAAAATAAAAAAACTTTAATCACGTCTGATTTCC
        ATCGTGCCTTTACATTCTGTATGTTTGGTATGCTGTTGTCTGCAGGCTAGAATGCGATGC
        TCTATTTCTTATCCATCTATCAGCTCCCGTGGTGTTGTCAATGGTTTATGAAATCCATCT

17666   TTTGATTGTGATACTTATGGTTTTTCAGTTTGTTCCAGGGTTTAAATTTTTGTCAGGTAC
        TTATAGGGATCACACATCTTTTATTATTATTTTTTCTATGCAAAACTTATCAATTAGGTT
        TGAGTATCCTTTCCCTTTATTTTGCTCATTAATTCTTTTTTTTTCTGGTTCTTGTTGA
        AATTCATTGTTTCAAACTTTTCATGCTAACAAGATCACTGAGTGGTCACAACCTCTGGAC
        CCAGATTTCACAGTCTGGGTGTAAATTCTGGCTCTGCCACTGGCTAGCTGTGTGACCTCG
        [T,G]
        GTAAGCTACTTAACTTTTCTGGGCCTCAGGTACAAAATGAAGATAATAGATCCTAACTTT
        AGAGTTGTGAGGATTAAATTAGTTAACCCATTTATGCTTAGTGTTCCATTATTGGAACGG
        TGAGCTTGTGGGGGTTATTTATATCCCACTGCTCAAGGTCATTGCCAAGGTCTGATTTTT
        CACACAAAAAAATTTGCAACCTCCGAGATAAATGGGTTAATATGTGTAACGCATATAGAA
        CAGTGTCTGGTACTATATATGTAAATGCTAGTCATCATTATGGATTTTGTAGGTGGGTAT

21891   TCAGAACGCCGTCATAGGGAAGACTTTAATCAGCTTTGCTGCCTCCTTTCAGTCTAGGGT
        TATATCTGTAGCTTCCACAGGGGCAGGGATTTCCATTCTTGCCATATGTAAATGATGCCC
        CAGGGAGGCATTATGGAAAAGATCATGCTCCTTTGGGGTTGTTCACTGTGACTGTGGCCA
        AAGGATTCTTTCCAGTTACCTACCCAGATGGAATTTGGGGCAGCTTAGCAGCCTGGGCAC
        TGAGATGATAAAGTATAAAATACTGAGTTTCTATGTGTCGATGTGATTTCAGCTTTGCTC
        [T,C]
        TCATTTTTGATTATGCAATTAATCACAACCATGACTGTCTGAGCCTAGTGCTCCAAGGGC
```

FIGURE 3U

```
           AGATACTTTCTTATTATTTTAGTCCTAAATACTTTATCCAATTTAAAAGGAATCCATGGT
           GTAAATCTTTAGCCCAGAAAAATCAACATTCACTCTGCCAACAAACTGGTACATCGAATA
           ACTAATAACTGAGTTTTGAATTTTATGATATTGCAGGAGTTCGACCAAGATGGTGACTGC
           AGTCATTCCACACTGGTTAATGAAGAAGAAGATCCCAGTGGTGGTAGACAGGACTGGCAA

23148    TATTTACAAGGCCATAAGTCTGGAATCTTCCAGAACACCACCCATTTCAAACATGTTATC
           CTGTCACACCGTAAGTGCCCTTGCACTTAACAGACCACAAGGTATTTGCAGATTCTCGCC
           TCAGAGCATAGTTGCCACGGCTATCCCATTTGTCTGTCATCTATTCATCCATAACCTTCT
           TAAAGTAAATGTTTATTTGAACTGCTGCAATTTCTCCCGGGCAATCTTCTGGCTTCTATT
           TCTAGCACTCCAGGGAAGCCGCCCTCTTTGATGCCCGTGTTTCTCATCCCTTCGCACCTC
           [T,C]
           CAGAAGGCTGCAGCTCTCCCGAGTAGCGTCTCCTCCGGGAGGTGGTGCGATGCTGCCCTC
           TCCTGGGCAGCCGCCTGCCTTTCTCACGCCCACTGGGAATCTTCCCTCCCCAGGCTGAGG
           GCCGAGAGTAATTTAGTAACCATTAAAATTATGAAAACCATTAAGCCTGAAAGAGCTAAC
           AGAAAGAAAATAAACCCCGAAACCCTTCAGAACGGTCCTTGCAGTCCTCCTTCGACTTTC
           ATAGACTTCAAAGCCAAGCTCTTAGAAGCCTAATGGTGTCCCAAGCACCTTCCAGGAGGT

25026    AACATTCAGAACATCCAGTCCATAACAGGAAGGCCCCAGGTTGGATTGTCAGGAAGGATT
           CCCATAACTGCATTTCAAAACTGGCTGCTACTGACCCTCAAATCATGCCACGTCTGCCAT
           AACCAGAGAGCCGCTCCCACTATCAATGTAAGAACCCCCTCCCTCTGCTGGTACCCACAT
           CAGCACACAGCATGCCTGCACCTTATCTTTTTTCATGTAACTCACATGCATCAGTCTCTG
           AAGTAAGCTTTCTGAATCTAGCAGCGCAGGAAGCCGGAAATACAGCTGTTTTTTTTTTTT
           [A,-]
           AAGTCTGTGTTGAGCTTCACAATTTAGGAAATCATCAAAATGTGAAGATGGCATCAAAAT
           ATTTTGAACCTCCATGCTCGCAATCCAGACAGATATGCACATCCATTGAAATAGAACAAG
           GACCTCATTGATATATGCTCCTATTATGTACCCACGGAAATTTAACAAATAAAATAAAAT
           AAAATAAAATAAAATAAGGAGACCAAACAGGAAAGTAAGGCTTTTCTGGAGAAAATAATT
           TTTCTTTATTGAAATCAGTTAAGCTGGGCCTGATTTTAAGTTTTTGTTTTAATAATGGTT

25028    CATTCAGAACATCCAGTCCATAACAGGAAGGCCCCAGGTTGGATTGTCAGGAAGGATTCC
           CATAACTGCATTTCAAAACTGGCTGCTACTGACCCTCAAATCATGCCACGTCTGCCATAA
           CCAGAGAGCCGCTCCCACTATCAATGTAAGAACCCCCTCCCTCTGCTGGTACCCACATCA
           GCACACAGCATGCCTGCACCTTATCTTTTTTCATGTAACTCACATGCATCAGTCTCTGAA
           GTAAGCTTTCTGAATCTAGCAGCGCAGGAAGCCGGAAATACAGCTGTTTTTTTTTTTTAA
           [A,-]
           GTCTGTGTTGAGCTTCACAATTTAGGAAATCATCAAAATGTGAAGATGGCATCAAAATAT
           TTTGAACCTCCATGCTCGCAATCCAGACAGATATGCACATCCATTGAAATAGAACAAGGA
           CCTCATTGATATATGCTCCTATTATGTACCCACGGAAATTTAACAAATAAAATAAAATAA
           AATAAAATAAAATAAGGAGACCAAACAGGAAAGTAAGGCTTTTCTGGAGAAAATAATTTT
           TCTTTATTGAAATCAGTTAAGCTGGGCCTGATTTTAAGTTTTTGTTTTAATAATGGTTTT

25193    CTGGTACCCACATCAGCACACAGCATGCCTGCACCTTATCTTTTTTCATGTAACTCACAT
           GCATCAGTCTCTGAAGTAAGCTTTCTGAATCTAGCAGCGCAGGAAGCCGGAAATACAGCT
           GTTTTTTTTTTTTAAAGTCTGTGTTGAGCTTCACAATTTAGGAAATCATCAAAATGTGAA
           GATGGCATCAAAATATTTTGAACCTCCATGCTCGCAATCCAGACAGATATGCACATCCAT
           TGAAATAGAACAAGGACCTCATTGATATATGCTCCTATTATGTACCCACGGAAATTTAAC
           [A,-]
           AATAAAATAAAATAAAATAAAATAAAATAAGGAGACCAAACAGGAAAGTAAGGCTTTTCT
           GGAGAAAATAATTTTTCTTTATTGAAATCAGTTAAGCTGGGCCTGATTTTAAGTTTTTGT
           TTTAATAATGGTTTTGACACTAACAACAACAAATTAATGATCATTTTTCTGACTGGTTAT
           GAATGTCATTTTCACCTCTTCTATAAAGAAAATATATTCGTGGCTATGTTGAAATGTTGT
           CTTTTAATTTCTCTCTATGGTAATATTTTCTGATAGCGTTAATTTACCCTCATTATGTGA

25223    GCACCTTATCTTTTTTCATGTAACTCACATGCATCAGTCTCTGAAGTAAGCTTTCTGAAT
           CTAGCAGCGCAGGAAGCCGGAAATACAGCTGTTTTTTTTTTTTAAAGTCTGTGTTGAGCT
           TCACAATTTAGGAAATCATCAAAATGTGAAGATGGCATCAAAATATTTTGAACCTCCATG
           CTCGCAATCCAGACAGATATGCACATCCATTGAAATAGAACAAGGACCTCATTGATATAT
           GCTCCTATTATGTACCCACGGAAATTTAACAAATAAAATAAAATAAAATAAAATAAAATA
           [A,-]
           GGAGACCAAACAGGAAAGTAAGGCTTTTCTGGAGAAAATAATTTTTCTTTATTGAAATCA
           GTTAAGCTGGGCCTGATTTTAAGTTTTTGTTTTAATAATGGTTTTGACACTAACAACAAC
           AAATTAATGATCATTTTTCTGACTGGTTATGAATGTCATTTTCACCTCTTCTATAAAGAA
           AATATATTCGTGGCTATGTTGAAATGTTGTCTTTTAATTTCTCTCTATGGTAATATTTTC
           TGATAGCGTTAATTTACCCTCATTATGTGAAAAATGCACTTGCTAAGAGCAAGTGTTTTG

26689    CTAGCTACATTTTTATGGTAGCACAAAACATAATATTGGATAACAATGATAGTAAACACT
           ATTATCATTTGCCTGATTGTAAACAAAACTTTTCATTTTGGAATTTTTTACTGTGTTTTT
           TTTTTTAATGCACTTGTTTCATTAAATGGCACAGGTATAAAAATTGAACAACAAAAATGC
           TTTCACTATGGTAGTTCCTATGTATTACACAAATATATCCAAAGTCCTTTAAAATAATAA
           AAATCTACTAATTTAGATAATGATGATAGCTATTAAGCAACTTTCCCAAGGTCACCCAGG
           [T,A]
           AGTGGCAGAAAAGGGATGTCTGATTCACACCTTAACCTTATCCTCCCTGCGATACTCCTT
           CCCCAGCCTTTAATTAGTGGAGCTCATACAGCCATTGCTCCTCCAGGCACAAGCAGATTG
           AGTGAATAAATGGCTCTGACAGATAAATGGATAGAAATGAATACCGGGGCAAGCATTGCG
           TCCTCCCGGAAGGACACGCCTCTCTGCTCCCACATCACCACTTGCTTCTATCACAGTGCT
```

FIGURE 3V

```
              TATCTCACTGCATTCTTTATTTTCTTATCAGCTCTACTAGGGCCTCAGCTGCATCTTGTT

35187     AGGTTGCAGCGAGCTGAGATCATGCCACTATACTCCAGCCTGGGCGACAGAGCGAGACCC
              TGTCTCAAAAAAAAAAAATCTGCAGCTCTCTGGCTTCTTTTGGAAGATGTAGCAGGGCTG
              GACTATCTATCTGGGTTGGATAACATCACTGCGAGCTGGGTAATGATGCCCCTTTAGTTG
              GGCATATGATCTCGATTTACTGCTGTGTCTTCCTGTCCCACATCATCCATTTCTGTGAAC
              TGTTTTGACCCTGGAGACACTGGAGCTTTTGGCTTCAGCTTTAGAAAGTCCAAACTATGC
              [A,G]
              GAAGTGGTGGTGGTGGTGGTTCATGGGGTTTTGGGGATCATTCTGACTTTTTTGGTAAGAA
              GAGAACAACTTGTAAGTTTTATACTACCTAGTAAGTCCCATCTCGTTCCCTAGGTGAGTC
              TTCCTCACACTCACCTTTCAGAGTTTATGGTCGATCTAGTTTAAACAACTGTTGGGAGAC
              ACTTATACAAGAATATTTTCACATTTCTGCACAGTTCAGGCTTTCTAAGCAAAAAACACT
              AGGAAACTAAGTTAAAAGATGACTGAATGTCAGAAACGCCTCCGAAGTTAGTGTATTGCT

39491     TGCCACTGCACCCCAGCCTGGGTGACAGAGCGAGATCTTGTCTCAAGAAGAAAAAAAAGA
              ATTGTGATTTCCAGGATAGCTTTGAACTTTAAAAGCCTTCCTTAAGAGGATATTATAATC
              TCTTTAGACTACTTTAAACGAGTTAGCGTGATATTTATATATGTTTCTGCATTCACAGCT
              TTTTCTGTCTTCCTTTTAGTTCCTTCTGCCACCACTGTCACTCTTGCCCACGCGATCTGG
              TGTCCTTACTATCCCCCAAAATCACAAGTTTCCAAAAGAAAAAGAAAGAAACATTCCAAG
              [T,C]
              CTCACATCTTTTGTGCCTAAGCTCTCAGTGTCTGTTCGTCAATCTGATGAGCTCAGCCCA
              TCAAACGAGCCTCCGGGAGCCCTAGTTAAGTCGTTGATGGATCCGACTCTCAGGTCTTCT
              GATGGCTTCATTTGGTCAAGAAACATGTGCTCTTTTCCTAAGACTAACCATCACAGGCAA
              TGCCTGGAGAAGGAGGAAAACTGGAAATCCAAGGAAATAGAAGAATGTAACAAAATTGAA
              ATCACTCACTTTGAAAAAGGGCAGTCTTTGGTGTCTTTTGAGAATTTGAAGGAAGGCAAT

39668     GCTTTTTCTGTCTTCCTTTTAGTTCCTTCTGCCACCACTGTCACTCTTGCCCACGCGATC
              TGGTGTCCTTACTATCCCCCAAAATCACAAGTTTCCAAAAGAAAAAGAAAGAAACATTCC
              AAGTCTCACATCTTTTGTGCCTAAGCTCTCAGTGTCTGTTCGTCAATCTGATGAGCTCAG
              CCCATCAAACGAGCCTCCGGGAGCCCTAGTTAAGTCGTTGATGGATCCGACTCTCAGGTC
              TTCTGATGGCTTCATTTGGTCAAGAAACATGTGCTCTTTTCCTAAGACTAACCATCACAG
              [G,A]
              CAATGCCTGGAGAAGGAGGAAAACTGGAAATCCAAGGAAATAGAAGAATGTAACAAAATT
              GAAATCACTCACTTTGAAAAAGGGCAGTCTTTGGTGTCTTTTGAGAATTTGAAGGAAGGC
              AATATTCCTGCAGTTAGGGAAGAGGATATTGACTGCCATGGTAGTAAAACGCGAAAACCT
              GAAGAAGAGAACTCTCAATATCTTTTCATCAAGAAAGAATGAGAGTTCAGTAGCCAAAAAC
              TATGAACAAGATCCAGAAATAGTATGTACCATTCCAAGCAAGTTCCAAGAAACCCAGCAT

39821     GTCTGTTCGTCAATCTGATGAGCTCAGCCCATCAAACGAGCCTCCGGGAGCCCTAGTTAA
              GTCGTTGATGGATCCGACTCTCAGGTCTTCTGATGGCTTCATTTGGTCAAGAAACATGTG
              CTCTTTTCCTAAGACTAACCATCACAGGCAATGCCTGGAGAAGGAGGAAAACTGGAAATC
              CAAGGAAATAGAAGAATGTAACAAAATTGAAATCACTCACTTTGAAAAAGGGCAGTCTTT
              GGTGTCTTTTGAGAATTTGAAGGAAGGCAATATTCCTGCAGTTAGGGAAGAGGATATTGA
              [C,T]
              TGCCATGGTAGTAAAACGCGAAAACCTGAAGAAGAGAACTCTCAATATCTTTCATCAAGA
              AAGAATGAGAGTTCAGTAGCCAAAAACTATGAACAAGATCCAGAAATAGTATGTACCATT
              CCAAGCAAGTTCCAAGAAACCCAGCATTCAGAAATAACTCCAAGCCAGGATGAAGAGATG
              AGAAATAATAAAGCTGCTTCAAAAAGAGTTTCATTACATAAAAATGAAGCAATGGAACCA
              AACAATATTTTAGAAGAGTGTACTGTACTTAAAAGCTTTATCCAGTGTAGTCTTTGATGAC

45607     GAGGCAGCCTGGGCAACATAGAGAGACCTCGTCTCCACAAAAATACTTTTAAAAATTAGCC
              TAGTGTGGTGGTACATGCCTGTAGTCCCAGCTACTCAGGACGCTGAGGCAGGAGGATCGC
              TTGAGCCCAGGAATTTGAGGCTGCAGTGAGATATGATCAGGGCCACTGCACTCCAGCCTG
              GGTGACAGAGAGAGACTCTGTCTCCAAAAAAAAAAAAAAAAAAAAAAGAAAGAAAAAGGTA
              GCACGGTGGCTCTACAAAAAGTACACACACACAATTAGCCAGGTGTGGTGGCACACACCT
              [G,A]
              TGATCCTAGCTACGAGCTGCTCAGGAGGCTGAGGTAGGAGGATTGCTTGAACCCAGGAGG
              TTGAGCCTGCAATGAGCTGTGATTGTGCCAATGCACTCCAGCCTGGGCAACAGAGTGAGA
              CCCTGTCTAAAAACAACCAAAAAAAAAAAAAAAAAAAAAAGAAAAGAAATCTCTGAGGCAAG
              TATTGTTACCTCAGTTTTACAGATGAGAAAAACTGAAGTCAAAAGATTACACATTTATCC
              CAAGTTATATAGCTGGGGAAAGATGAAGCCAGGATTCTAGCCAATTCAAGCCACTTGACT

45740     TTTGAGGCTGCAGTGAGATATGATCAGGGCCACTGCACTCCAGCCTGGGTGACAGAGAGA
              GACTCTGTCTCCAAAAAAAAAAAAAAAAAAAAAAAGAAAGAAAAAGGTAGCACGGTGGCTCT
              ACAAAAAGTACACACACACAATTAGCCAGGTGTGGTGGCACACACCTGTGATCCTAGCTA
              CGAGCTGCTCAGGAGGCTGAGGTAGGAGGATTGCTTGAACCCAGGAGGTTGAGCCTGCAA
              TGAGCTGTGATTGTGCCAATGCACTCCAGCCTGGGCAACAGAGTGAGACCCTGTCTAAAA
              [A,C]
              CAACCAAAAAAAAAAAAAAAAAAAAAAGAAAAGAAATCTCTGAGGCAAGTATTGTTACCTCA
              GTTTTACAGATGAGAAAAACTGAAGTCAAAAGATTACACATTTATCCCAAGTTATATAGC
              TGGGGAAAGATGAAGCCAGGATTCTAGCCAATTCAAGCCACTTGACTTTAAGCCAATATG
              ACATCCATCCACCATGTTTCTCATACCCATCTTGGCTCCACTGAAACACTGAATTTGCTT
              AAACACTTTGCATTTAGGAAGGGAGGTATCAACTTAGAGAAAGACAAGGGTTTAGAAAGA

45744     AGGCTGCAGTGAGATATGATCAGGGCCACTGCACTCCAGCCTGGGTGACAGAGAGAGACT
```

FIGURE 3W

```
        CTGTCTCCAAAAAAAAAAAAAAAAAAAAAGAAAGAAAAAGGTAGCACGGTGGCTCTACAA
        AAAGTACACACACACAATTAGCCAGGTGTGGTGGCACACACCTGTGATCCTAGCTACGAG
        CTGCTCAGGAGGCTGAGGTAGGAGGATTGCTTGAACCCAGGAGGTTGAGCCTGCAATGAG
        CTGTGATTGTGCCAATGCACTCCAGCCTGGGCAACAGAGTGAGACCCTGTCTAAAAACAA
        [A,C]
        CAAAAAAAAAAAAAAAAAAAAAAGAAAAGAAATCTCTGAGGCAAGTATTGTTACCTCAGTTT
        TACAGATGAGAAAAACTGAAGTCAAAAGATTACACATTTATCCCAAGTTATATAGCTGGG
        GAAAGATGAAGCCAGGATTCTAGCCAATTCAAGCCACTTGACTTTAAGCCAATATGACAT
        CCATCCACCATGTTTCTCATACCCATCTTGGCTCCACTGAAACACTGAATTTGCTTAAAC
        ACTTTGCATTTAGGAAGGGAGGTATCAACTTAGAGAAAGACAAGGGTTTAGAAAGAGAAG

49079   CAGAAATCCAGAGCTTGGATGCTGATGGTGGTAGAAGCAGTGGGATTGTAAAGGATTCCA
        GAAAATTTCAGAGAAAAGGTGAATCAAGACTTGGTAATGGAGCAGAATGATAGGATTTCA
        CATTTTTGACTCTGGATAATGGGAGAAATCACAGTTGTGAGAGAAGAACAGGGAGGCAGC
        TAAACCCTTCCCACCTCCTGTAAGGAGACATTT
        [G,C]
        AAGCTATGGAATTGCAGCTCAGGAAAGCAATTAAGATTGGAAGGACACATTTAAAAATAA
        TTATAACAGCCAGGTGCAGTGGCTCATGCCTGTAATCCCAGCACTTAGGAAGGCCGAGGT
        GGGGGATCACTTAAGCCCAGGAGTTCAAGATGGAGACCAACCTGGGCCACATGAAGAAA
        CCCCATCTTTACAAAAAAATACAAAAATTAGCCAGGCATGGTGGTGTGTGCCCGTAGTCC
        CAGCTACTCAGGAGGCTGAGGTGAGAGGATGAGAGGATCGCTTGACCCCGGAAGTTGATG

50768   CCCTGTCTCAAAAAAAAAAAAAAAGTGGGTGGGGGAGCGGTGGTAGCTAGAAATGGTATCC
        AGTTCAAGGAAAGGATTTTAAAGGAGAGAGATTTCTGCATATTTTAAAGGCCGGAGAAAG
        GGCCTCCAGATAGTGAAAGAATTTTTTTTTTTTTTTTTTTTCCGAGACGGAGTCTTGCTT
        TGTTACCCAGGCTGGAATGCGGTGGTGTGACCTTGGCTCACTGCAACCTCCGTCCATGGG
        TTCAAGCAATTCTCCTGTCTCAGCCTCCCAAGTAGATGGGACTACAGGCGCCTGCCACTG
        [G,T]
        GGCCAGCTGATGTTTTTGTTTTTTAGTAGAGACGGGGTTTCACCATGTTGGCCAGGCTG
        GTCTCGAACTCCTGACCTCGTGATCCACCCACCTTAGCCTCCCAAAGTGCTGAGATTACA
        GGTGTGAGCCACTGTGCCTTGCTGTATTTTTTTTTTTTTTTACTTTTGAAATGACACAAA
        TATAATACTTTTATACAAAATACTTTTAAGAGTATTTATTTCCATTTTCACCTGGAAAAT
        GATCTGGTGGCCATTGTGCTTTCAAAATTATTAAAAGAGGAGGGGCTTCAAGATGGCTGA

51845   ACATCTTCTTGTGTTTACCTGGAGGGCTGCAGCAGTGTGATGCCAGTTGTACCCAGTGGA
        GTGGCCAGATCCCCAGCATTGTAGCACACATGGTGTCCTGCACCCCAGAAACAACAGTGC
        AGCGCACCAGGGAGGCTGCTCCTGGGACAAAGGGAGCCAAAGCATGTGCTCCCCAGTGCC
        TAAGAACTGCCTACCTGAGGTGGCTATTACAGATAGCAACCCCACCCTTTCTAGCAGCAG
        GGCTGCCACACACATGCTCTGAGGACAGACTCTGCTGCTGTCCACTGCAGCTTCTGCTTA
        [G,A]
        GCTGAAGTGTGTGCCACTGGCAGTGACCCCACCCGCTTCAGCAACAGGGTTGCAGCACAT
        TTGCATGTGCCCTGAGGACTGGCTTTCTTGGCTGCAGCTGCTGCCACCACCAGAAGCCAA
        ACCATGAGCTCCCTGGAACCTGAGAGCCACCTGCCTGAAGCTGCTGCCACTGACGGCAAC
        TCTGCTTCCACCAGTAGCAGGGCTATAGCACACTTGCACATGCCCTAATGACAGGCTCCC
        CTTGCCCACCACCACCGGAGCTGCAGCCACCCAATCATCATGCCAGGGCCCTGGGGATCA

62386   TCCTTCTTGGAGAGAAGTCACTGAATATACATCAAGACTTTCTTCCCAGTTCCACTGCAG
        ATGCTCCCTTGCTTAATTGTGGGGAATGATGGCTAAGGGATCTTTGTTTCCCCACTGAAA
        ATTCAGTCTAACCCAGTTTAAGCAGATCCTATGGAGTCATTAACTGAAAGTTGCAGTTAC
        ATATTAGCCTCCTCAAGTGTCAGACATTATTACTCATAGTATCAGAAAACATGTTCTTAA
        TAACAACAAAAAACTATTTCAGTGTTTACAGTTTTGATTGTCCAGGAACTACATTCTCTA
        [T,G]
        TGTTTTATATGACATTTCTTTTTATTTTTGGCCTGTCCTGTCAATTTTAATGTTGTTAGT
        TTAAAATAAATTGTAAAAACAACTTATATTTTCTTGCTTGGTGAGTAAAGATGCTTACTT
        AATTCGTCCAAAGCAGAGCAGAGGAAGGCAGGAAGGTAAGTTAAAGAGATTCTAGATTCT
        GTACTTTGGCAGCAATCTTAGCCTAAAAGATTCTAGGAGGCTCAAGGCCTAATAGGGAGG
        AGGTGAGGGCCTCGGCATTTCATTATCAGAGGGCCCCCAAACTCCTCAGATGTCTCTGAG
```

Chromosome Map: Chromosome 2

FIGURE 3X

SEQUENCE LISTING

<160> NUMBER OF SEQ ID NOS: 7

<210> SEQ ID NO 1
<211> LENGTH: 4307
<212> TYPE: DNA
<213> ORGANISM: Human

<400> SEQUENCE: 1

```
tttccttgga tttccagttt tccacccagc tctgaagaca ctgttggtac ttaaaaatat      60
ttaactaaga ctgtgtcatt ttgcaggttg ttggatttct tctggaaaag tgagtagata     120
tcaccctttg caattacagc aatcgaaccg caattcatgt agctaattgc aatatccaaa     180
gacaactctt ggcagtcaat agaatccagg ctccccaaat gcaacttcta caaagttcat     240
ggcaaggtga tcttgagcaa gttcaacatt tactgagatc ctaaactttg tgattttagt     300
ggaaaatcag caatacatta tgtgtcacaa atagagagtt caaagaaaca gcagcttttg     360
gacattttaa tgagttctat gccaaaacca gaaagacatg ctgagtcatt gcttgacatt     420
tgtcatgata caaactcttc tccaactgat ttgatgacag ttaccaaaaa tcaaaacatc     480
atcttgcaaa gcatcagcag aagtgaggag ttcgaccaag atggtgactg cagtcattcc     540
acactggtta atgaagaaga agatcccagt ggtggtagac aggactggca acccaggaca     600
```

```
gaaggtgttg agatcactgt aacttttcca agagatgtca gtcctcccca agaaatgagc    660
caagaagact taaaagaaaa gaatctgata aactcatcgc ttcaagaatg ggcacaagca    720
catgcagttt ctcatccaaa tgaaatagaa acggtggagc tcaggaaaaa gaagctgacc    780
atgcggccct tagttttgca aaaagaggaa agttccaggg agctctgcaa tgtgaacttg    840 ggcttttttgc taccaagatc ttgtttagaa ctgaacattt ccaagtctgt aaccagagaa    900
gatgctcctc attttctgaa ggagcagcaa agaaaatctg aagagttttc gacctctcat    960
atgaagtaca gtggccgaag catcaagttc cttctgccac cactgtcact cttgcccacg   1020
cgatctggtg tccttactat ccccccaaaat cacaagtttc caaagaaaaa agaaagaaac   1080
attccaagtc tcacatcttt tgtgcctaag ctctcagtgt ctgttcgtca atctgatgag   1140
ctcagcccat caaacgagcc tccgggagcc ctagttaagt cgttgatgga tccgactctc   1200
aggtcttctg atggcttcat ttggtcaaga aacatgtgct cttttcctaa gactaaccat   1260
cacaggcaat gcctggagaa ggaggaaaac tggaaatcca aggaaataga gaatgtaac    1320 aaaattgaaa tcactcactt tgaaaaaggg cagtctttgg tgtcttttga gaatttgaag   1380
gaaggcaata ttcctgcagt tagggaagag gatattgact gccatggtag taaaacgcga   1440
aaacctgaag aagagaactc tcaatatctt tcatcaagaa agaatgagag ttcagtagcc   1500
aaaaactatg aacaagatcc agaaatagta tgtaccattc caagcaagtt ccaagaaacc   1560
cagcattcag aaataactcc aagccaggat gaagagatga aaataataa agctgcttca   1620 aaaagagttt cattacataa aaatgaagca atggaaccaa acaatatttt agaagagtgt   1680
actgtactta aaagcttatc cagtgtagtc tttgatgacc ccattgataa actcccagaa   1740
ggttgtagca gcatggagac aaacataaaa atatcaatag cagaaagagc caaaccagaa   1800
atgagtagga tggtgcctct tatccacatc accttccctg tggatggaag ccccaaggaa   1860
ccagtgatag ccaaaccaag cctccaaaca agaaagggaa ccattcataa caaccatagt   1920
gtcaacatac ctgtacacca agaaaatgac aagcataaga tgaattccca taggagcaga   1980
cgtatcacca ataaatgtcg atcttcacac agtgagagga agagcaatat cagaacaaga   2040
ctttctcaga aaaaaacaca tatgaaatgc ccaaagactt catttggcat taaacaagag   2100
cacaaagtct taatttctaa agaaaagagt tccaaggctg tacatagcaa cctacatgac   2160
attgaaaatg gtgatggtat ttcagaacca gactggcaga taaagtcttc aggaaatgag   2220
tttctatctt ccaaagatga aattcatccc atgaacttgg ctcagacacc tgagcagtcc   2280
atgaaacaga tgaattccc tcctgtctca gatttatcca ttgttgaaga gtttctatg    2340 gaagagtcta ctggtgatag agacatttct aacaatcaaa tactcaccac aagcctcaga   2400
gatctgcaag aacttgaaga gctacatcac cagatcccat ttatcccttc agaagacagc   2460
tgggcagtgc ccagtgagaa gaattctaac aagtatgtac agcaagaaaa gcagaataca   2520
gcatctctta gtaaagtaaa tgccagccga attttaacta atgatctaga gtttgatagt   2580
gtttcagatc actctaaaac acttacaaat ttctctttcc aagcaaaaca agaaagtgca   2640
tcttcccaga catatcaata ttgggtacat tatttggatc atgatagttt agcaaataag   2700
tcaatcacat atcaaatgtt tggaaaaacc ttaagtggca caaattcaat ttcccaagaa   2760
attatggact ctgtaaataa tgaagaattg acagatgaac tattaggttg tctagctgca   2820
gaattattag ctcttgatga aaagataac aactcttgcc aaaaaatggc aaatgaaaca   2880
gatcctgaaa acctaaatct tgtcctcaga tggagaggaa gtaccccaaa agaaatgggc   2940
```

-continued

```
agagagacaa caaaagtcaa aatacagagg catagtagtg ggctcaggat atatgacagg    3000
gaggagaaat ttctcatctc aaatgaaaag aagatatttt ctgaaaatag tttaaagtct    3060
gaagaaccta tcctatggac caagggtgag attcttggaa agggagccta cggcacagta    3120
tactgtggtc tcactagtca aggacagcta atagctgtaa acaggtggc tttggatacc     3180 tctaataaat tagctgctga aaaggaatac cggaaactac aggaagaagt agatttgctc    3240
aaagcactga aacatgtcaa cattgtggcc tatttgggga catgcttgca agagaacact    3300
gtgagcattt tcatggagtt tgttcctggt ggctcaatct ctagtattat aaaccgtttt    3360
gggccattgc ctgagatggt gttctgtaaa tatacgaaac aaatacttca aggtgttgct    3420
tatctccatg agaactgtgt ggtacatcgc gatatcaaag gaaataatgt tatgctcatg    3480
ccaactggaa taataaagct gattgacttt ggctgtgcca gcgtttggc ctgggcaggt     3540 ttaaatggca cccacagtga catgcttaag tccatgcatg ggactccata ttggatggcc    3600
ccagaagtca tcaatgagtc tggctatgga cggaaatcag atatctggag cattggttgt    3660
actgtgtttg agatggctac agggaagcct ccactggctt ccatggacag gatggccgcc    3720
atgttttaca tcggagcaca ccgagggctg atgcctcctt taccagacca cttctcagaa    3780
aatgcagcag actttgtgcg catgtgcctg accagggacc agcatgagcg accttctgct    3840
ctccagctcc tgaagcactc cttcttggag agaagtcact gaatatacat caagactttc    3900
ttcccagttc cactgcagat gctcccttgc ttaattgtgg ggaatgatgg ctaagggatc    3960
tttgtttccc cactgaaaat tcagtctaac ccagtttaag cagatcctat ggagtcatta    4020
actgaaagtt gcagttacat attagcctcc tcaagtgtca gacattatta ctcatagtat    4080
cagaaaacat gttcttaata acaacaaaaa actatttcag tgtttacagt tttgattgtc    4140
caggaactac attctctagt gttttatatg acatttcttt ttattttgg cctgtcctgt     4200 caatttaat gttgttagtt taaaataat tgtaaaaaca ccttaaaaaa aaaaaaaaa       4260 aaaaaaaaaa aaaacatgtc ggccgcctcg gcccagtcga ctctaga                  4307
```

```
<210> SEQ ID NO 2
<211> LENGTH: 1167
<212> TYPE: PRT
<213> ORGANISM: Human

<400> SEQUENCE: 2

Met Pro Lys Pro Glu Arg His Ala Glu Ser Leu Leu Asp Ile Cys His
 1               5                  10                  15

Asp Thr Asn Ser Ser Pro Thr Asp Leu Met Thr Val Thr Lys Asn Gln
                20                  25                  30

Asn Ile Ile Leu Gln Ser Ile Ser Arg Ser Glu Glu Phe Asp Gln Asp
            35                  40                  45

Gly Asp Cys Ser His Ser Thr Leu Val Asn Glu Glu Asp Pro Ser
        50                  55                  60

Gly Gly Arg Gln Asp Trp Gln Pro Arg Thr Glu Gly Val Glu Ile Thr
65                  70                  75                  80

Val Thr Phe Pro Arg Asp Val Ser Pro Gln Glu Met Ser Gln Glu
                85                  90                  95

Asp Leu Lys Glu Lys Asn Leu Ile Asn Ser Ser Leu Gln Glu Trp Ala
                100                 105                 110

Gln Ala His Ala Val Ser His Pro Asn Glu Ile Glu Thr Val Glu Leu
            115                 120                 125

Arg Lys Lys Lys Leu Thr Met Arg Pro Leu Val Leu Gln Lys Glu Glu
```

-continued

```
            130                 135                 140
Ser Ser Arg Glu Leu Cys Asn Val Asn Leu Gly Phe Leu Leu Pro Arg
145                 150                 155                 160

Ser Cys Leu Glu Leu Asn Ile Ser Lys Ser Val Thr Arg Glu Asp Ala
                165                 170                 175

Pro His Phe Leu Lys Glu Gln Gln Arg Lys Ser Glu Glu Phe Ser Thr
            180                 185                 190

Ser His Met Lys Tyr Ser Gly Arg Ser Ile Lys Phe Leu Leu Pro Pro
            195                 200                 205

Leu Ser Leu Leu Pro Thr Arg Ser Gly Val Leu Thr Ile Pro Gln Asn
    210                 215                 220

His Lys Phe Pro Lys Glu Lys Glu Arg Asn Ile Pro Ser Leu Thr Ser
225                 230                 235                 240

Phe Val Pro Lys Leu Ser Val Ser Val Arg Gln Ser Asp Glu Leu Ser
                245                 250                 255

Pro Ser Asn Glu Pro Pro Gly Ala Leu Val Lys Ser Leu Met Asp Pro
            260                 265                 270

Thr Leu Arg Ser Ser Asp Gly Phe Ile Trp Ser Arg Asn Met Cys Ser
            275                 280                 285

Phe Pro Lys Thr Asn His His Arg Gln Cys Leu Glu Lys Glu Asn
    290                 295                 300

Trp Lys Ser Lys Glu Ile Glu Glu Cys Asn Lys Ile Glu Ile Thr His
305                 310                 315                 320

Phe Glu Lys Gly Gln Ser Leu Val Ser Phe Glu Asn Leu Lys Glu Gly
                325                 330                 335

Asn Ile Pro Ala Val Arg Glu Glu Asp Ile Asp Cys His Gly Ser Lys
            340                 345                 350

Thr Arg Lys Pro Glu Glu Glu Asn Ser Gln Tyr Leu Ser Ser Arg Lys
            355                 360                 365

Asn Glu Ser Ser Val Ala Lys Asn Tyr Glu Gln Asp Pro Glu Ile Val
    370                 375                 380

Cys Thr Ile Pro Ser Lys Phe Gln Glu Thr Gln His Ser Glu Ile Thr
385                 390                 395                 400

Pro Ser Gln Asp Glu Glu Met Arg Asn Asn Lys Ala Ala Ser Lys Arg
                405                 410                 415

Val Ser Leu His Lys Asn Glu Ala Met Glu Pro Asn Asn Ile Leu Glu
            420                 425                 430

Glu Cys Thr Val Leu Lys Ser Leu Ser Ser Val Phe Asp Asp Pro
            435                 440                 445

Ile Asp Lys Leu Pro Glu Gly Cys Ser Ser Met Glu Thr Asn Ile Lys
450                 455                 460

Ile Ser Ile Ala Glu Arg Ala Lys Pro Glu Met Ser Arg Met Val Pro
465                 470                 475                 480

Leu Ile His Ile Thr Phe Pro Val Asp Gly Ser Pro Lys Glu Pro Val
                485                 490                 495

Ile Ala Lys Pro Ser Leu Gln Thr Arg Lys Gly Thr Ile His Asn Asn
            500                 505                 510

His Ser Val Asn Ile Pro Val His Gln Glu Asn Asp Lys His Lys Met
            515                 520                 525

Asn Ser His Arg Ser Arg Arg Ile Thr Asn Lys Cys Arg Ser Ser His
    530                 535                 540

Ser Glu Arg Lys Ser Asn Ile Arg Thr Arg Leu Ser Gln Lys Lys Thr
545                 550                 555                 560
```

-continued

```
His Met Lys Cys Pro Lys Thr Ser Phe Gly Ile Lys Gln Glu His Lys
                565                 570                 575
Val Leu Ile Ser Lys Glu Lys Ser Ser Lys Ala Val His Ser Asn Leu
            580                 585                 590
His Asp Ile Glu Asn Gly Asp Gly Ile Ser Glu Pro Asp Trp Gln Ile
        595                 600                 605
Lys Ser Ser Gly Asn Glu Phe Leu Ser Ser Lys Asp Glu Ile His Pro
    610                 615                 620
Met Asn Leu Ala Gln Thr Pro Glu Gln Ser Met Lys Gln Asn Glu Phe
625                 630                 635                 640
Pro Pro Val Ser Asp Leu Ser Ile Val Glu Glu Val Ser Met Glu Glu
                645                 650                 655
Ser Thr Gly Asp Arg Asp Ile Ser Asn Asn Gln Ile Leu Thr Thr Ser
            660                 665                 670
Leu Arg Asp Leu Gln Glu Leu Glu Leu His His Gln Ile Pro Phe
        675                 680                 685
Ile Pro Ser Glu Asp Ser Trp Ala Val Pro Ser Glu Lys Asn Ser Asn
    690                 695                 700
Lys Tyr Val Gln Gln Glu Lys Gln Asn Thr Ala Ser Leu Ser Lys Val
705                 710                 715                 720
Asn Ala Ser Arg Ile Leu Thr Asn Asp Leu Glu Phe Asp Ser Val Ser
                725                 730                 735
Asp His Ser Lys Thr Leu Thr Asn Phe Ser Phe Gln Ala Lys Gln Glu
            740                 745                 750
Ser Ala Ser Ser Gln Thr Tyr Gln Tyr Trp Val His Tyr Leu Asp His
        755                 760                 765
Asp Ser Leu Ala Asn Lys Ser Ile Thr Tyr Gln Met Phe Gly Lys Thr
    770                 775                 780
Leu Ser Gly Thr Asn Ser Ile Ser Gln Glu Ile Met Asp Ser Val Asn
785                 790                 795                 800
Asn Glu Glu Leu Thr Asp Glu Leu Leu Gly Cys Leu Ala Ala Glu Leu
                805                 810                 815
Leu Ala Leu Asp Glu Lys Asp Asn Asn Ser Cys Gln Lys Met Ala Asn
            820                 825                 830
Glu Thr Asp Pro Glu Asn Leu Asn Leu Val Leu Arg Trp Arg Gly Ser
        835                 840                 845
Thr Pro Lys Glu Met Gly Arg Glu Thr Thr Lys Val Lys Ile Gln Arg
    850                 855                 860
His Ser Ser Gly Leu Arg Ile Tyr Asp Arg Glu Glu Lys Phe Leu Ile
865                 870                 875                 880
Ser Asn Glu Lys Lys Ile Phe Ser Glu Asn Ser Leu Lys Ser Glu Glu
                885                 890                 895
Pro Ile Leu Trp Thr Lys Gly Glu Ile Leu Gly Lys Gly Ala Tyr Gly
            900                 905                 910
Thr Val Tyr Cys Gly Leu Thr Ser Gln Gly Gln Leu Ile Ala Val Lys
        915                 920                 925
Gln Val Ala Leu Asp Thr Ser Asn Lys Leu Ala Ala Glu Lys Glu Tyr
    930                 935                 940
Arg Lys Leu Gln Glu Glu Val Asp Leu Leu Lys Ala Leu Lys His Val
945                 950                 955                 960
Asn Ile Val Ala Tyr Leu Gly Thr Cys Leu Gln Glu Asn Thr Val Ser
                965                 970                 975
```

-continued

```
Ile Phe Met Glu Phe Val Pro Gly Gly Ser Ile Ser Ile Ile Asn
            980                 985                 990
Arg Phe Gly Pro Leu Pro Glu Met Val Phe Cys Lys Tyr Thr Lys Gln
        995                 1000                1005
Ile Leu Gln Gly Val Ala Tyr Leu His Glu Asn Cys Val Val His Arg
    1010                1015                1020
Asp Ile Lys Gly Asn Asn Val Met Leu Met Pro Thr Gly Ile Ile Lys
1025                1030                1035                1040
Leu Ile Asp Phe Gly Cys Ala Arg Arg Leu Ala Trp Ala Gly Leu Asn
        1045                1050                1055
Gly Thr His Ser Asp Met Leu Lys Ser Met His Gly Thr Pro Tyr Trp
            1060                1065                1070
Met Ala Pro Glu Val Ile Asn Glu Ser Gly Tyr Gly Arg Lys Ser Asp
        1075                1080                1085
Ile Trp Ser Ile Gly Cys Thr Val Phe Glu Met Ala Thr Gly Lys Pro
1090                1095                1100
Pro Leu Ala Ser Met Asp Arg Met Ala Ala Met Phe Tyr Ile Gly Ala
1105                1110                1115                1120
His Arg Gly Leu Met Pro Pro Leu Pro Asp His Phe Ser Glu Asn Ala
            1125                1130                1135
Ala Asp Phe Val Arg Met Cys Leu Thr Arg Asp Gln His Glu Arg Pro
        1140                1145                1150
Ser Ala Leu Gln Leu Leu Lys His Ser Phe Leu Glu Arg Ser His
            1155                1160                1165
```

<210> SEQ ID NO 3
<211> LENGTH: 64467
<212> TYPE: DNA
<213> ORGANISM: Human
<220> FEATURE:
<221> NAME/KEY: misc_feature
<222> LOCATION: (1)...(64467)
<223> OTHER INFORMATION: n = A,T,C or G

<400> SEQUENCE: 3

| | | | | | |
|---|---|---|---|---|---|
| gctggctgtg | agagatgtgg | acctgttga | gagtcttgac | atgttaacag | tgtacaaacc | 60 |
| tgtggaagtt | ctgtcccagc | tcctaaggca | tcatgcgtga | atatgagcag | ttagtcagcc | 120 |
| cagctgaagg | gtgtcaattc | aattgttatt | tacagaaatc | acatgtaaac | cgagacacaa | 180 |
| agcttctttt | ttacccttc | cctccctccc | tccatcctt | ttctttcttt | cttttcttc | 240 |
| tttcttttt | ctttctttct | ctctctcttt | cttctttct | ctctttcttt | ctttctttct | 300 |
| ttatttctct | gtctctttct | tttcctctc | cttcttcct | tccttcttt | ctctctctct | 360 |
| ctctttcttt | cttccttcc | tctttttat | acaggatctt | gctctgttgc | ctaggctgga | 420 |
| gtgcagtgat | gcaatcatag | ctcactgtga | cctcaaactc | ctgggctcca | tggatcctcc | 480 |
| tgcctcagcc | tctcgagtag | ctggaactac | aggcacatac | cactatgccc | ggctaatttt | 540 |
| taatttttg | tggagatgga | gtcccactat | attgcccatg | ctggtctcaa | acccctgccc | 600 |
| tcaagctgct | ctcccatctt | ggcctcccaa | gctgtggaga | ttacaggctg | ttttctacta | 660 |
| tatatgccaa | atgcacatgc | atcatcataa | aagtgacttc | acaattgcaa | agtgatgtgc | 720 |
| agtttctaaa | atttgctacc | tattattctt | atgatatctg | gctctttgtt | tcatttcttg | 780 |
| aaatgattac | tgttctggta | gttactggga | atgtcaaata | atttcttgag | tatccagctc | 840 |
| tctaccccca | agatattact | aattatttca | gaaacactg | tcaatgtctg | aaaagcaatt | 900 |
| tataatagtg | ttttcaagtt | atcttaaaat | tactatatgt | caaatgctct | tttaggaggg | 960 |

-continued

| | |
|---|---|
| aggagataaa caatgcactt ttttttaaa taagagggtt aataagcaat ctcttatgtt | 1020 |
| acaattgcag tttcctaaag ctgttactta gttatcttgt catcaaataa gaacagatgg | 1080 |
| cctgagctct ttctcagtac ttcatatgaa ttttgttttg aaaaaaaaag gaggagggag | 1140 |
| cttcaagaac aaaattatag tcaagaatac aagatattgt aaaaggatca gttagtataa | 1200 |
| tggaatgaaa agggaatttt gaagctactt cagcctagtg ttgagaaata gtttggccaa | 1260 |
| ttgataaaag tggagattcc tgggacgtca tcccagagat gttcagtagg tctggattgg | 1320 |
| ggtccagaat actggaaatc aaggtatgcc acttggagac accctaatct aggcagatga | 1380 |
| ggagaggccc caatgagttt atctttactt gttttatgc acccttaaat aattataaaa | 1440 |
| atttttgtcc aaagttggga attctctgca aatatgataa gtggcttgct taaagccata | 1500 |
| tatcaaggta gtggcaaccc caattctcag tcctatgcta tttctttga attacaatct | 1560 |
| ttgatgaaga aaagtccata agagaatatt actgtggctc atgacacatt accctgtccc | 1620 |
| atagcaacga agagattcaa attcaaatgt tttaggacag agaccatgat caacttgctc | 1680 |
| cttgtcctag aataggataa gtaaagcaag tttcatcatt gtttccctca ctgtaatcta | 1740 |
| ttaatgggat tctcatcatt taactttgga tttctctgag ctgatatcta atgcaagggt | 1800 |
| tcagtacaac atagagagga taagaagaga cttgtgctgt cataatagag aggataagaa | 1860 |
| gagacttgtt ctgttgtaaa tggtcctaag atcagccagt tgggcttacc aaccacaaag | 1920 |
| ccaggtaaag aggaatgaaa aggccatgtg ggggctgggc gcggtggctc acgcctgtaa | 1980 |
| tcccagcact ttgggaggcc gaggcaggca gatcacgagg tcaggagttc gagaccatcc | 2040 |
| tggctaacac ggtgaaaccc cgtctctact aaaaatacaa aaaattagc cgggcatggt | 2100 |
| ggcgggcccc tgtagtccca gctactctgg aggctgaggc aggagaatgg cgtgaacccg | 2160 |
| ggaggcagag cttgcagtga gccgagatcg cgccactgca ctccagcctg ggtgacagag | 2220 |
| caagactccg cctcaaaaaa aaaaaaaaaa aaaaaaaag gaaagaaaa ggccatgtgg | 2280 |
| agaggcacac tttggttttt atgacaagat tgctccactc atccaagaga ccatgaaata | 2340 |
| aaagtatcag cttaatttta aagagaagat tctatgccat tccaccattt tgaatcataa | 2400 |
| aagagctagc tgttagcatt agaaaaaaga aatatcaaaa aagtcagcag ttagcttaat | 2460 |
| tattgaaaag aaaaaaatca agtgagctat ttggaatgat aagacaatca tttatcaaaa | 2520 |
| tgttttaatc cttatgactc attgaaaaaa atttaaaaat ataaaaaaa acaacaaaag | 2580 |
| atgtttttat ctttacttga ttttatgtac ccttaaagaa ttataaaaat ttttgtccaa | 2640 |
| agttgggaat tctctgcaaa cctcagaatg ttttagaat ggggatggga ataaagatac | 2700 |
| acagcaaatt cctttatttt aaaatcttgt aaaattgtca tcctctattc acacattttg | 2760 |
| aaatcattat tattatcccc aaactacata agattacttt ttattatt gatgtaaatg | 2820 |
| tttccctctc atattagttt tctttttca acagattcaa ctaaataaac tttaatgttg | 2880 |
| attctgttct tcctagagat cctaaacttt gtgattttag tggaaaatca gcaatacatt | 2940 |
| atgtgtcaca aatagagagt tcaaagaaac agcagctttt ggacatttta atgagttcta | 3000 |
| tgccaaaacc aggtaaatac tttcactcca catgcataat ttcccaaccc aaaaattcct | 3060 |
| gttagatctc tttcttttc tacatctgtt tgatggatcc atttaaagaa atcaagtcca | 3120 |
| cggctatta tggagcagtg actctgtaca aggcccacga ctaggtgctc tgggggatgc | 3180 |
| aaagaagtct aacgcaaggt ttaaactttt gaaatatac agcatggtca ggggcacatc | 3240 |
| acataagtca gagagagctt gctgtaaact tgaaagggga agaggacttt atagtggttc | 3300 |

```
ttgaaggctg gataacagtg ggaaggtttg atataggtag gaaaagagtc caaacaaaga    3360
caaagaaaca gccacagcaa gaagtataat gaaaagtgtg ccactgagca gcgtgtgact    3420
ttgtgaaagc tgcctgactt tattgtttga ttcgctttct gtttgaagct tcggggggcag   3480
aggacaaagc tatacctaag aaggtttcat gaaagaggtg agacttgatc tgacctttga    3540
aaaaaggatg caatttgatt ttgtggagca gaggcccctt gctgggagtg agcatagctt    3600
atcccagggg caaacaagaa actagaactg aaagttcatg tcaggaaaaa gagaaacaga    3660
aggtcagata cataaagaaa ctgggcccat ggaggggaga gccttagatg tcaggctgaa    3720
ggacatcact ttttttttc aataaaacag acactaaaga attttaagcc agagaatgat     3780
gaaggccatg ttttaggaat attaacctgt tcctatcgtg ttggctacat ctgagggaaa    3840
aggcagggat ctctattaag aaattataga agtgcccata tgtatggtgg taagaactag    3900
ggaatgtgtc cttgggtggg gtgtgagagt gagcctaaga gatgctggga gtggtgggtc    3960
taggagacat tgtgaaagaa caattcacag aactgcgaga tgtgatgttg acagcggaga    4020
cacagagaca accgctgaga aacttgagtc aaagatgact aaattttaag gcctggaaag    4080
tgcaggagat ggaaatacaa ccaacaaaat gggagcacat tggaactttc aagtagcaag    4140
tttctgtagg actgggcttg tgggaaagga ccggttgaaa ggttagtttg ggagttctct    4200
acagagagga gattgtgagg acatgatggt gggtgaggtc attgagggac tgatgagagt    4260
gagaaaattg cagagggctg agccgaggag gtgcacccgc agatagagag gagcggtggg    4320
gacatcagga ctcaggaagt gagaggagga ggagaatcag aagagagttg cgggaagaaa    4380
ggagcaggaa acaatgttaa attggaaaag agattacaaa gcagatgtgg taaggatgtg    4440
agacgtttca atggcaggat gtaggcagaa gatagattgc agagagtaaa gaaggaaaat    4500
atgatgaaga aatggaaagt ctgggtatag atcacttgtt caattttgtt tccactacaa    4560
gataaatgga ggagccactg aaagagggg agttttgtt gaaagaagcc aatgcttatt       4620
agaagaagcc aggatagcag gagggatac atatgagagc aatgtcccta gggtacaaac     4680
tgggagtctg ctgtttggtg ttaggaactc tgtccattta atgtggcttt aatcactaga    4740
taggaagtgt gttcagagga gctgagtgtc tttgtcctgg gcaactatag agcaaatgtg    4800
atttccagct tatcattagg gtttcactta gcaactttgc ctaccacaaa ccattaatcc    4860
caaacatttg aagtgataac tgttgatcgc tattaattta acttcatgat cactcccttc    4920
tacaaactaa agaagaaagt ttgagcgatc taaattttt aaattatagg atggtctgta      4980
aggccctgtg ttgctttgat ttcagttgtt agccaaattg tgcagaaatt atcctcaatt    5040
cccaagaaat aacttcaggg gcttcagggc agtgcacaga ttcagagaaa gaaaatacag    5100
tatcgattga gccagcaata agtcttcagt accctgaaaa atacatggta gttttttcagg   5160
gtttagttgg aagaggccaa gaagcatctc ctaatcttcc accagtagaa gtctgtaatg    5220
atgggtcatc ctcaggaaac atggaagaca gatgtccttc ctctgcgcag ctctggagaa    5280
gaggattccc taaccttgaa ctgctgatgg ctttaatggt taaaaagttc ttactcatgt    5340
cccagcaccc tacagagggt tttgcaatga cgacgtagac attaagtatg aagtgactag    5400
atttaagctg aactaaaatc tgactcttgt taagttttaa tttctcatac agcttaaaat    5460
ttggtgggtg ctcagatcag ataggatgat cgattcatcc taactctcta aaaaatattt    5520
cacttgctca aaatctcaaa ctacctgttt gatttttttg tccttatgta atagcagtta    5580
ccatcaaagc cttaaaaaaa aatagtaagc catccactcc gtggactctt gtcttcacat    5640
ctcttcttgt gaaaattagt gcttgaagct tcatcaggat cccagaccac tatttcagga   5700
```

-continued

```
aaatctttga caaaatggag ctgattttag aacatagagc tagatcttct tttgaaattg    5760
ctggagatga atcttatcaa aacatactat tatgtttctt ttgatagaaa gacatgctga    5820
gtcattgctt gacatttgtc atgatacaaa ctcttctcca actgatttga tgacagttac    5880
caaaaatcaa aacatcatct tgcaaagcat cagcagaagt gaggtaagag cctcccttta    5940
aagaaacaac ggacagccta ctccatctac tactttattt tgtgttgcttg aatacttcat   6000 aacactcata tattacaatt ttatttttaa gtgtaatcat aaaaaagcat atttggtaag    6060
acactcttct gaaagtttaa tctcagagca gtaattagct agtaaactct gagactcatg    6120
cataagatgt gtgtgtacac gtgtgtgtgt gtgtgtgtgt gtgtatgtgt gtgtgtctta    6180
gtcagttctg gctgctataa caaagtacca tagattgggg agcttataaa cagaaattta    6240
tttcttacag tcctggaagt ctgagatcag ggtgccagca ggtttgagtc tggtgagggc    6300
tgtcttctgg actgcagatt gccaacctct catatgctca cttgatggac agagagctag    6360
ctagtgctct ggggtccctt ttataagagg cactaatccc atcatgagga ctctactttc    6420
ataatctacc tcccaaaggc cctacctcct acttgccatc acattggtag ttaagatttc    6480
aacatataaa ttttggtggg acacaaatat tcagttcttt actctgggtg agcgtgcctg    6540
tgtgtgtgtg tctatgtgtc tccagtacca cagaatattg tttcagctga atccatacta    6600
aataatcaaa tgtaccttcc tttttatgta cattaatatt gaaaggaag tctaggctag     6660 ccgtggtggt ccacaccttg tattagtcca tttcacactg ctatagatac tacctgagac    6720
tgggtaattt ataaacaaaa gaggtttaat tgactcagag ttccacatgg ctggggaggc    6780
cccaggaaac ttacaatcat ggtgggaggc aaagggaag caggcacatc ttcacaaggt     6840
ggtaggagag acagagagag tgcaggggaa actgccactt taaaaccat cagatcttgt     6900 gagaactccc ccactatcac aagaacagta tgggggaaac cgcccccatg atccaatcac    6960
cttctacaaa gtccctccct tgacatgtgg ggattacaat tcaagattag atttgctggg    7020
gaacacagag ccaaatcata tcacacctgt aattccagca gtttgtgagg ctgaagatct    7080
gttgaggcca ggagttctgg actggcatgg gtaacaaaaa gagacctcat ctctactaaa    7140
aataaaaaaa attagctggt catgatggca cacgcctgta gtcgcagcta cttgggaggc    7200
tgaggtggaa gaatcacttg agcccaggag tttcaggcct cagtgagcta tgattgcacc    7260
agtgaactct agcctgggtg acagagcaag accctgtctc aatttttaa aaagaaaga     7320 gacaggcacg gtggctcacg ccagtaatcc cagcactttg ggaggccaag gcaggtggat    7380
cgcctgaggt caggagttca agaccaacct ggccaacacg gtgaaagccc atctctacta    7440
aaaatacaaa aaattagcca ggcttggtgg tgggcacctg taatcccagc tactcaggag    7500
gctgaggcag gaggatcgct tgaaccaggg aggcagaggt tgcagtgagc caagattgtg    7560
ccattgcact ccagcctggg caataagagc gaaactccat tcaaaaaaa aaaggaaaag    7620 aaaaggagat cattaatctg atcatatcaa acccatcaca gggtaccaaa aggaggtgc    7680 ctcctcgtgg ccctggttat cattctgtct atgatgaatg actttacaaa aagtcccta    7740 tagtacagta acagtattag taacaagcat tgcagcccat agaaaccgt ggaatgagac     7800 ccaagatgta caacaaactg gcaacagtga ttgcctacag agagaact ggagatgcaa      7860 tttgcactgt ttactcattt gtaccttttg aatgtttata aaaattaaca tatcccaaat    7920
aaagatccta ctactctata ttttattggt taaaaaaaaa agtccaaaaa atttttttatt   7980 tattttgaga ttgggtctca ttctgttgcc caggccgaag tgccctggca taaacatggc    8040
```

```
tcactggagc ctcaatctcc caggctcaag caatcctcct acctcagcct cctgactagc    8100
tgggactgca ggcacatgcc accacaccca gctaatttaa aaaattttt gaactcctag     8160 cctcaagcaa tcctcctgcc tcggcctcct aaagtagtgg gattacaggc atgagccacc    8220
attgccattt tctaattgga ttatttgctt tctaactgat aggtttagag aagcctttat    8280
atattctagg tatatgcttc ataaaatatt ttctcctagt caagaaaata atttgacttt    8340
ttttcatcct tttaatgttt tattaaaaag aagttttaaa ttttgataaa aaacaacatc    8400
catttttttc tttatggatc atgattttg tgactaggaa ttgttcaccg aagcccagga     8460
cacaatttta tcctatgctg tcttctaaaa gatttatagt ttcacatttt acatttagag    8520
tcataatcca attagagctt tttttttct ttttttttga gatggagtct cacttctgtc     8580
acccaggctg gagtgcagtg gcacgatctc tgctcactgc aacctctgcc tcccaagcaa    8640
ttttcccgtc tctgcctcct gagtagctgg gattaaaggt gcccaccacc acgcctggct    8700 aattttttgta tttttagtag agatgggggtt tcaccatgtt ggccaggcta gtctcgcatt   8760
cctgagctca ggtgatctgc ctgccttggt ttcccaaagt gttgggggtta agtgtgag     8820 ccgccacgcc cagcggaatt tgagttaatt tttacaaagt acaaggttta ggtcgaggta    8880 cgtattttg cctgttgttc ctctatcatt tgttgaaaag accatacttc ctccactgat     8940
ttactttcac atctttgtaa aaaaagaaag aagaaaaag aaaaagaaaa aagatctggt     9000
ccaggtgcag tggcttatgc ctgtactccc agcactttgg gaagccaaga cagtaggatc    9060
actttgtggg ggcaagagtt tgaaaccagc ttgaacaaca tagcaagagc tgtctctaca   9120 agaacttta aaaattagct gggcatggtg gtgtatacct gtagtaccta gctatacagg     9180
aggctgaggc aggataattg cttgagccca ggaaattgag gcctcagtga gccaagacca    9240
tgccactatg ctccagcctg gccaacaaga ggcccaatcc cttaaaaaaa tatatatgtt    9300
gagcttcttt cttcaattaa actactatca attctttttt tttttttttt ttttttgct    9360 gttgttgcca aggctgctgg agtggaatgg ctcgatctcg gctcaccaca acctccgctg    9420
cccgggttca agtgattgtc ctaactcagc ctctggagta gctgggatta caggcatggg    9480
ccaccatgcc cggctaattt tgtatttta gtagagacgg ggtttctcta tgttggtcag    9540
gctggtcttg aactctcgac ctgaggtgat ctgcctgcct cggcctccca gagtgctggg   9600
attacaggca tgagccaccg tacccggcct aaactactat caattctaag atgtgtactt    9660 tgcatttaa cctctttgaa gtcagacatc ttaaaattgt cactgtcaaa ttggtaccgt     9720
tttgtcattt ttagtggtac ataaaacaac agtgtagctt ttaatcaagg acatcttaga    9780
tttagtgaaa catggtagga tacattgcta acccaagtc acaatataaa atgtcagaaa     9840
gtggatagag aagtgagaaa tgattttgca gcatggagaa tggtaaaacc taatttccag    9900
agaaaggata ttaatgagaa tcaagatgat gtactgcaaa gaaccatgga aaagcccagg    9960
aattagaggc accaggtact gcagacgttg ggagttagca tgaggttgaa aaacaggagg   10020
gtttggttga aaatgtatat aaggagcaga gagatcccca acattctact tccactctat    10080
gtaactacat cactactcct tccccaccct cacagaaggc aggaagattt ggtggaggat    10140
tatttgagct ggaggaattc tggacttagt aacaacatac aaagtgaaag atgggaatca    10200
ggtctcaacc tgcaggctta agtctgaata ttgacagaga gattgcatcc atcctccttc    10260
cccacctagc tcccatatgg ccagcagccc gtttatacta ctaagccaaa agactggaag   10320
attcttttct ggagatttaa taaccccaga aaataaacct accgatactg acattttaa     10380 gttccctgaa acacaagcat tcaccagat taacccagcg aagcccacca acaggtaaat     10440
```

```
agcaatatac atagagaact tctagtcata tttttagagt catattttat cttccttaat    10500
atgaagagcc aagatagcca agggttatca ggtatttgag gaaagcctcc aatatgaaaa    10560
gtagcatcaa acaacaagg aatgcagatg acatcaggag cacaaagaaa tgaaggggaa     10620
gaaatagttt taagggagg agagaaaaat aaagaaaaaa atgttatcag aaccaaatga     10680
tatgagtttt caagtttaaa gcacccatca ctgcaagacc catcattgca ggacagtgac    10740
taagtacatt accttaaagt attatgaact tttaaagcac tgatgctaca agagaatcct    10800
aaaagttttc aaagaaagag agagagataa tataaaggat aggaaactgg aatggcacca    10860
gatgtcttaa aaataccatt gtaagctaca aatatatgga gctacaaata tatggagcaa    10920
taaaagacct ctacactgaa agtagtaaaa tattgctgaa aattttaaga agacttaaat    10980
aaatagaatg atgtaacatg ttagtggatt ggaaaattta cttttataaa gatgtcaatt    11040
ctgccaaatt cgtttgtaga ttcaacacag tcccaatcaa aacctagcag gtttgtgtgt    11100
gtgtgtaaat taacaagctg attctaaatt catatagaaa ggcaaaaggc caagaatact    11160
gagggcaata ttgaagaaga acaaagtagg aagatttaca ctactagata tcacatccta    11220
ttataaagct aaatcaatta aggcagtgtg atattgctag aaatatagat aaatccatta    11280
cctgatttat gacaaagttc atgctgcagt gaaatagggg aaagaatttt caatacatgg    11340
ttctggggttg catggatagt catatacaaa acaatatgca tgttgacccc tacctcacac    11400
catatacaaa atcaattcca cattgattgg aacagatcac tgcagcctag cattcctgag    11460
cccaagcaaa actcctgctt cagtctcctg agtagctggg actgcaggca catgccacca    11520
ttcccggata atttttttca atttgttttt ggtagagatg gggtcttgct tgttgccca    11580
gggtgttctt gaactcctgg cttcaaacaa tgtccctgcc tcatcctccc aaagtgctgg    11640
aattatagat gtgagccatt tgcctgacc acactaaccc ttttgaaaga aaatgtaaga    11700
aaatctttgt gaccttggag ctggcaacaa atatttttt tttttttgag atggaggctt    11760
gcgctgttgc caggctagag tgctgtggtg caatctcggc tcactgcaac ctccaactcc    11820
ctggttcaag ggattctcct gcctccgcct cccgagttgc tgggattata agcatgcacc    11880
accatgcccg gctaattttt gtatttttag tagagatggg gtttcactat gttggccagg    11940
atggtcttga tctcctgacc tcgtgatcca cccacctcgg cctcctaaag tgctggaatt    12000
acaggcatga gccactgtgc ccggccaaca attttttacaa cagaacacac atcacaaaaa    12060
atgcttgcca taaagaaaa gttaattaaa tgggctatat taaatgaagc atttctttt     12120
atctaaagac atcattaaga taataataag caactcataa ggtgagaaaa gatacttaaa    12180
atgtatgtat ctgacaaagg acctgcattc agaaaaaatt taaaaactcc cacaaattag    12240
gaacagatag gctaatagaa agtgggcaaa aacttgatca gacacttagc aaaaaaaaga    12300
tgtctaaatg gccaacaaaa tatattaaaa gatgctcagc ttttagtcat tagataaatg    12360
taattttaaa caacaatgtg ataacactgc acatccacag aatgattaca attttacaag    12420
ttgggaaata tcaagtgttg acaaggatgt agggcaacaa gaactttcat gcactgctga    12480
tgggagaatg aactgttaga ataatttaga aagctgtctt ttggtgtctg ttaaagagaa    12540
atatatgcat actccataat ccagcaattc tgctcctaaa tacataccta acagaaatgc    12600
atcatatgtt taccataagc tacatattat aatgatcata gcagcactat tataatagcc    12660
cccaaatgga aaatacccaa gtgcctatca agaatagaaa ggatacataa attgtggtat    12720
attcacatag tgtaaaacta cacataaatg agaatgagag tgaatgatct aaaattacat    12780
```

-continued

```
gcaaaaatac agatgaatct cacaaataca ctgttgagca aaagaaacca gacataaaaa   12840
attaaatcct gtatgggtct atttatataa aaacaaaagg aggaataaca aagctaatct   12900
atggtgttag aattcagaat agcacttgca tgagagtgtt ctttggggat attggtagtg   12960
ttcttttatt tgatctgggt cctggataca caaatgtatt gggtttatta aaattaatct   13020
atacacatat ggtaagtgaa cttttctgaa tgtatgctat actaaaatca aaagtaatgg   13080
aaaagggtg gagtagggaa tgtcttcaaa tatctgacac acacaaaaaa gaatatggtt    13140
ttcagccagg catggctgtg gatacctgta cctgtggtcc cagctactca ggaggctgag   13200
atgggaggat aacttgagcc caggagtttg agacagagcct ggacaacatg cctttttttt  13260
ttcttttctt cttttttgga gacagggtct cactctgtca cctaggctgg ggtgcagtgg   13320
ccagtggcat gatcacagct tactgcaacc tccgccttcc aggcttcagc aaacctccca   13380
cctcagcctc ctaagtagct gggattacag gcatgctcca ccaggctccg ctaattttg    13440
catttttttg tagagatggg gtttcaccat gtcacccagg ctgatctcga actcctggcc   13500
tgaagtgatc tgcccacctc agattcccaa agtgctggga ttacagatgt gaaccactgg   13560
cccgaatgaa tgtggttttc aaactaggat tctatgccca aacaaactct cagttaagca   13620
ttagagttga ataaagacat ttttcagaca cagaaatctc aaacatatta cttctgatat   13680
accttttaag gaagctacta agtgctctat taaattgaaa aagtaaataa agaaagagga   13740
aaaaatagga tctgtgactc agaggatcaa gagagaggag ggaatcattg gtataatgaa   13800
gaaggcaggt cccaggactt cagctaatta gcaactctag aaaacaaaga gctcagatga   13860
ttgggggatt ggggtggggg cagggagcag gacagaggag ggaaacagaa cagatattgt   13920
tgtctgataa atttcaccaa gtggcaagac cattgtaggt tgggaagatt taggctttaa   13980
ataaaaggac ataagaaagt aaataaaata aaccaactag aaattaaaaa accaagggat   14040
gaggggaagg aaggatgaat aggcagagca aagaagattt ttagggcact gaaactactc   14100
tgtatgattc tataatggtg gatacaggtc attatacatt tgttcaaacc catagaatgt   14160
acaacaccag gagtgaacct taatgttaac tacagacaac tgtaacaaat gtaccactct   14220
ggagggcgat gttaataatg ggtgaggctg tgcatgtatg ggagcagggg gtatatggga   14280
aatccctata ccttgttctt cttcttcttc ttctttttttt ttttttttggg acggactctt   14340
actctgtcgc ccaggctgga gcgcgatctt ggctcactgc aaccttcacc tcctgggttc   14400
aagtgattct tctgcctcag cttcctgagt aactggggtt acaggcatgc accaccatgt   14460
ctggctaatt tttgtatttt tagtagagac agggtttcac catgttgacc aggctggtct   14520
caaaccttg accttaggag atccatccac cttggcctcc caaagtgtta ggattacagg   14580
cgagagccac tgtgcccggc ctataccttc ctcttaattt ctctgtgaac ttaaaatgtc   14640
cctaaaaata aagtctattc aaacaaacat acaaacaaac aaacaaacaa caagggttt    14700
gggggtttgt tctggaaaat aaaacagtta tacaagaaag aaagcataat catactatat   14760
tacaattgta ctactacata gtacaatatc ctcataatca aaattagcca ttgactattg   14820
atttaacagc aaagaaggta aatgtattgg gaggatggag gcaggcata agaacattaa     14880
attattaact gccataataa gtcaatagat gatgcctcac tttgatgaat caagagacag   14940
catgataact atgcagaaat acggaagaaa ataccaaaag aaacagctaa agtttggaa     15000
gtggttgcct ctgaggaaaa cggtgactgt ttttctcggt ataagtcttt taccattatt   15060
tgattttttt tacatgtgca gtttaatttt gataaaaatt aagtgaaaat taaaaataaa   15120
cggttaaatc aagacttctc tgggacatgg gatgggatga gctaccatgg aaacattcct   15180
```

```
ttttaaatcc tatttgaata ttttagcttt gcgcatttat aaattttcta agtagtttag    15240
tctgcttcct accaaagtgg aatttagtac cctggttccc aacaagggag tgattcccag    15300
cgcccacctc ccacccctcc caccctaggg ggtcatttga caatgtttgc agacatttct    15360
ggtatcatca ctaggggaga atgcaactgg catcttgtgg gtacaagcca gggacgctcc    15420
taaacatcct atcagacaca cgacagcccc cacagccaag aattatctgg tcttgaatgt    15480
caacagtgca gagactgaga aatttgctac atgttgtcac aatattgaag gttgcactgt    15540
gtttggttac taatattata tagtaatcaa aataaaatac ctagagacaa atctttaagg    15600
tgagtgtcat gcataagata ttgataaaca aaacatact ttttattttt atggtctatt     15660
taagcaattt tctttttaaa aggactaact atatcacttc atattaatac attgaaataa    15720
atgtttaaaa acatttttgt agagatgggg tctcactatg ttgcccaggc tggtctcaaa    15780
ctcctggcct cagccaggtg tggtggcatg cacctgtaga accaactact tgggaggctg    15840
aggcaacagg atcattcaag cccaggagtt caaagttaca gtgagctatg atcacaccac    15900
tgcactccag ccaggatgac agagggagag tctgtttcta aaaacaaac aaacaaacaa     15960 acaaacaaac aacatcaaac tcttagtctc aagagattct cccacttctg tctcctaaag    16020
tgcaggaatt acaggtgtga gccaccgtgc ctgatcagta catttttga ggcaacttta     16080 agactttttt ttttttttt ttgagacaga gtctcgctct gtcgcccagg ctggagtaca     16140
gtggcgcgat ctcggctcac tgcaagctcc gcctcccggg ttcacgccat tctcctgcct    16200
cagcttcccg agtagctggg actgcagggg cccgccacta cgcctggcta atttttttgta   16260 tttttagtag agacggggtt tctccgtgtt agccaggatg gtctcgatct cctgacctcg    16320
tgatccaccc gccttggcct ccaaaagtgc tgggataaca ggcgtgagcc accgcgcctg    16380
gcaaaacttt ttttaaaaac ctttcattag gtgtttttc ttattgtagc cgaaataaag     16440
tttaaactcc tttttgaggg agaaatggac ttttttcagta ttatatttgc ctttccttcc   16500
ctagtggttt aactgggggtt taaatcccctt tcactctttt ctttaaatga aagctttgtt  16560 ttcttttttgg ttgtctgaaa taggttttta tagtttacaa atataagcag ctgccttgca   16620
tgtaggacag ctccagagag gctcgttata gactcgccca gtcatctttt ttcacctgag    16680
gagaatcttc tttcaaaatt ttatcatagg ctggatatgg tggctcatgt ctgtgatctc    16740
ggcacttggg gaggctgaag tgggaagatc ccttgagtcc aggcattcga gacacccctg    16800
ggcaacataa taagactttg tctctacaaa aaaattaaaa aattagctgg ttatgggggc    16860
gtgcctctgt agttccagtt acttcctgga ggctgaggtg ggagaaccac ttgaacacag    16920
gagtttgagg ctgcagtgaa ctataattgt gctgctgcat tccagcctcg gcgacagagt    16980
gagctcccat gtctctaaaa tataaaaata aaaaacttt aatcacgtct gatttccatc     17040
gtgcctttac attctgtatg tttggtatgc tgttgtctgc aggctagaat gcgatgctct    17100
atttcttatc catctatcag ctcccgtggt gttgtcaatg gtttatgaaa tccatctatg    17160
tttgggactt gctattctga tgtttctct cttttactca ctcctagatg acactatttc     17220
aattctcctc cttgtggcac ccaagcacat cttaaagtca ttgctggtta gatttataaa    17280
ataagttaga aaattctgag ctgtttctgt ttgagtcttc acttccgtca tcaccttcaa    17340
agtagatctt actccctaca tcctttttga ttgtgatact tatggttttt cagtttgttc    17400
cagggtttaa attttttgtca ggtacttata gggatcacac atctttttatt attattttt   17460 ctatgcaaaa cttatcaatt aggtttgagt atcctttccc tttattttgc tcattaattc    17520
```

```
tttttttttt tctggttctt gttgaaattc attgtttcaa acttttcatg ctaacaagat    17580
cactgagtgg tcacaacctc tggacccaga tttcacagtc tgggtgtaaa ttctggctct    17640
gccactggct agctgtgtga cctcgtgtaa gctacttaac ttttctgggc ctcaggtaca    17700
aaatgaagat aatagatcct aactttagag ttgtgaggat taaattagtt aacccattta    17760
tgcttagtgt tccattattg gaacggtgag cttgtgggggg ttatttatat cccactgctc    17820
aaggtcattg ccaaggtctg attttttcaca caaaaaaatt tgcaacctcc gagataaatg    17880
ggttaatatg tgtaacgcat atagaacagt gtctggtact atatatgtaa atgctagtca    17940
tcattatgga ttttgtaggt gggtatgacc acactgccgg cttccaactt ttcctacagg    18000
accaactgac aaatgaactg agtagctgag attgaccaca gcccagtaat caacatggaa    18060
acttgatgtg agaacctgct gtatgactaa cacttccaaa tgaaggctgc tgttttctca    18120
aagctcagca taaaaatttc actgaatcac tgtaattaaa tgaaatggta gaaatgtgtt    18180
ttgaggtctc ttagagtgtt ctagactaag gatctcacac aaaactatat ataatactaa    18240 aaagaaaaa ttcaaatgac ccataagcat ctaaaactat ctccaacttt tctattaatc    18300
aaagtatgaa cattcaaaca ataataagaa gaccaattcc atctattaca ttaaatataa    18360
taaaatgaaa agtcggccag acgtggtggc aggtgcctgt aatcccagct ctttgggagg    18420
cagagggagg tggattactt gagatcagga gatcgagacc agcctggtaa acatattgaa    18480
acgccatctc tactaaaaat acaaaaaaaa aaaaaaaaaa ttagccaggc atggtggtgg    18540
gcacctgtaa ccccagctac ttgggaggct aaggcaggag aatcgcttga acctggaagg    18600
tggagtttgc agtgagccga gattgcacca cagcactcca gcctgggcaa cagagcaaga    18660
ctctgtctca aaaataaaa aataaaatga aaggggcag gcatggtgg tacatactta    18720 tagttccagc tactcaggag gctgaggtgg gaggatcacc tgagcccagg agttcaaggc    18780
tgcagtgagc catgatagtg ccactgcatt ccagcctgtg tgccagagtg agacactgcc    18840
tcaaaataat aacaataatc atataaacac ctgtgaaaag aagggaaaac aataataatt    18900
aattaattaa ttaaatgaaa aggaatgatg ataagggaga agatatgata tagcacattc    18960
atgcactgct ggtggattat aaatagggat aaactttact tttaaggcaa tgtgtgtaca    19020 aaaaacaac ttttcatag tatttgggtc aataattcca tatctaggga tctactctaa    19080
agaaataatg caaattggg gtattagttg caaatattta ataatactat gtgtaagagt    19140
gaagaatttt aaattaccta ctaagcatca tgggagttac attgtaagac taacggggct    19200
tattaaagaa gtactattgg ctgagcgtgg tggctcacgc ctgtaatccc agcactttgg    19260
gaggccgagg caggcagatc acgaggtcag aagtttgaga ccagcctggc cagcatggtg    19320
aaacctcgtc tctactaaaa atacaaaaat aaggcgggca tggtggcggg tgcctgtagt    19380
ctcagctact cgagaggttg agacaggaga atctcttgaa cccgggaggt ggaggttgca    19440
gtgagctgag gtcgcaccac tgcactccag cctgggcgac agagcaagac tccatctcaa    19500 aaaaaaaaa gaagtactgt tatgaccctc tgatatttgt tgaaggaaag aaattttaaa    19560
ttccattaaa attaaaatga cacttactta gtaaattgct tatgaattta cacttaagtg    19620
aaaaagccag atacaaaaat tatgtgatgc aactatattt ttaaatactt aagagaaaca    19680
caaagaaaat atgattcctg tgttaacagt gttttgctctt tggttgtcag gttataggtg    19740 atttttttaaa ttttgcttta aaaaatactt ttttgtattt ttgtatgttc taggaagaat    19800 aaatcccct ttgtgatttg ataggaagga ggaggaattt gccagataat ggtagaattt    19860
ttgaaataca gagaaggtta agcagtgaaa ttgacaacag cctaggagct gagtgaaccc    19920
```

```
atccgccatt gacaaccagg atagtctgag gtagggcacc caactttttgc caggagatag    19980 aaaacgcttt agaaagtatt aataagggta gtggggagta gggaggaagg gggatggtta    20040
atgggtacaa aaaaaaatag ctagaaagaa tgaataatca acccaatgag agaacaaaaa    20100
gaaaaaaaaa ggaaaagaaa gagtaagaac tagtactgat agcacaacag ggtgactata    20160
gtaataattt aattgtacgt ttaaaaataa ctaaaagtat aattgaatca tttgtaacac    20220
aaaggataaa tgcttgatgt gatgaatact ccatttaccc tgatgtcatt attatgcatt    20280
gcatgcctat atcaaaatat ctcctgtatc ccataaatat atatacctat gtacccataa    20340
aaattaaaaa acaatgttta agtataaact gctgaataaa agtaaggtat gacaactaag    20400
ttattatgat tgaataccta aaatattttt aatgactgta taaatggagg gtttttacttc    20460 tggttttttt ttttgagaca gggtctcact cagttgccca ggctggagtg cagtggtgca    20520
atcatggctc actgcagcct caacctccta tggctcaaat gatcctcgca cctcagcctc    20580
ctgagtagtt gggactacag gcacgtgcca ccatgcctgg ctaattttttg tattttttgt    20640 agagatgggg cttccaccatg ttgtccaggc tggcctcaag caatccaccc atctcggcct    20700
cccaaagtgc taggattata ggtgtgactc accatgcctg gccaggtttt acttttattt    20760
cctttttctt ttcttcttct tttctttttt ctctctctct cttctctctct ctcttttctt    20820 ttctttcttt tgacagggtc tcactctgtc acccaggctg gagtgcagtg gcgtgaccct    20880
agctcaccat agccttgacc tcccgggttc aagccatcct cctgcctcag cctgccaagt    20940
agctgggaca cagggggtgt gccatcacgt ccagctaatt tttgtatttt cagtagagac    21000 agggtttttgc catgttgccc aggctggtct cgaactcctg agctcaagtg atccaccgc    21060 ctcagcctcc caaagtgctg ggattacagg agtgaaccac catgcctggc caactttttat    21120 tatttgctac gacaattaaa atgaacaagg agagaaaagc aagaaatttc ctagctctct    21180
tgggaattaa taaatgagct atcagagaat ttttgtgact cgccacttct ctgacatttc    21240
agatgacagg cttgagcact tagggcaaag acttattgtc catcagtccc cttaaatagg    21300
tagtccacct agatcataga aaccagacag atagttgtaa cattcgggtt gtgatgggat    21360
gttttaacta ttacttggat ctatcatggt tctagaaatt taaaggcaca aaatcatcag    21420
ctataacttc gaatgaagga aactatcaaa acaatgaat tctactaaga aaacatttct    21480 tcttttaaaat gtttggagta cttttttgtaa atcaagttgg ttttcaacta taatgattat    21540
tttctagaga gtgaaaagga agtttaagag gttatgcacc atgatttaga tcagaacgcc    21600
gtcataggga agactttaat cagctttgct gcctcctttc agtctagggt tatatctgta    21660
gcttccacag gggcagggat ttccattctt gccatatgta aatgatgccc cagggaggca    21720
ttatggaaaa gatcatgctc ctttggggtt gttcactgtg actgtggcca aaggattctt    21780
tccagttacc tacccagatg gaatttgggg cagcttagca gcctgggcac tgagatgata    21840
aagtataaaa tactgagttt ctatgtgtcg atgtgatttc agctttgctc ctcattttttg    21900 attatgcaat taatcacaac catgactgtc tgagcctagt gctccaaggg cagatacttt    21960
cttattattt tagtcctaaa tactttatcc aatttaaaag gaatccatgg tgtaaatctt    22020
tagcccagaa aaatcaacat tcactctgcc aacaaactgg tacatcgaat aactaataac    22080
tgagttttga atttttatgat attgcaggag ttcgaccaag atggtgactg cagtcattcc    22140
acactggtta atgaagaaga agatcccagt ggtggtagac aggactggca acccaggaca    22200
gaaggtactg ggctttactc cttgatgtgt ttacaaagat aacattatca tatgggcttc    22260
```

-continued

```
tctccaattt cagaagggct tattgtagaa gtttgaacaa catacactgg agcctatcag     22320
agggtagagg gagtggagga gggagaggat caggaaaaat aattaatggg tactaggctt     22380
aatacctggg tgataaaata atttgtacaa caaaccccat gatacatgtt tacctatgga     22440
acaaacctgc acttgtaccc ctgagcttaa ctcttgcaat aaaagttaaa aaaattataa     22500
taaataagtt tgaaaacaca gaaaaagccc aaggagaag aaaaaccact cacaatacta     22560 cctttttggtc catatctgaa tcagtgggtc taggcagctt gactggccag aataggcaaa     22620
tgctctctgg ctcttttatt ccacctcact ccagctcagc cgacccattc cctgtccatt     22680 tcttttttgtc tgataacatc ctttccccaa tttcttcctc tcagaatctt ccagcggctt    22740
cagtgatcgg ttcccttccg gaaccacacg tgtctccatg agccgttgtc cctgagggga     22800
aggtggggga gtgtacgaga cctgaaagtc cccaagtctc ggtctttat ttacaaggcc      22860 ataagtctgg aatcttccag aacaccaccc atttcaaaca tgttatcctg tcacaccgta     22920
agtgcccttg cacttaacag accacaaggt atttgcagat tctcgcctca gagcatagtt     22980
gccacggcta tcccatttgt ctgtcatcta ttcatccata accttcttaa agtaaatgtt     23040
tatttgaact gctgcaattt ctcccgggca atcttctggc ttctatttct agcactccag     23100
ggaagccgcc ctctttgatg cccgtgtttc tcatcccttc gcacctctca gaaggctgca     23160
gctctcccga gtagcgtctc ctccgggagg tggtgcgatg ctgccctctc ctgggcagcc     23220
gcctgccttt ctcacgccca ctgggaatct tccctcccca ggctgagggc cgagagtaat    23280
ttagtaacca ttaaaattat gaaaaccatt aagcctgaaa gagctaacag aaagaaaata    23340
aaccccgaaa cccttcagaa cggtccttgc agtcctcctt cgactttcat agacttcaaa    23400
gccaagctct tagaagccta atggtgtccc aagcaccttc caggaggtta aatatttcat    23460
ttattctgct ccatatggag ataactcacc atttgggatg ttagtcattc ttttaaactt    23520
gatttgcaat attttcagtt ttcatatggg agccataata cttatgaggc atctccacta   23580
agttatttca gttttaagct tttaacaact tgagttacac atttggaaga agcaattctc   23640
ttcctgataa aattgcatct cacagttgat agagacttca gttgagctag ctactctttc    23700
taatcagaaa ttctgaaata aaagtgtttt agatattatt gtccattata ttcattttaa    23760
atatcggttt aaatctcttt aaatggaccg ggcactgtgg ctcacgcctg taatcccagc    23820
actttgggag gccaaggtgg gcggatcacc tgaggtcagg agttcaagac cagcctggac    23880
aacatggtga aaccccgtct ctactaaaaa tacaaaatta gccgggtgtg gtggtgcgca    23940
cctgtaatcc cagctactcg ggaggctgag gcagaagaat cgtttgaacc cgggaggcgg    24000
aggttgcagt gagctgagat tgtaccattg cactccaacc tgggtgacag agtgaggctc    24060
cgtctcaaaa caaacaaaca aacaaacaaa caaacactat tttctcagaa cataacagac    24120
acaaatctta tagactagaa attgagccta caaatttact gttttcatga gtgaacaaga    24180
gagcctattc cctaaaacta atgggcttaa aaatatttta attcagtata aattcatcag    24240
gatttgtagt tgcaggtata caagaaccta ctcttggttg ggttaaaaag gaagggaatt    24300
ttgaaagata ttaggaagtt catataccat tgaaaaacca gaggagagga actttcttag    24360
tccactcatg ctgccaaaac aaaataccat agactggggg gcttaaatag cagacattta    24420
ttttctcaca gttcttaaga atgggaagtc caagatcaag attctagcag ggatgggttt    24480
ctggtgaggg ctctcttcct ggttgcagat ggctggtctg tccccacgtg gtctttcctc    24540
tgtgcacaca gaggcagagc acaagtgagt gagctctctt cttagaagga cacaaatcca    24600
gctggatcgg ggccccaccc ttgacacctc atgtaacctt cgtttcttcc ttagaggccc    24660
```

-continued

```
catctccaaa taagccacac ttgggggtta gggcttcaac atattaatgt gcggtggggg     24720
acacaaacat tcagaacatc cagtccataa caggaaggcc ccaggttgga ttgtcaggaa     24780
ggattcccat aactgcattt caaaactggc tgctactgac cctcaaatca tgccacgtct     24840
gccataacca gagagccgct cccactatca atgtaagaac cccctccctc tgctggtacc     24900
cacatcagca cacagcatgc ctgcacctta tcttttttca tgtaactcac atgcatcagt     24960
ctctgaagta agctttctga atctagcagc gcaggaagcc ggaaatacag ctgttttttt     25020
tttttaaagt ctgtgttgag cttcacaatt taggaaatca tcaaaatgtg aagatggcat     25080
caaaatattt tgaacctcca tgctcgcaat ccagacagat atgcacatcc attgaaatag     25140
aacaaggacc tcattgatat atgctcctat tatgtaccca cggaaattta acaaataaaa     25200
taaaataaaa taaaataaaa taaggagacc aaacaggaaa gtaaggcttt tctggagaaa     25260 ataattttc tttattgaaa tcagttaagc tgggcctgat tttaagtttt tgttttaata     25320
atggttttga cactaacaac aacaaattaa tgatcatttt tctgactggt tatgaatgtc     25380
attttcacct cttctataaa gaaaatatat tcgtggctat gttgaaatgt tgtcttttaa     25440
tttctctcta tggtaatatt ttctgatagc gttaatttac cctcattatg tgaaaaatgc     25500
acttgctaag agcaagtgtt ttgtctttac ctgtgacaat gcatcctctt ccctggccta     25560
ctgggtagct tgagaggcct tatccacagc aacgtcagca actcacagta ttcaagaggc     25620
agaacaaaga gaacatctgt atgtttctag tggatttcag aatcaatatt ctgtaatctt     25680
ttttccaatt taggaccaac aattaggacg gtggccatta gctcttaaca atatcttaaa     25740
aggcaggtat ttcttacatg tgcttgttat atctttgttt cttggtttga aaagaagtc     25800 agctgatgaa cagactttga agcacattac atttgtttga aaacattctg ggtttattaa     25860
ttcttgacaa ctgcaaaagt acagttgttc ttaaatatgg ttcatgtgaa tacactcagt     25920
tttctaactt ccacagcaaa gaactaaata catttagctt ttgtaccaga acatcctttt     25980
cactgacagt ttagtttta ggaatgtatg ctgtatgttt ttctcactct aacatgtcag     26040
ctaggtgttt gcactcaagg ataactacaa aaatattatg aaagacatcc atcttccttt     26100
caaataggag aacgaccttg agcatgtcat gcaaactcat tgctatcagt ttcttcgtct     26160
ctaaaacgaa aggcttgggt taggtgacct ctaagttcct tccagctcaa taattccaag     26220
tctctcattt tttgctacat agtctggtga tagcctcttt gaaaacttaa aaaacaatgg     26280
actattccag ggaaacttca tttttagaca agtgttccat gcaattgtat agtattagaa     26340
aacatgcaat caagttgtct cctttgagaa acattaagaa aaccaaagct agctacattt     26400
ttatggtagc acaaaacata atattggata acaatgatag taaacactat tatcatttgc     26460
ctgattgtaa acaaaacttt tcattttgga attttttact gtgttttttt ttttaatgca     26520
cttgtttcat taaatggcac aggtataaaa attgaacaac aaaaatgctt tcactatggt     26580
agttcctatg tattacacaa atatatccaa agtcctttaa aataataaaa atctactaat     26640
ttagataatg atgatagcta ttaagcaact ttcccaaggt cacccaggta gtggcagaaa     26700
agggatgtct gattcacacc ttaaccttat cctccctgcg atactccttc cccagccttt     26760
aattagtgga gctcatacag ccattgctcc tccaggcaca agcagattga gtgaataaat     26820
ggctctgaca gataaatgga tagaaatgaa taccggggca agcattgcgt cctcccggaa     26880
ggacacgcct ctctgctccc acatcaccac ttgcttctat cacagtgctt atctcactgc     26940
attctttatt ttcttatcag ctctactagg gcctcagctg catcttgttt atttccctgt     27000
```

-continued

```
tttcagcact aagtgctggg cttggcatat ccttaataaa agttcgttaa atggaaaaaa   27060
ggaatgaatg aacacacctt aaagaacagg caatgttaga atagttcaca ctagtttttt   27120
acataatttt gcttaacatc ttatattgtg agcaagcgcg tattctataa gttggaactt   27180
tctgtcttaa gggttattct ggaaattagt tcatgaaatg agacaggaga tgaccaaaat   27240
tacaaataca agcaaacatc tttggtgtta cataaattat ctcattgaat gctcacaata   27300
gttctgggag ataggtgtcg ttcactttta tagaaggtgg ttctgttttc tccatcctga   27360
ggacaacata gtttgttata aaactttatt ttacatctgt aaaatattat tatatggttt   27420
tttgctcttt aagcaagcat ttatttagga tctatcatat cctgaacagg aaagatacaa   27480
agatggctaa acctcagctc ctgattaatg tccattttgt aatcattaag aagagattag   27540
ccaaacagaa ataagtacg tctcccgctt ccgctggaa ttcattactt tcttccttct   27600
actactgtgg tatgtttcta caggtgttga gatcactgta acttttccaa gagatgtcag   27660
tcctccccaa gaaatgagcc aagaagactt aaaagaaaag aagtaaggaa tattctttga   27720
agtatcagat ttgaaatgaa gtatgaagca atgatagtca tatggcaacc tacattatta   27780
gtaattgaat ccataataat gcttaaaagt agaggtcaca ataaatagta tgtggcagag   27840
gccagatcat aaacactttg gctgtgtggg ccatatggtc tctgttgtga tgattcaact   27900
ctgcaactgt catttgaatg cagccataga caatatgtaa acaaatgagt gtggctgtga   27960
tccaattaaa gctacagaaa aaggctgaag gctggatttg gtccccgggc tgtagtttgc   28020
tgaccctact gcagggcaga gctacttaga atgtggttct gtggtcctgt tactagtcca   28080
tgatgaggtc aggacaggct gcgagggtga ccattaaaaa agttgcaaag caatttggca   28140
aataacttac gttcattgat cgggtagtga aacaaattga gcttatttt ttgcatgtct   28200 tttatttttc ttccattttt atggcaattc atttatattt tacaaaagta tcagttcaca   28260
atgactggaa atttaaatgc tggttcttca tcaaaaatag tttgagaaac actgggctag   28320
tcagtacctg tggagataaa agggtacatc ccccaggcct gcccttggtc tctgatttct   28380
ctgtgcaagg aaatggtgat tgggaaaacg agagtgagct gaaacctaat ccatccaagc   28440
gatggtacag agggctaagg aggccaggag gagtcagcag gtggagatgt cttaccctct   28500
caggattcag cctttccttt cagcagcacc atttggaagt agttcttcaa actttctagt   28560
gatgtcaggc tgaactgagg actggagatc cagaagatgt ggcaactgag ttttaaatca   28620
aacatttccc tcccccttta gtctgataaa ctcatcgctt caagaatggg cacaagcaca   28680
tgcagtttct catccaaatg aaatagaaac ggtggagctc aggaaaaaga agctgaccat   28740
gcggccctta gttttgcaaa aagaggaaag ttccagggag ctctgcaatg tgaacttggg   28800 cttttttgcta ccaagatctt gtttagaact gaacatttcc aagtctgtaa ccagagaaga   28860
tgctcctcat tttctgaagg agcagcaaag aaaatctgaa ggtaagttga acattgaatt   28920
ccacagtgag tccttttggt caacaaatat ttatgtattg tgccaggcac tgttctaaat   28980
gctagagata aagcagtgaa cataccagaa ataaccccca gcccttgtgt aatttacatt   29040
cctgggggtc atgggggtgc gagacagaca ataaactagt aaacaagtaa aatgaaggat   29100
ggcataatgt tccagcagaa agagcactat atgtgcaaat gtttatatat ttgttcaagg   29160
aatagaaggc aaatattttg agaatatctt attgtttaga ttatttcatt gcttatttct   29220
ttaaacattt cagacattat tttgtaaact atacttgata atttcagtat caatatccta   29280
ctgatttgca ctatgggttga cttttttctt gagtgtttga aaatcttcat tgtgagctca   29340
tatttggttg atgtttatct gtgggaatct tgggggccca cgctgtggat gcttttggcc   29400
```

```
agaagtattg aatttacttc taccaggtcc cagggtcatt atggacttga gtctacgtta   29460
gccttattcc tggatcccca agttaatgtg caagtctaag agccaacttc caactacatt   29520
gagcccaaga ctcatttgct agatagcagc actgatgcca gcatttcccc ctgcggcaat   29580
attgtctttg ctacttgttt accactgtcc tcaaccaacc agccaaaacc accaggaaca   29640
accttataat ccaacaagtt acattcattg atttatcaca atgagggaga ctgcatgcca   29700
gtggagctgt gacacatcct accaaaaaag aaaaaaaaga ataattatta tgggatttta   29760
agagaagggt acattttaag tgaaatttaa atgaagcagt gcttaaagtt tttttttttt   29820
tgagacggag tctcgctctg tcaccaggct ggagcacagt ggcccaatct cagctcaccg   29880
caacctctgc ctcctgggtt caagcaattc tcatgcctca gcctcccaag tagctgggac   29940
tacaggcgca tgccaccacg cccagctaat ttttgtattt ttagtagaga tggggtttca   30000
ccatgttggc caggatggtg tcgatctctt gacctcgtga tcctcccacc ttggcctccc   30060
acagtgctgg gattacaggt gtgagccact gcgcctggcc taaatttttt tttgttttat   30120
tatgctaaaa tgtgtgtaac ataaaattga ccatttttaat cattttcaag tgtacagttc   30180
agtggcattt aagtacattc acattgttgt gtaaccatca caactattca tccccagaac   30240
attttcttct tgcaaaactg aaactctgtg ccccttaaac aataactcta tatttcccac   30300
tctcccaaag cctctggtga ccactattct attttctgtc tcaatacgaa tttgactatt   30360 ctaggtctt tatagaaatg gaatcatgca atatttgtcc tgtgtctggc ttgtttcatt   30420
tggcataatg gtgaagcagt gttttgatgg gctatatgta aaatagttca taagaaatct   30480
ggacttgaag tggacctaga ctcttgttcc ttgaaattta caagttagt tcccaaatct   30540 tgatagcgtt ttttttgtttt ttgtttgttt gtttgtttgt tggtttgttt gagacacatt   30600
ccggctgtgt tgcccaggct ggagtgcagt ggcgtgatct tggctcactg caacctctgc   30660
ctcctgggct caagcgatcc tcccacctca gcctcttggg tagctgggac tacaggtgca   30720
tgccaccacg cctggctagt tttgtttgtt tgtttgtttg ttttttggta cagatggggt   30780
ttcaccatgt tgcccaggct gttactgaac tctgggcta aagtgatcct cccatcttgg   30840
cctcccaaag tgctggaatt acaggcatga gccaccgtgt tcagcttcaa cagcctcttt   30900
cagcctcata tcttgccact cttccttcgc agcatgataa actttagcac actaaatgcc   30960
ctctattccc taaacatgca tgtgaatatt tgcacctact gttctttctg ctggagcatt   31020
atgccatcct tcaggttttg tcttagaaac cccttcctct gggaagtctt cctgaacttc   31080
ccaagactgg atgagttgcc ctttctttgt tccgctatag gatcctgacc ttacctacaa   31140
catagcacta atcaagcata attgtcacta tttgtttacg tgttcatctt cgccggatta   31200
caaaagcaag aataattcaa cctccaagca tttggcatca tacctggcac atagccatta   31260
caaatgcact tttaattaat aataacaata atcaggtcca gggcagcact ttgggaggcc   31320
aagatgggcg gatcacttga agtctcaaaa aaaaaaaaa aaaaaagaa ataagaagta   31380 ctagctgtgc acaggcacac gcctgtaacc ccagcacttt gggaggctga ggcaggagca   31440
ctgcttgagg ccaggagttt gagaccagcc tgggcaacat aggcagactc cacctctaaa   31500
aaaagtacat atataaaaat aaattttaaa aattaggtgg ctgtggtggt gcacacctat   31560
aggctcagct actcgggagg ctgaggtggg aggattgctt gattccagga ggccaagct   31620 gcagtggatg atgattagtc cattgcactc cagcctgggt gacagacctc atctcttaaa   31680
aaaaaaagta cagctagtac aagactttct tctagtgtgt actttcatat tgctaaatat   31740
```

```
catgtttaga atggtattta ttaattgttc agtttgggct tcatctatta agatttatta    31800
cttttacatt acttgcctca cacacaagca atgcccaatt ttcccaatct ttgtgtctat    31860 tttttttaaaa tcaatattca atgtctctgt tattatgact aggtaaaata ttatttgcag   31920
ctgagctcca tagtgtgttg attacatttc ctctccttt agacattgta tttatctcag    31980
cattagtaat aaccacttca tttcttcatt tgcttacttt ttgtatatct gttactaatt    32040
catcccatcc tgtgtattgc acctataaaa caaatctcaa tacaggtgat tagatatcag    32100
gcaatctgtt ggttcctttt gttttggag acattgctcc tggaccctcc tggcctctaa     32160
ttttactcca caccacctgc tctctggatc cactgcccag ccgcccatct gagattccct    32220
tcgtgtcatc ctgggaattc ccttgcctcc ttgctgtgtt gaatccttgt gtactggata    32280
tgtggcttaa tcttcctttc cttacttttt ttttttttt ttgagacaga gtctgactct    32340
gtcacccatg cttggagtgc aatggcgcga tctcagctcc ctgcagcctc cgtcttctgg    32400
gctgaagcca ttctcccctc ttcagcctcc tgagtagctg ggactacagg catgcaccac    32460
caggcctagc tactttaaaa aaatttcttt ggtagcgatg gggtcttact atattgccca    32520
ggctggtctt gaactcttgg gctcaagtga tttacccacc tcagcttccc aaagtgttgg    32580
gattacaggc ttgagccacc ttgcctggct tccttgcttt acttaatcct cttttactag    32640
ggcatatttc ccagcagctt cttgagaaag ggtacacgga gaatatgaaa gatagagttg    32700
tttgttgtct ctaattcttc tgagctcttt tctttctttc agtttgatct gttctctgta    32760
tgttcatatt ggagcatttc ctcacatatc agttgaatca catatcctca catatcagtt    32820
gaatttgtat ctaaaagagt ttcactaaaa agttctgtat gtttgagtga gcttgttgaa    32880
tgggcctcaa aggagctgaa taggtggaga actggacgat tgatagaggg attcccaagt    32940
gtcagcttgt atagatcaat ggaccttttc tctcagctag ttttccccag agagataatc    33000
caaacacctg cctgtaggtt atgagactgg aggcaacatt cttggcactg aatggggttc    33060
atatttcagt gtgtagactc ttctttgtcc tcatattttc actccagctc cccatttctg    33120
ctcccagcca tacccagctc cttagcatct ttgtttcaag ccctccaggg agtaaacttc    33180
cagccaactg ccaggaaagg agaagagtaa ctcctcatag gggacagggc agggaatcca    33240
gtacttattc cagcacagac ttatgagcac cctctcgttt cagtcttgcc tgcatccctg    33300
tcttcagagg taccttcagt tcccattcct ttctgaaatt cttatttctg gttgggctgt    33360
ccccttgcaa gcattgggca gaacacagaa agctgacaac tcaatcagtt attattcgtc    33420
catatagttt tctctgtcca aaatgttgat attgctcatc tgttgtttta tcatttgggt    33480
gtttttattt tttgtcctta tttacatgtt tttaattct tttactgtga ttttagtgtg    33540
atttgtggag ggattggaga aaagcttgta cattcaatct gccatttta attggaactc    33600 tgtacttatt ttatttttatt tacttttttg gagatagggt ctcgctctgt tgcccatgct    33660
ggagtgcagt ggtgcaaaca tggctcgctg cagcctcaat attccaggct taagtgatcc    33720
tccaccacag cctcctgagt agctgggagt acaggtgcat ggcaccacac ctggctactt    33780
ttaacatttt ttgtagagat ggggtctcgc tatgttgctc agagtggtct ctacacatt    33840 ttaaaaggct ttgacacatg ttaccaaatt acctaccaga aagatcttgc ctctacattc    33900
ccaccaaaag tctttacccc acataattcc tgaccaatac tggataatac atattcaaat    33960
atttataaga atacttgaaa gcgtttttttt aaaaaattca ggatgctatc cattatgtac    34020
ccaactataa attatattca gttgtatttc tagattaact tctaacatct tttcaataga    34080
aaacctcaac ctctagaatg caacctctgg gagcaaagag caaagatctg tctttcctgc    34140
```

```
ccacaactat aaattgccat cttctgggac agtgttggcc actcagcagg cactcagtaa    34200
ataattgttg agtaaatgca ttaagaatga aggggaggtg ccatggccag ctgtgtccaa    34260
ggggaatgcc tgtgccccct cctgttgcct gttggggtcc tcttcttagg tgacttgttt    34320
ttcacctggg attggctttt ctactgtgtt aaatcttaga agtctttttc tctccgtgtg    34380
aaacttcaga atgacagcct gaggctgaaa tggacctaca gacatttgtt tgaccctcac    34440
aacattgaaa acaagggag gagaggccag gcccagtggc tcacacctgg aatcccagaa    34500
cttggggaag ccaagaaggg aggattgttt gagcctagga gtttgagacc agcctgggca    34560
atacagtaag accctgtcta tacaaaaaat taaaaatata aaaattttaa ataaataagc    34620
aagggtgggg gaaggagatt tcacataaaa cctgcagctt gggttgggcg cggtggctca    34680
cacctgtaat cccagcactt tgggaggccg aggccggtgg atcacgaggt caagtgttcg    34740
agaccagcct agccaacata gtgaaacccc gtgtctacta aaaataaaa aatacacaaa    34800 aaattagccg ggcatgatgg caggtgcctg taatcccagc ttctcgggag gctgaggcag    34860
gagaattgct tgaacccagg aggtggaggt tgcagcgagc tgagatcatg ccactatact    34920
ccagcctggg cgacagagcg agaccctgtc tcaaaaaaaa aaaatctgca gctctctggc    34980
ttcttttgga agatgtagca gggctggact atctatctgg gttggataac atcactgcga    35040
gctgggtaat gatgcccctt tagttgggca tatgatctcg atttactgct gtgtcttcct    35100
gtcccacatc atccatttct gtgaactgtt ttgaccctgg agacactgga gcttttggct    35160
tcagctttag aaagtccaaa ctatgcagaa gtggtggtgg tggtggttca tggggttttg    35220
gggatcattc tgactttttg gtaagaagag aacaacttgt aagtttata ctacctagta    35280 agtcccatct cgttccctag gtgagtcttc ctcacactca cctttcagag tttatggtcg    35340
atctagttta aacaactgtt gggagacact tatacaagaa tattttcaca tttctgcaca    35400
gttcaggctt tctaagcaaa aaacactagg aaactaagtt aaaagatgac tgaatgtcag    35460
aaacgcctcc gaagttagtg tattgctcca gagaaattta gaggctgatt ttcccaaaag    35520
ctgtttgctt atattctagg gtaataaaac atagagtcat cttttcctg gaggcatttg    35580 cttacaattc atagtaaagt gctctctcct tctctggagg gaaagatggg ctaaagtgcc    35640
accacccaat ataccctg agtctcatca ttccagagct ccctcctgtg atgcagctct    35700
gccagctgtg caggtcaaca cccggctctc atcacgttgc cctgtgagga actgggttgt    35760
ggggaactgg cattacaatg ttctgtgagt gataaatggt ctgctctctg gtccagagat    35820
ctcaggtttt ctgtcagaat agagatataa atataaaaca gcaacccctg ctagtggcag    35880
cagcctgaag ttttgtgtga tgattccacc tctgtgtgaa ttccacaggg gaaacctcca    35940
atttctacaa cttttcctca gaccccttag catctgtatt actccatccc cagactctgg    36000
cttgagactg ttttctttct actactaaga atatccagtt attgtttttc ttgttgtaga    36060
gttttcgacc tctcatatga agtacagtgg ccgaagcatc aaggtaagat tagtgctagc    36120 attttttgact tgagaattaa aaccaaacaa ctctattcac taatttagaa ccaaatcctc    36180
agcaattaca cttgacccctt caacaatgca ggggtaggg tcactgatgt ccccaacaca    36240
gtcaaaaatc cacacataag ctttgattcc cccaaaactt agctactaat agcctaccgg    36300 ttgtttgtt tgttttgtt tgttttgtt tgtttttg agacagagtc tcactctgtc    36360
acccaggcta gagtgcagtg gtgcaatctc ggctcactgc aacgctccgc ctcccgggtt    36420
cacgccattc tcctgcctca gcctcccgag tagctgggac tacacgcacc cgccaccacg    36480
```

```
cccggctaat ttttttgtatt tttagtagag acggggtttc tccatgttag ccaggatggt   36540
ctcgatctcc tgacctcgtg atccgcccgc ctcggcctcc caaagtgctg ggtgttctgt   36600
tttgttttgt ttagagacag ggtctcgcta tgttggccac gttggtcttg aactcctggc   36660
ctcaagcaat actcccccctt agcctcccaa agtgctaggg ttacagatgt tagccaccgc   36720
acatggctgc agtagcctac tgttgaccag agccttatag ataacataaa cagttgatta   36780
acacacacat tttgtgttat atgtattata tgctgtattc ttacaataaa gccaagaaaa   36840
taaaatgtta ttaagaaaat cataagggggc caggtgtggt ggctcacgcc ttaatcccag   36900
cactttggga ggccaaggcg ggtggttcac gaggataaga gatcgaaacc atcctggcca   36960
acatggtgaa actccgtctc tactaaaata caaaacatta gctgggcatg gtggcgggtg   37020
cctgtagtcc cagctactcg ggaggctgag gcaggagaat tgcttgaacc tggaaggtgg   37080
aggttgcagt gacccgacat catgccaccg gactccagcc tggcaacaga gcaagactcc   37140
gtctcaaaaa taaaacaaac aaacaaccaa aaaaaaaaaa caaaaaaaga aaatcataag   37200
gaagagaaaa tatatttact cttcattaag tggaagtgga tcaccataaa ggtcttcatc   37260
ctcactgtct tcatgttgaa taggctgagg acgaggagga acaggagggc ttggtcgtgc   37320
tgtcacagag gtagcagagg aggaagaaaa tccacatata ggtggacttg cgtagtttga   37380
agccctgttg ttcaagggtc aactgtattt cttggaaaaa caacaactca catatagttc   37440
ctagagtagc aaatcgttcc tgggaaaatt atgccttgcc atgtgcagtg cttttctgga   37500
gtgtttctgt tctttacata atgagctgag tagctcccctt agacattttt ttttttttga   37560
gacagagtct cactctgttg cccaggctgg agtgcagttg gcacaatctc ggctcactgc   37620
aaccaccacc tcctgggttc aagcgtttct cctgcctcag cctcctgagt agctgggatt   37680
acaggcacct gccaccacac ccagctaatt tttgtatttt tagtagagat ggggtttcac   37740
catgttggtc aggtgggtct tgaactcctg accttgagtg atccgattgc ctcggcctcc   37800
caaagtgctg ggattacagg tgtgagccac cacacctggc cagacatatt ttaatttgtc   37860
ttttttcaac ctatttagaa attaggcaat tcttttcttt cccccagtgg tggaaagatt   37920
ttcctagctg tctaatttat aagttttttgg aaagatattt gcaattctta gtttctcaac   37980
tacctgaccc ttcttttcct atgagccttt gagaaatact tatgcatagg tactgcttag   38040
cattgtaaaa ggagtttatt gacctaaaaa attgtaatgg ctgttactag gcagatggtt   38100
aagcactgga tgaatctgcc tttatgtcct aagtcatttt tgagaaatga ggaaaatcat   38160
ctagacagta aaactggggt ctacactaca tctcatctac ttttaatgcc taagtttcta   38220
gagtcaggtt ccatttcctt ccttcttaca cacaggtggc aatagaatga aaattaaaca   38280
tacatttctc aattactacc catgacccat gcctataaat attgtgatat aaataggtat   38340
tgaatctgta tacacaggaa aagaccacaa tgaaagaag cataaagtta aggagtttat   38400
agcttactgc ccgcaaagtt taatattata cattgggtta cactgacctc tacaggatga   38460
taataaaaac tagcttagtt tgaaactaga ggagggcaaa ggagaaagga aaaactagct   38520
tagtttgaaa ctagagggca aaggagaaag gaaagccatc catttgcctg tcatccacaa   38580
aaatgaaatt ttgtacattt cattcacaaa ctaattcagc aaaacgatgg tgaggtagtt   38640
gtgtttcgga tatgaattct gagttagtca ataactggt aatttttgag gtattttaac   38700
agcaatttta aactgttttc agtgggattt caaaaatctt aaatcaattc tatggaaagt   38760
aaaaagaaaa aagaagagaa ataaaatgct tcttatctta aattttttacc atttacatta   38820
tagggccttc atttaaaaat atataaccat gaatatttac atctataata atcctggttt   38880
```

-continued

```
taaaacgtgt tgttttaaat tggttctaaa aaaatatatg gaatgaggt tttaatttta      38940
aaaattgtga tctttccagg catagtggct catgcctgta attccagcat tttgggaggc      39000
agaagtggga ggattgcttg aggccaggag tttgagacca gcctgggcaa catagagaga      39060
ccttgtctct actaaaattt aaacattagc cgagcatagt ggcacatgcc tgcagtccca      39120
gctacttggg aggctgaggt gggaggatcg cttgagccca ggaagtcaag gctgcaatga      39180
gctgtgatta tgccactgca ccccagcctg ggtgacagag cgagatcttg tctcaagaag      39240
aaaaaaaaga attgtgattt ccaggatagc tttgaactt aaaagccttc cttaagagga      39300
tattataatc tctttagact actttaaacg agttagcgtg atatttatat atgtttctgc      39360
attcacagct ttttctgtct tccttttagt tccttctgcc accactgtca ctcttgccca      39420
cgcgatctgg tgtccttact atcccccaaa atcacaagtt tccaaaagaa aagaaagaa      39480
acattccaag tctcacatct tttgtgccta agctctcagt gtctgttcgt caatctgatg      39540
agctcagccc atcaaacgag cctccgggag ccctagttaa gtcgttgatg gatccgactc      39600
tcaggtcttc tgatggcttc atttggtcaa gaaacatgtg ctcttttcct aagactaacc      39660
atcacaggca atgcctggag aaggaggaaa actggaaatc caaggaaata gaagaatgta      39720
acaaaattga aatcactcac tttgaaaaag gcagtctttt ggtgtctttt gagaatttga      39780
aggaaggcaa tattcctgca gttagggaag aggatattga ctgccatggt agtaaaacgc      39840
gaaaacctga agaagagaac tctcaatatc tttcatcaag aaagaatgag agttcagtag      39900
ccaaaaacta tgaacaagat ccagaaatag tatgtaccat tccaagcaag ttccaagaaa      39960
cccagcattc agaaataact ccaagccagg atgaagagat gagaaataat aaagctgctt      40020
caaaaagagt ttcattacat aaaatgaag caatggaacc aaacaatatt ttagaagagt      40080
gtactgtact aaaagctta tccagtgtag tctttgatga ccccattgat aaactcccag      40140
aaggttgtag cagcatggag acaaacataa aaatatcaat agcagaaaga gccaaaccag      40200
aaatgagtag gatggtgcct cttatccaca tcaccttccc tgtggatgga agccccaagg      40260
aaccagtgat agccaaacca agcctccaaa caagaaaggg aaccattcat aacaaccata      40320
gtgtcaacat acctgtacac caagaaaatg acaagcataa gatgaattcc cataggagta      40380
agttggattc aaagaccaag acaagtaaga agacacctca gaattttgtg atttctactg      40440
aaggtcccat taagcctacc atgcataaaa ccagcataaa aacacaaatt ttcccggctt      40500
tgggacttgt ggaccccagg ccttggcaat tgcccaggtt tcaaaagaaa atgccacaga      40560
tagcaaagaa gcaatcaact caccggactc agaaacctaa aaagcaatca tttccttgca      40620
tctgtaaaaa tccaggaaca cagaagtcat gtgttcctct ctctgttcaa ccgacagagc      40680
caagactaaa ttacctagat cttaagtata gtgatatgtt caaagaaatc aattcaactg      40740
ctaatggacc tggaatctat gaatgttttg ggaccctgt ttattgtcat gtgcgagaga      40800
ctgaaaggga tgaaaacacg tattaccgtg agatatgttc ggctccatca ggcagacgta      40860
tcaccaataa atgtcgatct tcacacagtg agaggaagag caatatcaga acaagacttt      40920
ctcagaaaaa aacacatatg aaatgcccaa agacttcatt tggcattaaa caagagcaca      40980
aagtcttaat ttctaaagaa aagagttcca aggctgtaca tagcaaccta catgacattg      41040
aaaatggtga tggtatttca gaaccagact ggcagataaa gtcttcagga aatgagtttc      41100
tatcttccaa agatgaaatt catcccatga acttggctca gacacctgag cagtccatga      41160
aacagaatga attccctcct gtctcagatt tatccattgt tgaagaagtt ctatggggaag      41220
```

```
agtctactgg tgatagagac atttctaaca atcaaatact caccacaagc ctcagagatc    41280
tgcaagaact tgaagagcta catcaccaga tcccatttat cccttcagaa gacagctggg    41340
cagtgcccag tgagaagaat tctaacaagt atgtacagca agaaaagcag aatacagcat    41400
ctcttagtaa agtaaatgcc agccgaattt taactaatga tctagagttt gatagtgttt    41460
cagatcactc taaaacactt acaaatttct ctttccaagc aaaacaagaa agtgcatctt    41520
cccagacata tcaatattgg gtacattatt tggatcatga tagtttagca aataagtcaa    41580
tcacatatca aatgtttgga aaaaccttaa gtggcacaaa ttcaatttcc caagaaatta    41640
tggactctgt aaataatgaa gaattgacag atgaactatt aggttgtcta gctgcagaat    41700
tattagctct tgatgagaaa gataacaact cttgccaaaa aatggcaaat gaaacagatc    41760
ctgaaaacct aaatcttgtc ctcagatgga gaggaagtac cccaaaagaa atgggcagag    41820
agacaacaaa agtcaaaata caggttggta taattagaat ccaagattca ttggggtggg    41880
aaggacctca gagacaatct ggttcaaacc ccttatttc aaatgaggaa ttataaaccc    41940
taaacaatta aatagttttt tcaaggtctc actgtttgat cacaaggttg gaaatcaggt    42000
cctctgaccc ccaggctaag atgttttcat tatattgact cccttctgga atttagctag    42060
cttgacattg caatgaaatc agtttggtta aattaattta gcaaaaccat tcaaataggt    42120
cagtatttta ttcaatgatg acattttcaa tcaacagcat atcatttcca actatcagca    42180
gatacataat tataggcaag acattgctct aggtatgtga gatagaaaga aatgaacatg    42240
gctccagaag tggctcacca ttttgttcat aggaagacat gaaatgtaca tttctcagag    42300
cccctacacc tgagcatttg ctctcagatg attcactact ttaatgcaaa attattattg    42360
atgcctactg tgcttctggc agtgggccaa gaactaggag catagtgctg tacaagactc    42420
ggccattgct ctcatggaag tgtaagcaaa atcctgaaa taagattttt aaaaattttg    42480
tttggcatga gagttggcat ggagtgggga agaagatcaa cacatagtcg ggttttcttt    42540
gttatcgttt tcactaaagt acacaagcct cccaaactga aattttaaag acagaaacag    42600
taggtaaact gaaatattat ttattgaaca ctaactcagg tcatactgca ctatatccac    42660
actatatcag gatcaggaat aatttttttt tgagatggag tcttgctcta ttgcccaggc    42720
tggagcgcag tgctgcgatc tcggcttgct gcaaactcca cctcctgggt taaagcgatt    42780
ctcctgcctc agcctcccaa gtagctggga ttacaggcac tcaccaccac gcctggataa    42840
tttttgtatt tttagtagag acgggatttc accatcttgg ccaggctggt cttgaactc    42900 ctgacctcgc gatccacctt cctcggcctc ccaaagtgct gggattacag gcgtgagcca    42960
cggcgcccag ccaggaataa ttattttaaa taattattgg tcagaagaac atacaaggta    43020
aataattatc ccatagcttc ctggactgtt tgctagagat actagtctga cttactgcaa    43080
gtctggcttg tggatggtaa actggcttcc tgttttggtt actgtagata atgggttgat    43140
ttcctgggtt ggttgctgca cattgtaggt cagagttcta tttttatata tgatctggcc    43200
attgttggtt tgtatattat ctctcagtac atatgtgtat gtatatatat gatatatatg    43260
tgtgcatgat atatatttat gtttatgtgt gtgtacattt gtgtgaacac atatgtgaat    43320
atgtgtgtat gagtttgtgt gtctctatgt gtgtgtccag ctctgtgtat gtttctcttt    43380
ctgaacttgt ctgtgtttag gagcaagctg accacgataa tgggaatttt gaggagagag    43440
ttgaggttag ggggctgagg agatggcaca cactaacata ttctgtcatg atagggacct    43500
tgtgaaagat aattctcaaa agacagtggt tagtagctgc aggcctatgt ggggcctgag    43560
atgaacagga ctaagatctc ctcctataaa atatgcagag caagatgtgg ttttaaaatg    43620
```

```
tgtataatta acaaggctga agttcacaac taagatacac tatgtggtca tttgggggaa   43680
tgatgtgtct ctagaagtta cctgtaagag tggccacaga caggaacatt tgaaaagaag   43740
actttactct caccccttc tctccatccc agtgacttgg tttaatggtc atctttcctt    43800
ttgtctcatt cttccagagg catagtagtg ggctcaggat atatgacagg gaggagaaat   43860
ttctcatctc aaatgaaaag aagatatttt ctgaaaatag tttaaagtct gaagaaccta   43920
tcctatggac caagggtgag attcttggaa agggagccta cggcacagta agttaaactg   43980
gaaacttgaa atcaaacctt ccccccaccc ccccacagtc cctccctcca ccctcccac    44040
tcccccagtc atcctccctg cttcctctgg caagcactct tttacttaga actctttcag   44100
ttggaagtaa cagaaaatcc aaccactgag ggaaaggaca gttactgctt tatccgactg   44160
aaaggtctgg aataggtctg gctctgggtc caggaggctt cagggatcag acaatgtcat   44220
caggatctgg tctctctctc tctttgcctg gcttttctc aggcacatat agtgactcaa    44280
tggccactgc atttctaacc tctcatcctc ccaggttcaa gtccaatggg aaagaaatat   44340
cttccttcaa cagctgaata tgttactgga gtttggaga atcattacta gatggcaaaa    44400
acaaaagatg ttccttccat tttgtgaact gcataagaga tcttgggggg tgggcgatga   44460
agagaggtgg gtacaaacat acagtcagat agaagaaata agttctagtg tttgataaca   44520
cagtagggtg actatagtta acaacaatat attgtgtatt tccaattagc tagaagattg   44580
aaatgcccc aacacaaaga aaatgacaaa tgtttgaggt gatggatgtc ctaaacacac     44640
tgtcttgatc attacacatt ctatgcatgt attaatatat cagatgtgcc tcttaaatat   44700
gtacaaacat tatatatcta aaccctagca ctttagatag ttatttacat agacgagtaa   44760
agaaaaggct ggcccccaaa taagacttgt gctgtctcca gatggggaca tttcagaaat   44820
cagtgagaag acaggaagac acaaaaccac tgagattaca tcacaatggt gatttccagg   44880
gcctgtctcc ttctcactcc agagagcttg ggagctgaac cagctctatt ttacatatta   44940
tcaggagctt ttccaaacca ccatctcatg tagtcatcat agaaatctgg gaggcaggcc   45000
aggtgtggtg gctttcacct gtaatcccag aactttggga ggccgaggcg ggtggatcac   45060
ttgaggtcag gagttcgaga ctagactggc catatggtaa accccgtcct ctactaaaaa   45120
tacaaaaatt agccaggtgt ggtggcacag acctgtaatc ccagctactc aggaggctga   45180
ggcatgagaa ttgcttgaac cccggggcag aggttgcagt gagcccagat cacaccactg   45240
cactccagcc tgggcgacag agcgagaccc tgtctccaaa aaaaaaaaa aaagaaaaaa    45300
atctgtgagg cagcctgggc aacatagaga gacctcgtct ccacaaaat actttaaaaa    45360
ttagcctagt gtggtggtac atgcctgtag tcccagctac tcaggacact gaggcaggag   45420
gatcgcttga gcccaggaat ttgaggctgc agtgagatat gatcagggcc actgcactcc   45480
agcctgggtg acagagagag actctgtctc caaaaaaaaa aaaaaaaaa aagaaagaaa    45540
aaggtagcac ggtggctcta caaaagtac acacacacaa ttagccaggt gtggtggcac    45600
acacctgtga tcctagctac gagctgctca ggaggctgag gtaggaggat tgcttgaacc   45660
caggaggttg agcctgcaat gagctgtgat tgtgccaatg cactccagcc tgggcaacag   45720
agtgagaccc tgtctaaaaa caaccaaaaa aaaaaaaaa aaaagaaaaa gaaatctctg     45780
aggcaagtat tgttacctca gttttacaga tgagaaaaac tgaagtcaaa agattacaca   45840
tttatcccaa gttatatagc tggggaaaga tgaagccagg attctagcca attcaagcca   45900
cttgactta agccaatatg acatccatcc accatgtttc tcatacccat cttggctcca    45960
```

```
ctgaaacact gaatttgctt aaacactttg catttaggaa gggaggtatc aacttagaga      46020
aagacaaggg tttagaaaga aagggaaag tcaagtgtca cctgaggcat tttgtgaata       46080
agttatgtca ttaatttaat aacaaggtat tattgatttg cttctaggta tactgtggtc     46140
tcactagtca aggacagcta atagctgtaa aacaggtggc tttggatacc tctaataaat     46200
tagctgctga aaaggaatac cggaaactac aggaagaagt agatttgctc aaagcactga     46260
aacatgtcaa cattgtggcc tatttgggga catgcttgca agagaacact gtgagcattt     46320
tcatggagtt tgttcctggt ggctcaatct ctagtattat aaaccgtttt gggccattgc     46380
ctgagatggt gttctgtaaa tatacgaaac aaatacttca aggtgttgct tatctccatg     46440
agaactgtgt ggtacatcgc gatatcaaag gaataatgt tatgctcatg ccaactggaa      46500
taataaagct gattgacttt ggctgtgcca ggcgtttggc ctgggcaggt ttaaatggca     46560
cccacagtga catgcttaag tccatgcatg ggactccata ttggatggcc ccagaagtca    46620
tcaatgagtc tggctatgga cggaaatcag atatctggag cattggttgt actgtgtttg    46680
agatggctac agggaagcct ccactggctt ccatggacag gatggccgcc atgttttaca    46740
tcggagcaca ccgagggctg atgcctcctt taccagacca cttctcagaa aatgcagcag    46800
actttgtgcg catgtgcctg accaggtaag aaactgaaag caagaggagg aagataaatg    46860
cccggagatt ccaagtggca gacatttccc tttcaattta tggcccatta aaagctctgt    46920
tttggttatg aagtcaagta gacagtgatt ttgtgccgaa agtaatcata atcagtcata    46980
ttgggtaatt gtgttcattg ttgtatcagg gtataggagg caatgcttca agtagaaagt    47040
gcctcaatta aatgtcttat caagttctgt caatacttgc ccaaatcaat gggtttgcaa    47100
aatttgttaa agatctactt atttaccaat gagacatctt cctaggaact ggctagggtg    47160
aaatgacatc atcttgcatt taaagtgagg ggaaacattt tgagccaaag aaacaaattg    47220
gagatttcaa gcgtcaagtg ggggagtatt tggtgaatcg gaaaagcctt agaaaattgc    47280 ctgtttttccc cttccttatc ttctctccta tctatggaat taaattgtgg gtaaaatgtt   47340
agaactgtaa ctgtaatgta atggaaatta actagtgctg tgattttcaa atttttagcc    47400
aggtactctg ctcatagaaa tcttaaatca aagaataaaa taaaagcaga cagatggctc    47460
tagttaaagt gtgtatccat ggggcgggga agagttaagg agtagggctg tgggtgctgg    47520
agcccactct aggatactgc acagcagccc caaacccacc tacctagcaa ggctcaactt    47580
taattggagg acaagaaagg cctgagactc aaagtcaatt tcctgtcttt caagtaagtt    47640
tgccttctta tccctagatg aaaaactcca gtgtcccatc ttttagcaag cacatatggc    47700
aacccccaac tcccagggg ttcatttttgc ctttctgaat aaatcttaga atctacaggt     47760
ctccctctct gccaatgaat gtgcctctct ttcagtctct gtctctctct cccagcacat    47820
gtgtatcagc ctgtcctggc tgatttcagg atgattacat gggccagggc aggaatgcca    47880
ctccaggggt acagttttttg gcattgctag atgcagagaa cccttaggtt ccagcgtgg    47940 attttgtgga cagagcccca gtcattgagc tgcccaccct ctccaaaaaa aaaaaaaaa    48000 aaaccgcat aaatgtgttg gaaatcgta tagacaagta ctagtttgat attggtgtta    48060
actgttaaaa ctattgtagt tgctttgttc cgaatttaac aattaccata attattgact  48120
cacagctaga aaccacttgt tattctcatt ttctttcaag ttgtgattac acacacacac   48180
acacacacac acacacacac acgaagcact ttaaagagaa agggtggaat cttcttttat    48240
ggctctcctt ttgaaccgtt gcttcataaa ctaagcaata tacaattcac accactaata    48300
aaaattaaca gggttattgt gaaggttaag tgaaatggtg catgtaaatt gcttagcaga    48360
```

```
gtgtggggca caaaattagg agtttacagt taataatcat taggaagaat attaacatac   48420
cttacctaat tagagtcata tacaagtata taattacctc ctaaaattct atggcaaaga   48480
ccctgaggac cctagcatct cacctgatat caataacaat actccttgga gatagggata   48540
ttcagaaaat aaagggcgag gcactcttaa agattcagaa atagagataa tcaggcatag   48600
actagggaaa gtctaaagaa aacagaaatg aacttgggga agctgagaga aataagcatg   48660 gaggggtac tcctattgac agatcaagtt cctgggaagt caggccaagg agtttagctt    48720
tgttgcaata ggcagtgagg agcagggggc tgcaaaagat tggggtaga aaaggccata    48780 aagaaaaggg tctttgggaa ggcaggtcag atggcaatgt attgaagggc ctgggatgga   48840
tgtcgcttga gactagaaag ctctgcagaa atccagagct tggatgctga tggtggtaga   48900
agcagtggga ttgtaaagga ttccagaaaa tttcagagaa aaggtgaatc aagacttggt   48960
aatggagcag aatgatagga tttcacattt ttgactctgg ataatgggag aaatcacagt   49020
tgtgagagaa gaacagggag gcagctaaac ccttcccacc tcctgtaagg agacatttga   49080
agctatggaa ttgcagctca ggaaagcaat taagattgga aggacacatt taaaaataat   49140
tataacagcc aggtgcagtg gctcatgcct gtaatcccag cacttaggaa ggccgaggtg   49200
gggggatcac ttaagcccag gagttcaaga tggagaccaa cctgggccac atgaagaaac   49260
cccatcttta caaaaaaata caaaaattag ccaggcatgg tggtgtgtgc ccgtagtccc   49320
agctactcag gaggctgagg tgagaggatg agaggatcgc ttgacccegg aagttgatgc   49380 tgcagtgggc tgagatggca ccactgcact ccagcctaag ggacagagtg agactctgtc   49440
tcaaaaaaaa aaaaaaatca ttataaggtt gattgctaca gtcataacaa aattataggg   49500
ctgaggaaaa tattttgaaa atgctcacaa tggaagctaa cagaaatgca tggcatcaag   49560
tctagcacat aactggagaa gggaagggag gaagggaagg gagttgcccc aaggtgtaag   49620
aagaaacaag aggacagagt gtccctaagt ctaagcagag gtagtttcag gtaggaggga   49680
gtagtgaatg tttcaagcgc tacagaaatg acaaacagct cattaaatct ggttaatttc   49740
aagagggcaa tttctataga ggaatgggcc aaatggttaa gaatacaggg gggaagtcac   49800
cgagcttagc cttgttagag acatttggca gagacattta aaatgggatg gccaggcgc    49860 agtggtccac gcttgtaatc ccagcacttt gggaggctga ggcagaataa ctgattgagc   49920
gcaggagttt gagatcagcc tggcaacat agggagaccc tgtttctaca aaaaatttaa    49980
aaattagccg ggcgcggtgt cacgccagta atcccagcac tttgggaggc cgaggcgggc   50040
ggatcacgag gtcaggagat caagaccatc ctannnnnnn nnnnnnnnn nnnnnnnnn    50100 nnnnnnnnnn nnnnnnnnnn nnnnnnnnnn nnnnnnnnnn nnnnnnnnnn nnnnnnnnnn   50160
nnnnnnnnnn nnnnnnnnnn nnnnnnnnnn nnnnnnnnnn nnnnnnnnnn nnnnnnnnnn   50220
nnnnnnnnnn nnnnnnnnnn nnnnnnnnnn nnnnnnnnnn nnnnnnnct gggtgacaga    50280 gcgagacttc atctcaaaaa aaaaaaaaaa aaaaaaaat taaaaatta gcaagtcatg     50340 gttgtgtaca cctgtagtcc cagtgactca gaaggctgag gtgggaggat cacttgagcc   50400
tggaaggttg agaccacagt gaaccgtgat catgccactg cactccagct ttggcaacag   50460
aatgagaccc tgtctcaaaa aaaaaaaaaa gtgggtgggg gagcggtggt agctagaaat   50520
ggtatccagt tcaaggaaag gatttttaaag gagagagatt tctgcatatt ttaaaggccg   50580
gagaaagggc ctccagatag tgaaagaatt ttttttttt tttttttcc gagacggagt     50640 cttgctttgt tacccaggct ggaatgcggt ggtgtgacct tggctcactg caacctccgt   50700
```

```
ccatgggttc aagcaattct cctgtctcag cctcccaagt agatgggact acaggcgcct   50760
gccactgggg ccagctgatg ttttgtttt tttagtagag acggggtttc accatgttgg   50820
ccaggctggt ctcgaactcc tgacctcgtg atccacccac cttagcctcc caaagtgctg   50880
agattacagg tgtgagccac tgtgccttgc tgtattttt tttttttac ttttgaaatg    50940
acacaaaata taatacttt atacaaaata cttttaagag tatttatttc cattttcacc   51000
tggaaaatga tctggtggcc attgtgcttt caaaattatt aaaagaggag gggcttcaag   51060
atggctgact agagacatct ggcacttact tcctccacaa agaactaaaa tagcaagtag   51120
ataagcacat ttcaaatata gcatcctgag agagaacact ggatttcaac agagaagtta   51180
caggaaacac ctgagacatg aagaaaagg aaggaagac agtcagtttg gttgagattg      51240
gccgagagcc cagagagcct ccctagtgtg gggaaagggt gagcagatcc tcagtggtcc   51300
acattctcac agtgaactcc tgcaatccta gccatgggag aaccctttag tccttgcaga   51360
cactgagact agaatatgga gctgcctgga aaccatgtga cagcattgct ccggagaggg   51420
agctcacacc tgagtcctaa gcagctacag catggcacca ttttgagagt ccagccccca   51480
ccagactcca tcccgccctg gggtccaaca gcccctgcaa ctccatatcc ttggaaccct   51540
acttacatct tcttgtgttt acctggaggg ctgcagcagt gtgatgccag ttgtacccag   51600
tggagtggcc agatccccag cattgtagca cacatggtgt cctgcacccc agaaacaaca   51660
gtgcagcgca ccagggaggc tgctcctggg acaaagggag ccaaagcatg tgctccccag   51720
tgcctaagaa ctgcctacct gaggtggcta ttacagatag caaccccacc ctttctagca   51780
gcagggctgc cacacacatg ctctgaggac agactctgct gctgtccact gcagcttctg   51840
cttaggctga agtgtgtgcc actggcagtg accccacccg cttcagcaac agggttgcag   51900
cacatttgca tgtgccctga ggactggctt tcttggctgc agctgctgcc accaccagaa   51960
gccaaaccat gagctccctg gaacctgaga gccacctgcc tgaagctgct gccactgacg   52020
gcaactctgc ttccaccagt agcagggcta tagcacactt gcacatgccc taatgacagg   52080
ctccccttgc ccaccaccac cggagctgca gccacccaat catcatgcca gggccctggg   52140
gatcaccccca ccctgcccac tactgctgac ccctgcgtgt accactggag ggcctgagga   52200
aaggtcaacc aagcctggcc cagcagccct gccggtgtct gagcacattg cctggggcct   52260
ggggattctc tgccctatca ctgctggtat ctgtacattc ctcatgagga cctgaggacc   52320
ggcccatcca gcccattgca gccactatta acaccagtgc ctgctgctat ggagcccaag   52380
cattatccca gtaccactat tgccattgcc catgccatgc atgctgccca ggagtctaag   52440
gacctatcca cccacccagc acaccactgc cactaccagg acctgagcaa gccttggagg   52500
cccaagaatt ggctcatttg aacccactaa cactagtgcc catgtatgtc acccaggggc   52560
ccaaggatgg gcatgcttga cacaccactg ctaccactca gnnnnnnnnn nnnnnnnnnn   52620
nnnnnnnnnn nnnnnnnnnn nnnnnnnnnn nnnnnnnnnn nnnnnnnnnn nnnnnnnnnn   52680
nnnnnnnnnn nnnnnnnnnn nnnnnnnnnn nnnnnnnnnn nnnnnnnnnn nnnnnnnnnn   52740
nnnnnnnnnn nnnnnnnnnn nnnnnnnnnn nnnnnnnnnn nnnnnnnnnn nnnnnnnnnn   52800
nnnnnnnnnn nnnnnnnnnn nnnnnnnnnn nnnnnnnnnn nnnnnnnnnn nnnnnnnnnn   52860
nnnnnnnnnn nnnnnnnnnn nnnnnnnnnn nnnnnnnnnn nnnnnnnnnn nnnnnnnnnn   52920
nnnnnnnnnn nnnnnnnnnn nnnnnnnnnn nnnnnnnnnn nnnnnnnnnn nnnnnnnnnn   52980
nnnnnnnnnn nnnnnnnnnn nnnnnnnnnn nnnnnnnnnn nnnnnnnnnn nnnnnnnnnn   53040
nnnnnnnacc cattcagaca aaaataaaga aaaaaaagag tgaacaaagc ctacatgaca   53100
```

```
tgtaggaaac tataaattgg ccagatatac aattttgatt gttccagaag gtgaagagaa   53160
gaccaaaggt atagaaaatc tatttaaaga cagaatagtt gaaactttcc caggtctagc   53220
aagagattta acatccaga tacaggaagc taagagatcc acaaatagat acaacctaga    53280
aaggtcttct ccagggtaca ttgtagtcaa actgtcaaaa gtcaaagaca agagaaaat    53340 tctaagaaca gcaaaagaaa aacatctagt aatgtataaa agaacccca tcagactaac    53400 agtggattta tcagcagaaa tcttacaggc caggagagaa tgagataata tattaaaagt   53460
tttaggccag gcatagtggc tcgcacctgt aatcccagca cttggaagg ctgaagtggg    53520 tggatcacct aaagtcggga gtttgagacc agcctgacca catggagaa atccatctc    53580 tactaaaaat acaaaattgc ccaggtgtgg tggtacatgc ctgtaatccc agctactctg   53640
gaggctgaga caggagaatt gcttgaacct gggaggtgga gggtgcagtg agccgagatt   53700
gtgcctttgc actctagcct gggcaacaac agcaaaactc catctcaaaa aaacaaacaa   53760
acaaaaaaaa aagttttgaa aggcataaaa acaaaacaaa actgtcagcc aagaatgcta   53820
tactcagcaa agttatcctt caaaaatgga gaaagtcttt cacagacatg caaaaactga   53880
gagacttcat caccattagt ggccctacaa gaaatgctta agaaagtcct acacctggaa   53940
gtgaaaggtc atatctatca tcatgaaaac atatgaaagt gtaaaactca caggtagagg   54000
aaaccacaca aaagaggtag agaaaggact caaacgttaa cactacagaa aaccaccaaa   54060
ccacaatgat aaataacaag agagaaagaa agaaagaaac aaacaaacaa acaaacaaac   54120
caaccagaaa acaatcaaca aaatgacagg aataagaaca taaatggatt aaaatttcca   54180
attaaaatgg ctgaatagat ttttaaaaag tgacccaaaa atatactgct ttcaagaaac   54240
tcactttacc tgtaaagaca catatagact gaaagtgaaa ggatggaaaa agatagttca   54300
tgcaaataga aaccaataga gagcatgagt agctatattc atatcagata aaacacactt   54360
tatgtcaaaa acagtaaaaa gagacaaagt cactatataa tgataaagag aaaaattcag   54420
ccagaggatg taacagttct gatgcaccct gcaccagagc acccaggtat atgaagcaaa   54480
tattattaga tctgaagaga gagataaact ctaatacaat catagatggg gactttaaca   54540
ccccactctc aacattaagc agatcatcta acaaaacat caatagagaa acctggattt     54600
aaattgcact ttaaaccaaa cagacacaac agatacctac agaatatttt ctccaacaat   54660
ggcagaataa atgttcccat taaaacatgg aacattttcc aggataggcc atacattagg   54720
ctgcaaaaca agtttcaaca aattttaaa aatcaaaatc ataccaagta ttctttcagc    54780
cacaatggaa taaaactaga aatcaataac aagaggaact ttggaaactg tataaataca   54840
tggaaactaa acaacatgtt cctgaatggc tactggggca agaaagaaat taagaagaaa   54900
attaaaaaat ttctcaaaac aaatgaaaat caaacacaa catacccaaa tctatgtgac    54960
atagtaaaag cagtgctaag agggaggttt atagcaataa aagcctacat caaaatgta    55020 tgaagattgg ctgggcatgg tggcttacac ctgtaatccc aacactgtgg gaggccaagg   55080
tgggaggatc acttgaagcc aagagttcaa gaccagcctg ggtagcaatg tgagaccttg   55140
tctcaaaaag aaaaaaaaaa aattagctag ctaggtcact tggtaggcta gggtgggagg   55200
attgcttgaa cccaagagtt cgagactgca gtaagccatg attgcaccat tgcattccag   55260
atggggtgac cttttaaaaa agtataaaaa tttaaataaa taatcaagga aacagaagaa   55320
aaagggaaca aaccaaaccc caaattagta gaaaaaaaga aataaagatc agattatgtt   55380
aagtgaaata aaccaggatc agaaagacaa acattgcatg tcctcactta tttgtgggat   55440
```

```
ctaaaaataa aaacaattaa attcattaac atagagagta gaaggatggt taccagaggc    55500
tgggaatgat agtaggagga taggagtagg gcagataggg atggttaatg gattaaaaaa    55560
aaaatagaaa gcttgaataa gacctaccat ttgatagaac atcagggaga caatagtcat    55620
taataactta attgtacatt ttaaaataat taaaagagtg taattagatt gtttgtaaca    55680
caaaggataa atgcttgaga ggatggatac cccattctcc atgatgtaat tatttgacat    55740
tgcatgcctg tatcaaaaca tctcatgtac cccataaata tatacaccat gtacctacaa    55800
aaattaaaaa taaaaaaata taaaaatcaa tagaaaagta ataaaggtca gagtagcatt    55860
aaatgaaata cagaaaaaaa tacaaaggat cagtgaaatg agaagttggt taaaaaaaaa    55920
ataaaatcaa taaactgcta gctagactaa ccagaaaaa aagagagat gactgaaata    55980 aaaatcagaa acaaaaaagg agacataaca actaatacca cagaaatgaa aaaacccacc    56040
agagaacatt atgaacaaat ataagctaac aaaatggaaa acctagagga aatggataaa    56100
ttcctggaca catacaagac tgagtcagga agaaatagag aacctgaaca gaccaataat    56160
gagcaataag attgaatcag taataaaata tctcctaaca aagaaaagcc caggactgga    56220
tggcttcact gccatattct accaaactca taaagaagaa ctaacaccag ttatcctcca    56280
actattccaa aaaattgaga aggaaggaat tctccctaac tcattcaatg aagccagcat    56340
taccctgata ccaaaaccag acaaggatgc gaaaaccaca aaaaaagaaa actataggcc    56400
agtatccttg atgaacacag atacaaaatt cctgaacaaa atactagcaa acctaaccca    56460
acagcacatc aaaagataa tacaccataa tcaagtgagt tttatactag tgatgcaagg    56520
atggtttaac atgcacaaat caataaacat gatacatcac attaacagaa tgaaggacaa    56580
aaacaatatg accatctcaa tagaaacaga aagacattt tctaaaatcc aacatccctt    56640
tgtgataaaa actatcaaca aactaggcat agaaagaaca tacctcaata taataggcca    56700
tatatgacaa acccacagct aacatcatac agaatgggga aaaggtgaaa gcctttcttc    56760
ttagaactgg aacaagagaa ggatgccaac tttcaccgct cctattcaac atagtattgg    56820
aagttctagc cagagtgatt aggcaagaga aagaataaaa ggcattcagg ctgggcgcag    56880
tggctcatgc ctgtaatccc agcactttgt ggggctaagg caggcagatc atgaggtcag    56940
aaaatcgaga ccatcctggc taacacagtg aaacccatc tctactaaaa atacaaaaaa    57000
ttagccaggt gtggtggcgg gcacctgtag tcccagctac tcaggaggct gaggcaggag    57060
aatggcatga acccgggagg tggagcttgc agtgagctga gatcgcacca ctgcactcca    57120
gcctgggcga cagagtgaga ctccatctaa aaaaaaaaaa aaaaaaaag gcattcaaac    57180 tggaaaagag aaagccaaac agtgcctctt tgcagatgac gtgatcttat atctagaaaa    57240
acctaaagac tccaccaaaa aactcttaga tcgattcagt aaagattcag taaagttgca    57300
ggatacaaaa ttaacatacg aaaatttgtt gtgtttctat ataccaacaa tgaagtagct    57360 gaaaagaaa tcaagaaggc aatcccattt aaaatggcta caaaaataaa ataaatacc    57420 tgggaacaaa tgtaaccaag gaggtgaaag acctctacaa ggaaaactac aaaacattga    57480
tgaaaaaaat tgaagacaca aacaaatgct catgggtcac aagaatcaat attgttaaag    57540
tggtcatact aaccaaagtt atttatggat tcaatgcaaa ataccaatg taattttca    57600 cagaaatata tacaaaacaa tcctaaaatt tgtgtggaac caaaaggag ctcaagagc    57660 caaagcaata ctaaacaaaa agaacaaagc tggaggcatc acactatgtc acttcaaaat    57720
atacagaaaa tatatacaaa atatattaca aggctacagt aaccaaacag catggtattg    57780
gtgtaaaaat agacacataa accaatagaa cagagtagag aacccagaaa taagtcccca    57840
```

```
tatgtaaacc aacttatttt tgacaaaggg accaagaaca tatactgggg aattgacacc     57900
ctcttcaata tatggtgcat attcatatgc agatgaacga agttagaccc ctatctcacc     57960
atatacaaaa atcaactcaa aattgattaa atacctaaac ataagactca aaactataaa     58020
attactagaa gaaaacatag ggaaacactc caggttattg gtctgtgcag aagctcttta     58080
atatatagtt ccatttgtct attttttggtt ttgtcacctg tgcttttaag gtaaaggaaa     58140
gcacagtgtg aagagacgac ctgttgaatg ggagaaaata tttgcaaaat gttcatccaa     58200
caagaaacat atctcaaaag aagacacaaa tagcccacag gtatatgaag aaatgctcaa     58260
catcactaat caacaaggaa atgcaaatta aaaccaccaa gagataccta ccatcttatc     58320
ccagttaaaa tgactactat taaaaacaca caaaagctct ccctctccct ttccctctcc     58380
ctctcgtctc cctctcccca cggtctccct ctccctctct ttccacggtc tccctctgat     58440
gccgagctga agctggactg tactgctgcc atctcggctc actgcaacct ccctgcctga     58500
ttctcctgcc tcagcctgcc gagtgcctgc gattacaggc acgcgccgcc acacctgact     58560
ggttttcgta ttttttttg gtggagacgg ggtttcnnnn nnnnnnnnnn nnnnnnnnnn     58620
nnnnnnnnnn nnnnnnnnnn nnnnnnnnnn nnnnnnnnnn nnnnnnnnnn nnnnnnnnnn     58680
nnnnnnnnnn nnnnnnnnnn nnnnnnnnnn nnnnnnnnnn nnnnnnnnnn nnnnnnnnnn     58740
nnnnnnnnnn nnnnnnnnnn nnnnnnnnnn nnnnnnnnnn nnnnnnnnnn nnnnnnnnnn     58800
nnnnnnnnnn nnnnnnnnnn nnnnnnnnnn nnnnnnnnnn nnnnnnnnnn nnnnnnnnnn     58860
nnnnnnnnnn nnnnnnnnnn nnnnnnnnnn nnnnnnnnnn nnnnnnnnnn nnnnnnnnnn     58920
nnnnnnnnnn nnnnnnnnnn nnnnnnnnnn nnnnnnnnnn nnnnnnnnnn nnnnnnnnnn     58980
nnnnnnnnnn nnnnnnnnnn nnnnnnnnnn nnnnnnnnnn nnnnnnnnnn nnnnnnnnnn     59040
nnnnnnnnnn nnnnnnnnnn nnnnnnnnnn nnnnnnnnnn nnnnnnnnnn nnnnnnnnnn     59100
nnnnnnnnnn nnnnnnnnnn nnnnnnnnnn nnnnnnnnnn nnnnnnnnnn nnnnnnnnnn     59160
nnnnnnnnnn nnnnnnnnnn nnnnnnnnnn nnnnnnnnnn nnnnnnnnnn nnnnnnnnnn     59220
nnnnnnnnnn nnnnnnnnnn nnnnnnnnnn nnnnnnnnnn nnnnnnnnnn nnnnnnnnnn     59280
nnnnnnnnnn nnnnnnnnnn nnnnnnnnnn nnnnnnnnnn nnnnnnnnnn nnnnnnnnnn     59340
nnnnnnnnnn nnnnnnnnnn nnnnnnnnnn nnnnnnnnnn nnnnnnnnnn nnnnnnnnnn     59400
nnnnnnnnnn nnnnnnnnnn nnnnnnnnnn nnnnnnnnnn nnnnnnnnnn nnnnnnnnnn     59460
nnnnnnnnnn nnnnnnnnnn nnnnnnnnnn nnnnnnnnnn nnnnnnnnnn nnnnnnnnnn     59520
nnnnnnnnnn nnnnnnnnnn nnnnnnnnnn nnnnnnnnnn nnnnnnnnnn nnnnnnnnnn     59580
nnnnnnnnnn nnnnnnnnnn nnnnnnnnnn nnnnnnnnnn nnnnnnnnnn nnnnnnnnnn     59640
nnnnnnnnnn nnnnnnnnnn nnnnnnnnnn nnnnnnnnnn nnnnnnnnnn nnnnntttgg     59700
acaatacggc gctttcaagg gcagagctcc ctgagctttc cacagtgtat gttgcccctg     59760
atttattgag actggggagt ggcgatgact tttaccaagt atactgcttg gaaacatctt     59820
gttagcaagg cgcatcctgc acagccctag atcccttaaa ccttgatttc atacaacaca     59880
tgcttttgtg agcttcaggt tgggtcaaag tggtttgttc aaagtgactg gggcaaagct     59940
acagattaac aacatctcag caaagaaatt gttgaaagta caggcctttt tcaaaatgga     60000
gtctcttatg tctttccttt ctacatagac acagtaagag tctgattgct ctttctttag     60060
cctacactca ctgaactgcc cttcccctcc gctgggccat gaccatggag aacaggtcca     60120
ctgtcctccc tgcgtggtgc accatggagg ctcagactcc gtcctcgagg ctggcaagaa     60180
```

```
gacagggtaa gacatgagcc tcctgataca ggagatgtct gtggagccca caggactgca    60240
acctcacact gcagggctgg aggcacagac tgactattta ctattctgtg gcctgggggg    60300
ctcaaggcac agagctcctc attagccaaa gtcacccaag ttcccaacct ctaaggattt    60360
cctcataata atgcaagaag aagaaaagtg agtgcccgta aagctttgg ggctcttcct     60420 ctaatcagga gaaagctggt gtgtattctt cacttctttc tttctttttt aaacatccaa    60480
ctgctttaat tttcatcttt tattatggga aaatatatca cttataaata ttaaaaaaaa    60540
cccacaaaaa taacagatgc tggcaagaat gtgtagataa ggaaactcac gtactgttgg    60600
gtgtgaatgt aaattaatac agccattatg gaaaacagta tggagatttc tcaaaaaaac    60660
cccaaaaaac taaaaataga actacctgcc gtgtgatcca gcaatcctcc tactgagtat    60720
ttatccaaag gaaagaaaat cattatctct aagggatacc tgcatcctca tgcttattgc    60780
agcactattc acaataacaa aggtatggat ccacctaagt gtccctcaac agatgaatag    60840
ataaagaaaa cttagtatat atgcacaaca gaatgctact cagccataaa aaaaatgaag    60900
tcttatcatt ttcagcaaca gagatggatc tggagttctt tatcttaagt aaaataagcc    60960
aggcccagca agacaaatac cacgttctct cttatgtggg agctacgaaa gtagatctca    61020
tggaagtaga gagtagaatg atagttatca gaggctggga agggtgtgta tgtggtgggg    61080
cagggaggat aaaaagaggt tggttaatgg gtacataatt agatagaagg agtaagttct    61140
aatgtttgat aacagagcag ggtgactgta attaacaaca atgtattctg tatttcaaat    61200
agctagaaga gaggacttga agtgttcctg acacatagaa atgacaaata ctcattatat    61260
atcaataaag aaagtggttg cacaatgtag cgggtagggg aagttacctg gttgttaaag    61320
ccttaataaa tatttatgta tctgaaaaaa aaatcaaaag atggccaatt taaccaaaag    61380
aatgcctctg gaataggcca ttgcagctaa tcattgacta tttcattagc tcattggttc    61440
attaactggc tcattgactg atacctttct aaaatctttt gaatttcttg aagaaaaaaa    61500
ctatgccaca atagtactga acaactgtct ccctctatct tacgttaatc caggagtgcc    61560
caaaacggga ttatttcaat taatcaccaa agcatatttg aatatctatt ttaaaaggtt    61620
ttcaattctg gattttaatg cttctgaatt ttaaaagtaa atgtaagtgt gaattttacc    61680
atacgtaaat tagactccaa acaaattgca caaaagtaca atgggaaagt agggcctagt    61740
tttcaatcac aatagctacc acttttcaaa caagtaccat gctattgttt aaaagttgta    61800
tatatattat ttaattctcc caatgagtta ggtattattg ttatctccat cttactgatg    61860
aagagagttt tagtcactta gcttaaggtc acacagctaa aaattggaga ctggactcaa    61920
cccaagtctg tttgactatc agaagttgta tttccgtctt taaaagttca catttaagta    61980
gatctacatt ggcagtctca ttactgagtg ctgctgcttc taatgtgttt ttcccttctt    62040
agggaccagc atgagcgacc ttctgctctc cagctcctga agcactcctt cttggagaga    62100
agtcactgaa tatacatcaa gactttcttc ccagttccac tgcagatgct cccttgctta    62160
attgtgggga atgatggcta agggatcttt gtttccccac tgaaaattca gtctaaccca    62220
gtttaagcag atcctatgga gtcattaact gaaagttgca gttacatatt agcctcctca    62280
agtgtcagac attattactc atagtatcag aaaacatgtt cttaataaca acaaaaaact    62340
atttcagtgt ttcagttttt gattgtccag gaactacatt ctctattgtt ttatatgaca    62400 tttctttta tttttggcct gtcctgtcaa ttttaatgtt gttagtttaa aataaattgt     62460
aaaaacaact tatattttct tgcttggtga gtaaagatgc ttacttaatt cgtccaaagc    62520
agagcagagg aaggcaggaa ggtaagttaa agagattcta gattctgtac tttggcagca    62580
```

```
atcttagcct aaaagattct aggaggctca aggcctaata gggaggaggt gagggcctcg    62640
gcatttcatt atcagagggc ccccaaactc ctcagatgtc tctgagaaat tgtgctagtt    62700
aaggcggcat cataaacctt gggctctttt ctctgtaatt tatttgtagt gatttgaagt    62760
ttttaatcta tttgcagtga atcaggtcat ttccatatgc agaactagct aagtctaaat    62820
cagctggtag gacaaaagct aggtctggta agggaaggat gattttttcca cagacctttg   62880 ctcatttcat ttgaatagtt acctctgctg aggtcatcct tcaaatactg ccattcccag    62940
aacattagta gacctcacaa aagtgagcat ggatgagtta gtagtattac aagccatttt    63000
aagttggtgg attaagcaat atttttttta gactgagtct tactctactg ccccaggctg    63060
gagtgcagtt gcgttatctt ggctcactgc aacaacctcc gcctgctggg ttcaagtgat    63120
tcttttgcct cagcctccca agtagctggg attacagttg cccaccacca cgcccagcta    63180 attttttgtat tttttgtgga aatgggggttt caccatgttg gccgagatgg agtttcactg   63240
tgttggccag gctgtcttga actccagacc tcaagtgatc cacctgcctt ggcctcccaa    63300
agtgctggga ttacaggcgt gagccatcgt gcccagccag gattaagcat ttttttataag  63360 gtttccattg ctgttgatct cactcatcca ctaaacttcg cacctattgt tctttttttt    63420
tattattatt atttgagatg gagtctcact ctgttgccca ggctggagtg cagtggcgtg    63480
atcttggctc accgcaacct ctgccacctg ggttcaagca attttcctgt ctcagcctgc    63540
caagtagctg agattactgg gacctgccac tgtgcctggc taatttgtgt agttttagta    63600
gagatggggt ttcaccatct tggccaggct ggtcttgaac tcctgacctc atgatccacc    63660
cgccttggcc tcccaaagtg ttgggattac aggcgtgagc catcgcgccc agccagcacc    63720
tattgctcta agctatagcc acagatattt ttattggctg ccgtcatttc aagctggtac    63780
aactaaaaat taactttagg agtattctaa tactggtatc aggatttgtc aaaacaaagc    63840
tggtttagtt tttatgaaat aaatgtgaaa tgctgtccag gtgaggtaaa aacagatttt    63900
actctggaca tgtaacatta gatgagtctt tgtgggtata acttttctca aatttttttt    63960
tcatatttaa gaaattaagg gaagaatatg tcctttattt tacttacttg tatctcaaca    64020
tgaccagaaa caacataatt ttgaaaggtt agggcttatt ccttttccat tttggaggga   64080
tcttcagcat tcttttcaaat ctgaatatta tattggattt taaagcaact atttacaatc   64140
aagcctgtta aaccctatgg ggaaagggca aagagtaaga cctgttaata ctgtgtatag    64200
agatcaccgt aatggacaca agaagttggt gttaacaagt ttattcctat tctactgaaa   64260
tataagggta ctgaagacaa ttttggaata ttgaacagaa acttcaaaaa gctgaagttt    64320
tggccaggca gggtggctca cccctgtaat cccagcactt tgggaggccg aggcaggtgg    64380
atcacttgag gtcaggagtt gggagaccag cctggccaac atgctgaaac cccatctcta    64440
ctaaaaatac aaaaaattag ctgggca                                        64467
```

<210> SEQ ID NO 4
<211> LENGTH: 168
<212> TYPE: PRT
<213> ORGANISM: Human

<400> SEQUENCE: 4

Met Glu Phe Val Pro Gly Gly Ser Ile Ser Ser Ile Ile Asn Arg Phe
 1               5                  10                  15

Gly Pro Leu Pro Glu Met Val Phe Cys Lys Tyr Thr Lys Gln Ile Leu
            20                  25                  30

-continued

```
Gln Gly Val Ala Tyr Leu His Glu Asn Cys Val Val His Arg Asp Ile
         35                  40                  45

Lys Gly Asn Asn Val Met Leu Met Pro Thr Gly Ile Ile Lys Leu Ile
 50                  55                  60

Asp Phe Gly Cys Ala Arg Arg Leu Ala Trp Ala Gly Leu Asn Gly Thr
 65                  70                  75                  80

His Ser Asp Met Leu Lys Ser Met His Gly Thr Pro Tyr Trp Met Val
                 85                  90                  95

Pro Glu Val Ile Asn Glu Ser Gly Tyr Gly Arg Lys Ser Asp Ile Trp
                100                 105                 110

Ser Ile Gly Cys Thr Val Phe Glu Met Ala Thr Gly Lys Pro Pro Leu
            115                 120                 125

Ala Ser Met Asp Arg Met Ala Ala Met Phe Tyr Ile Gly Ala His Arg
130                 135                 140

Gly Leu Met Pro Pro Leu Pro Asp His Phe Ser Glu Asn Ala Ala Asp
145                 150                 155                 160

Phe Val Arg Met Cys Leu Thr Arg
                165
```

<210> SEQ ID NO 5
<211> LENGTH: 275
<212> TYPE: PRT
<213> ORGANISM: Dictyostelium discoideum

<400> SEQUENCE: 5

```
Ile Ile Asn Glu His Glu Leu Ile Ser Asn His Asn Ile Lys Trp
 1               5                  10                  15

Gln Lys Gly Gln Ile Leu Gly Arg Gly Gly Tyr Gly Ser Val Tyr Leu
                 20                  25                  30

Gly Leu Asn Lys Asp Thr Gly Glu Leu Phe Ala Val Lys Gln Leu Glu
             35                  40                  45

Ile Val Asp Ile Asn Ser Asp Pro Lys Leu Lys Asn Met Ile Leu Ser
 50                  55                  60

Phe Ser Lys Glu Ile Glu Val Met Arg Ser Leu Arg His Asp Asn Ile
 65                  70                  75                  80

Val Arg Tyr Leu Gly Thr Ser Leu Asp Gln Ser Phe Leu Ser Val Phe
                 85                  90                  95

Leu Glu Tyr Ile Pro Gly Gly Ser Ile Ser Ser Leu Leu Gly Lys Phe
                100                 105                 110

Gly Ala Phe Ser Glu Asn Val Ile Lys Val Tyr Thr Lys Gln Ile Leu
            115                 120                 125

Gln Gly Leu Ser Phe Leu His Ala Asn Ser Ile Ile His Arg Asp Ile
130                 135                 140

Lys Gly Ala Asn Ile Leu Ile Asp Thr Lys Gly Ile Val Lys Leu Ser
145                 150                 155                 160

Asp Phe Gly Cys Ser Lys Ser Phe Ser Gly Ile Val Ser Gln Phe Lys
                165                 170                 175

Ser Met Gln Gly Thr Pro Tyr Trp Met Ala Pro Glu Val Ile Lys Gln
            180                 185                 190

Thr Gly His Gly Arg Ser Ser Asp Ile Trp Ser Leu Gly Cys Val Ile
        195                 200                 205

Val Glu Met Ala Thr Ala Gln Pro Pro Trp Ser Asn Ile Thr Glu Leu
210                 215                 220

Ala Ala Val Met Tyr His Ile Ala Ser Ser Asn Ser Ile Pro Asn Ile
225                 230                 235                 240
```

```
Pro Ser His Met Ser Gln Glu Ala Phe Asp Phe Leu Asn Leu Cys Phe
            245                 250                 255

Lys Arg Asp Pro Lys Glu Arg Pro Asp Ala Asn Gln Leu Leu Lys His
            260                 265                 270

Pro Phe Ile
        275

<210> SEQ ID NO 6
<211> LENGTH: 277
<212> TYPE: PRT
<213> ORGANISM: Arabidopsis thaliana

<400> SEQUENCE: 6

Asn Thr Val Asp Met Ala Pro Pro Ile Ser Trp Arg Lys Gly Gln Leu
 1               5                  10                  15

Ile Gly Arg Gly Ala Phe Gly Thr Val Tyr Met Gly Met Asn Leu Asp
            20                  25                  30

Ser Gly Glu Leu Leu Ala Val Lys Gln Val Leu Ile Ala Ala Asn Phe
        35                  40                  45

Ala Ser Lys Glu Lys Thr Gln Ala His Ile Gln Glu Leu Glu Glu Glu
    50                  55                  60

Val Lys Leu Leu Lys Asn Leu Ser His Pro Asn Ile Val Arg Tyr Leu
65                  70                  75                  80

Gly Thr Val Arg Glu Asp Asp Thr Leu Asn Ile Leu Leu Glu Phe Val
                85                  90                  95

Pro Gly Gly Ser Ile Ser Ser Leu Leu Glu Lys Phe Gly Pro Phe Pro
            100                 105                 110

Glu Ser Val Val Arg Thr Tyr Thr Arg Gln Leu Leu Leu Gly Leu Glu
        115                 120                 125

Tyr Leu His Asn His Ala Ile Met His Arg Asp Ile Lys Gly Ala Asn
    130                 135                 140

Ile Leu Val Asp Asn Lys Gly Cys Ile Lys Leu Ala Asp Phe Gly Ala
145                 150                 155                 160

Ser Lys Gln Val Ala Glu Leu Ala Thr Met Thr Gly Ala Lys Ser Met
                165                 170                 175

Lys Gly Thr Pro Tyr Trp Met Ala Pro Glu Val Ile Leu Gln Thr Gly
            180                 185                 190

His Ser Phe Ser Ala Asp Ile Trp Ser Val Gly Cys Thr Val Ile Glu
        195                 200                 205

Met Val Thr Gly Lys Ala Pro Trp Ser Gln Gln Tyr Lys Glu Val Ala
    210                 215                 220

Ala Ile Phe Phe Ile Gly Thr Thr Lys Ser His Pro Pro Ile Pro Asp
225                 230                 235                 240

Thr Leu Ser Ser Asp Ala Lys Asp Phe Leu Leu Lys Cys Leu Gln Glu
                245                 250                 255

Val Pro Asn Leu Arg Pro Thr Ala Ser Glu Leu Leu Lys His Pro Phe
            260                 265                 270

Val Met Gly Lys His
        275

<210> SEQ ID NO 7
<211> LENGTH: 277
<212> TYPE: PRT
<213> ORGANISM: Arabidopsis thaliana

<400> SEQUENCE: 7
```

-continued

```
Asn Thr Val Asp Met Ala Pro Pro Ile Ser Trp Arg Lys Gly Gln Leu
 1               5                  10                  15

Ile Gly Arg Gly Ala Phe Gly Thr Val Tyr Met Gly Met Asn Leu Asp
            20                  25                  30

Ser Gly Glu Leu Leu Ala Val Lys Gln Val Leu Ile Ala Ala Asn Phe
            35                  40                  45

Ala Ser Lys Glu Lys Thr Gln Ala His Ile Gln Glu Leu Glu Glu Glu
     50                  55                  60

Val Lys Leu Leu Lys Asn Leu Ser His Pro Asn Ile Val Arg Tyr Leu
 65                  70                  75                  80

Gly Thr Val Arg Glu Asp Asp Thr Leu Asn Ile Leu Leu Glu Phe Val
                 85                  90                  95

Pro Gly Gly Ser Ile Ser Ser Leu Leu Glu Lys Phe Gly Pro Phe Pro
                100                 105                 110

Glu Ser Val Val Arg Thr Tyr Thr Arg Gln Leu Leu Leu Gly Leu Glu
            115                 120                 125

Tyr Leu His Asn His Ala Ile Met His Arg Asp Ile Lys Gly Ala Asn
    130                 135                 140

Ile Leu Val Asp Asn Lys Gly Cys Ile Lys Leu Ala Asp Phe Gly Ala
145                 150                 155                 160

Ser Lys Gln Val Ala Glu Leu Ala Thr Met Thr Gly Ala Lys Ser Met
                165                 170                 175

Lys Gly Thr Pro Tyr Trp Met Ala Pro Glu Val Ile Leu Gln Thr Gly
            180                 185                 190

His Ser Phe Ser Ala Asp Ile Trp Ser Val Gly Cys Thr Val Ile Glu
        195                 200                 205

Met Val Thr Gly Lys Ala Pro Trp Ser Gln Gln Tyr Lys Glu Val Ala
    210                 215                 220

Ala Ile Phe Phe Ile Gly Thr Thr Lys Ser His Pro Pro Ile Pro Asp
225                 230                 235                 240

Thr Leu Ser Ser Asp Ala Lys Asp Phe Leu Leu Lys Cys Leu Gln Glu
                245                 250                 255

Val Pro Asn Leu Arg Pro Thr Ala Ser Glu Leu Leu Lys His Pro Phe
                260                 265                 270

Val Met Gly Lys His
                275
```

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the MEK kinase alpha subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) J. Biol. Chem. 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) Annu. Rev. Cell. Biol. 8:463–93). Regulation of PTK activity may therefore be an important strategy in controlling some types of cancer.

MEKKα, probably encodes a MEK kinase, since it has very high homology in the kinase domain to known MEKKs, the first kinase in MAP kinase cascades. MEKKα plays a key role in a new regulatory pathway by which cell-type differentiation, morphogenesis, spatial patterning, and developmental timing are controlled. The components of three MAP kinase pathways required for chemotaxis, activation of adenylyl cyclase, and prespore cell differentiation have been identified in Dictyostelium. These pathways seem to be independent pathways and are unrelated to the pathway containing MEKKα. MEKKα protein contains an F-box and a WD40 repeats. The F-box has a domain known to control ubiquitin-mediated degradation of proteins. WD40 repeats are important for targeting MEKKα to the cell cortex or possibly the plasma membrane. Cells deficient in MEKKα, develop precociously and exhibit abnormal cell-type patterning with an increase in one of the prestalk compartments (pstO), a concomitant reduction in the prespore domain, and a loss of the sharp compartment boundaries, resulting in overlapping prestalk and prespore domains. Overexpression of MEKKα, or MEKKα lacking the WD40 repeats results in very delayed development and a severe loss of compartment boundaries. MEKKα activity is differentially regulated temporally and in a cell-type-specific fashion via developmentally regulated ubiquitination/deubiquitination, wherein MAP kinase cascade components can be controlled. Cells lacking the ubiquitin hydrolase have phenotypes similar to those of MEKKα, null (MEKKα-) cells, which indicates a direct genetic and biochemical interaction between MEKKα, the UBC, and the UBP. UBC and UBP differentially control MEKKα ubiquitination/deubiquitination and degradation through the F-box/WD40 repeats in a cell-type-specific and temporally regulated manner. (Chung et al., Genes Dev Nov. 15, 1998;12(22):3564–78).

Kinase proteins, particularly members of the MEK kinase alpha subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the MEK kinase alpha subfamily.

SUMMARY OF THE INVENTION

The present invention is based in part on the identification of amino acid sequences of human kinase peptides and proteins that are related to the MEK kinase alpha subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the multiple sclerosis lesions and mixed tissue (brain, heart, kidney, lung, spleen, testis, leukocyte).

DESCRIPTION OF THE FIGURE SHEETS

FIG. 1 provides the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the multiple sclerosis lesions and mixed tissue (brain, heart, kidney, lung, spleen, testis, leukocyte).

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 35 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the MEK kinase alpha subfamily. Utilizing these sequences, additional genomic sequences were assembled and transcript and/or cDNA sequences were isolated and characterized. Based on this analysis, the present invention provides amino acid sequences of human kinase peptides and proteins that are related to the MEK kinase alpha subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the MEK kinase alpha subfamily and the expression pattern observed. Experimental data as provided in FIG. 1 indicates expression in the multiple sclerosis lesions and mixed tissue (brain, heart, kidney, lung, spleen, testis, leukocyte). The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known MEK kinase alpha family or subfamily of kinase proteins.

Specific Embodiments

Peptide Molecules

The present invention provides nucleic acid sequences that encode protein molecules that have been identified as being members of the kinase family of proteins and are related to the MEK kinase alpha subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the multiple sclerosis lesions and mixed tissue (brain, heart, kidney, lung, spleen, testis, leukocyte). For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 2 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 2 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been identified in a gene encoding the kinase protein of the present invention. 35 SNP variants were found, including 6 indels (indicated by a "−") and 3 SNPs in exons.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182:626–646 (1990 and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Substantial chemical and structural homology exists between the MEK kinase alpha protein described herein and MEKK alpha in Dictyostelium (see FIG. 1). As discussed in the background, Dictyostelium MEKK alpha is known in the art to be involved in cell signaling, cell differentiation. Accordingly, the MEK kinase alpha protein, and the encoding gene, provided by the present invention is useful for treating, preventing, and/or diagnosing diseases or other disorders associated with regulatory pathway, such as cancer.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte). A large percentage of pharmaceutical agents are being developed that modulate the activity of kinase proteins, particularly members of the MEK kinase alpha subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the multiple sclerosis lesions and mixed tissue (brain, heart, kidney, lung, spleen, testis, leukocyte). Such uses can readily be determined using the information provided herein, that which is known in the art, and routine experimentation.

The proteins of the present invention (including variants and fragments that may have been disclosed prior to the present invention) are useful for biological assays related to kinases that are related to members of the MEK kinase alpha subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte).

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the multiple sclerosis lesions and mixed tissue (brain, heart, kidney, lung, spleen, testis, leukocyte). In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte).

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St.

Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the multiple sclerosis lesions and mixed tissue (brain, heart, kidney, lung, spleen, testis, leukocyte). These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the multiple sclerosis lesions and mixed tissue (brain, heart, kidney, lung, spleen, testis, leukocyte). The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the multiple sclerosis lesions and mixed tissue (brain, heart, kidney, lung, spleen, testis, leukocyte). Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte). Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the multiple sclerosis lesions and mixed tissue (brain, heart, kidney, lung, spleen, testis, leukocyte). If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the multiple sclerosis lesions and mixed tissue (brain, heart, kidney, lung, spleen, testis, leukocyte). The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the multiple sclerosis lesions and mixed tissue (brain, heart, kidney, lung, spleen, testis, leukocyte). Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 2 by ePCR.

FIG. 3 provides information on SNPs that have been identified in a gene encoding the kinase protein of the present invention. 35 SNP variants were found, including 6 indels (indicated by a "–") and 3 SNPs in exons.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 35 different nucleotide positions.

The probe can correspond to any sequence along the entire length of the nucleic acid molecules provided in the Figures. Accordingly, it could be derived from 5' non-coding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 2 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte). Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte).

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the multiple sclerosis lesions and mixed tissue (brain, heart, kidney, lung, spleen, testis, leukocyte). The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte). Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the multiple sclerosis lesions and mixed tissue (brain, heart, kidney, lung, spleen, testis, leukocyte).

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been identified in a gene encoding the kinase protein of the present invention. 35 SNP variants were found, including 6 indels (indicated by a "–") and 3 SNPs in exons. As indicated by the data presented in FIG. 3, the map position was determined to be on chromosome 2 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241: 1077–1080 (1988); and Nakazawa et al., *PNAS* 91 :360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been identified in a gene encoding the kinase protein of the present invention. 35 SNP variants were found, including 6 indels (indicated by a "-") and 3 SNPs in exons.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the multiple sclerosis lesions by a virtual northern blot analysis. In addition, PCR-based tissue screening panel indicates expression in the mixed tissue (brain, heart, kidney, lung, spleen, testis, leukocyte). For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been identified in a gene encoding the kinase protein of the present invention. 35 SNP variants were found, including 6 indels (indicated by a "–") and 3 SNPs in exons.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide, wherein the amino acid sequence of said polypeptide consists of SEQ ID NO:2.

2. An isolated polypeptide, wherein the amino acid sequence of said polypeptide comprises SEQ ID NO:2.

3. An isolated MEK kinase, wherein the amino acid sequence of said MEK kinase consists of an amino acid sequence having at least 99% sequence identity to SEQ ID NO:2.

4. An isolated MEK kinase, wherein the amino acid sequence of said MEK kinase comprises an amino acid sequence having at least 99% sequence identity to SEQ ID NO:2.

5. The polypeptide of claim 1, further comprising a heterologous amino acid sequence.

6. The polypeptide of claim 2, further comprising a heterologous amino acid sequence.

7. The MEK kinase of claim 3, further comprising a heterologous amino acid sequence.

8. The MEK kinase of claim 4, further comprising a heterologous amino acid sequence.

9. A composition comprising the polypeptide of claim 1 and a carrier.

10. A composition comprising the polypeptide of claim 2 and a carrier.

11. A composition comprising the MEK kinase of claim 3 and a carrier.

12. A composition comprising the MEK kinase of claim 4 and a carrier.

13. A composition comprising the polypeptide of claim 5 and a carrier.

14. A composition comprising the polypeptide of claim 6 and a carrier.

15. A composition comprising the MEK kinase of claim 7 and a carrier.

16. A composition comprising the MEK kinase of claim 8 and a carrier.

* * * * *